US010822407B2

(12) United States Patent
Johns

(10) Patent No.: US 10,822,407 B2
(45) Date of Patent: Nov. 3, 2020

(54) ANTIBODIES TO HUMAN RESISTIN

(71) Applicant: THE JOHNS HOPKINS UNIVERSITY, Baltimore, MD (US)

(72) Inventor: Roger A. Johns, Reisterstown, MD (US)

(73) Assignee: The Johns Hopkins University, Baltimore, MD (US)

(*) Notice: Subject to any disclaimer, the term of this patent is extended or adjusted under 35 U.S.C. 154(b) by 235 days.

(21) Appl. No.: 14/899,342

(22) PCT Filed: Jun. 17, 2014

(86) PCT No.: PCT/US2014/042706
§ 371 (c)(1),
(2) Date: Dec. 17, 2015

(87) PCT Pub. No.: WO2014/204941
PCT Pub. Date: Dec. 24, 2014

(65) Prior Publication Data

US 2016/0130341 A1 May 12, 2016

Related U.S. Application Data

(60) Provisional application No. 61/835,855, filed on Jun. 17, 2013.

(51) Int. Cl.

| | |
|---|---|
| ***C07K 16/26*** | (2006.01) |
| ***A61K 39/395*** | (2006.01) |
| ***A61P 9/10*** | (2006.01) |
| ***A61P 3/08*** | (2006.01) |
| *C07K 14/575* | (2006.01) |

(52) U.S. Cl.
CPC .......... *C07K 16/26* (2013.01); *A61K 39/3955* (2013.01); *A61P 3/08* (2018.01); *A61P 9/10* (2018.01); *C07K 14/575* (2013.01); *C07K 2317/21* (2013.01); *C07K 2317/24* (2013.01); *C07K 2317/33* (2013.01); *C07K 2317/54* (2013.01); *C07K 2317/55* (2013.01); *C07K 2317/565* (2013.01); *C07K 2317/622* (2013.01); *C07K 2317/64* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 2003/0138826 A1 | 7/2003 | Lazar et al. |
| 2011/0071277 A1 | 3/2011 | Blake et al. |

FOREIGN PATENT DOCUMENTS

| | | |
|---|---|---|
| EP | 1180114 B1 | 9/2011 |
| KR | 10-0493932 B1 | 6/2005 |

OTHER PUBLICATIONS

Youn et al, 2004. Journal of Clinical Endocrinology & Metabolism. 88: 150-156.*

Rudikoff et al (Proc Natl Acad Sci USA 1982 vol. 79 pp. 1979-1983).*

MacCallum et al. (Journal of Molecular. Biology, 1996, vol. 262, pp. 732-745).*

Pascalis et al (Journal of Immunology, 2002, vol. 169, pp. 3076-3084).*

Casset et al (Biochemical and Biophysical Research Communications, 2003, vol. 307, pp. 198-205).*

Vajdos et al (Journal of Molecular biology, 2002, vol. 320, pp. 415-428).*

Holm et al (Molecular Immunology, 2007, vol. 44, pp. 1075-1084).*

Chen et al. (Journal of Molecular Biology, 1999, vol. 293, pp. 865-881).*

Wu et al. (Journal of Molecular Biology, 1999, vol. 294, pp. 151-162).*

Al Hannan et al, 2015. Diabetology & Metabolic Syndrome. 7:54; 11 pages as printed.*

Santos et al, 2014. Clin Cardiol. 37(1): 21-25.*

Fan, C., et al., "Choosing the right antibody for resistin-like molecule (RELM/FIZZ) family members", Histochem Cell Biol, (2013) vol. 139, pp. 605-613.

* cited by examiner

*Primary Examiner* — Zachary C Howard

(74) *Attorney, Agent, or Firm* — Johns Hopkins Technology Ventures

(57) ABSTRACT

The present invention relates to the field of pulmonary, cardiac and inflammatory disorders. More specifically, the present invention provides methods and compositions for treating disorders associated with Resistin. In a specific embodiment, the present invention provides an antibody that binds human Resistin.

6 Claims, 9 Drawing Sheets

Specification includes a Sequence Listing.

Plate Layout

Assay Plate

| | 1 | 2 | 3 | 4 | 5 | 6 | 7 | 8 | 9 | 10 | 11 | 12 |
|---|---|---|---|---|---|---|---|---|---|---|---|---|
| A | 1A 100ng/mL | 1B 100ng/mL | 1C 100ng/mL | 1D 100ng/mL | 13A 100ng/mL | 13B 100ng/mL | 13C 100ng/mL | 13D 100ng/mL | R&DB 100ng/mL | R&DC 100ng/mL | R&DD 100ng/mL | No Ab 100ng/mL |
| B | 1A 25ng/mL | 1B 25ng/mL | 1C 25ng/mL | 1D 25ng/mL | 13A 25ng/mL | 13B 25ng/mL | 13C 25ng/mL | 13D 25ng/mL | R&DB 25ng/mL | R&DC 25ng/mL | R&DD 25ng/mL | No Ab 25ng/mL |
| C | 1A 10ng/mL | 1B 10ng/mL | 1C 10ng/mL | 1D 10ng/mL | 13A 10ng/mL | 13B 10ng/mL | 13C 10ng/mL | 13D 10ng/mL | R&DB 10ng/mL | R&DC 10ng/mL | R&DD 10ng/mL | No Ab 10ng/mL |
| D | 1A 1ng/mL | 1B 1ng/mL | 1C 1ng/mL | 1D 1ng/mL | 13A 1ng/mL | 13B 1ng/mL | 13C 1ng/mL | 13D 1ng/mL | R&DB 1ng/mL | R&DC 1ng/mL | R&DD 1ng/mL | No Ab 1ng/mL |
| E | 17A 100ng/mL | 17B 100ng/mL | 17C 100ng/mL | 17D 100ng/mL | 21A 100ng/mL | 21B 100ng/mL | 21C 100ng/mL | 21D 100ng/mL | 41A 100ng/mL | 41B 100ng/mL | 41C 100ng/mL | 41D 100ng/mL |
| F | 17A 25ng/mL | 17B 25ng/mL | 17C 25ng/mL | 17D 25ng/mL | 21A 25ng/mL | 21B 25ng/mL | 21C 25ng/mL | 21D 25ng/mL | 41A 25ng/mL | 41B 25ng/mL | 41C 25ng/mL | 41D 25ng/mL |
| G | 17A 10ng/mL | 17B 10ng/mL | 17C 10ng/mL | 17D 10ng/mL | 21A 10ng/mL | 21B 10ng/mL | 21C 10ng/mL | 21D 10ng/mL | 41A 10ng/mL | 41B 10ng/mL | 41C 10ng/mL | 41D 10ng/mL |
| H | 17A 1ng/mL | 17B 1ng/mL | 17C 1ng/mL | 17D 1ng/mL | 21A 1ng/mL | 21B 1ng/mL | 21C 1ng/mL | 21D 1ng/mL | 41A 1ng/mL | 41B 1ng/mL | 41C 1ng/mL | 41D 1ng/mL |

Notes

1. 11.07.12 Coat
2. A, B, C, D are Ab dil
3. 11.08.12 Block
4. 11.09.12 Finish/Read
5.
6.
7.
8.

FIG. 8

The Construct of Human IgG1

Leader | VH | CH123

Leader | VL | CK

FIG. 10

| Clones | OD490 | | | |
|---|---|---|---|---|
| | Coating: hRELMB | | Coating: hResistin | |
| 1 | 0.266 | 0.271 | 0.378 | 0.383 |
| 2 | 0.321 | 0.312 | 0.490 | 0.485 |
| 3 | 0.092 | 0.098 | 0.112 | 0.115 |
| 4 | 0.107 | 0.110 | 0.112 | 0.114 |
| 5 | 0.095 | 0.096 | 0.109 | 0.107 |
| 9 | 0.099 | 0.108 | 0.107 | 0.110 |
| 11 | 0.097 | 0.109 | 0.105 | 0.107 |
| 13 | 0.473 | 0.454 | 0.659 | 0.667 |
| 16 | 0.105 | 0.115 | 0.118 | 0.114 |
| 17 | 0.093 | 0.099 | 0.113 | 0.116 |
| 18 | 0.288 | 0.283 | 0.556 | 0.557 |
| 21 | 0.109 | 0.111 | 0.122 | 0.127 |
| 23 | 0.091 | 0.095 | 0.109 | 0.108 |
| 24 | 0.090 | 0.096 | 0.104 | 0.110 |
| 26 | 0.101 | 0.103 | 0.112 | 0.116 |
| 27 | 0.121 | 0.119 | 0.180 | 0.189 |
| 41 | 0.113 | 0.115 | 0.132 | 0.134 |
| Medium | 0.087 | 0.085 | 0.096 | 0.092 |
| PBS | 0.088 | 0.082 | 0.090 | 0.090 |

FIG. 11

| Clone | rIgG[ug] | ELISA Binding | Clone | rIgG[ug] | ELISA Binding | Clone | rIgG[ug] | ELISA Binding |
|---|---|---|---|---|---|---|---|---|
| 1 | 510 | +++ | 2 | 510 | + | 3 | 0 | + |
| 4 | 675 | - | 5 | 1.25 | - | 9 | 0 | - |
| 11 | 1675 | + | 13 | 1000 | +++ | 16 | 1000 | + |
| 17 | 125 | ++ | 18 | 260 | + | 21 | 750 | +++++ |
| 23 | 1250 | - | 24 | 800 | - | 26 | 3760 | + |
| 27 | 500 | + | 41 | 500 | +++++ | | | |

FIG. 12

SEQUENCE LISTING

<160> NUMBER OF SEQ ID NOS: 242

<210> SEQ ID NO 1
<211> LENGTH: 720
<212> TYPE: DNA
<213> ORGANISM: Artificial Sequence
<220> FEATURE:
<223> OTHER INFORMATION: Description of Artificial Sequence: Synthetic clone 1 polynucleotide

<400> SEQUENCE: 1

```
gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcatcg atttctcagc ggggtcggaa gacactgtac    180

gcagactccg tgaagggccg gttcaccatc tccagagaca attccaagaa cacgctgtat    240

ctgcaaatga acagcctgag agccgaggac acggccgtat attactgtgc gaaaggtctg    300

cgtcgttttg actactgggg ccagggaacc ctggtcaccg tctcgagcgg tggaggcggt    360

tcaggcggag gtggcagcgg cggtggcggg tcgacggaca tccagatgac ccagtctcca    420

tcctccctgt ctgcatctgt aggagacaga gtcaccatca cttgccgggc aagtcagagc    480

attagcagct atttaaattg gtatcagcag aaaccaggga aagcccctaa gctcctgatc    540

tatatggcat cccatttgca aagtggggtc ccatcaaggt tcagtggcag tggatctggg    600

acagatttca ctctcaccat cagcagtctg caacctgaag attttgcaac ttactactgt    660

caacagccgc gttctacgcc tttgacgttc ggtcaaggga ccaaggtgga aatcaaacgg    720
```

<210> SEQ ID NO 2
<211> LENGTH: 240
<212> TYPE: PRT
<213> ORGANISM: Artificial Sequence
<220> FEATURE:
<223> OTHER INFORMATION: Description of Artificial Sequence: Synthetic clone 1 polypeptide
<220> FEATURE:
<221> NAME/KEY: misc_feature
<222> LOCATION: (1)..(116)
<223> OTHER INFORMATION: Variable heavy chain
<220> FEATURE:
<221> NAME/KEY: misc_feature
<222> LOCATION: (31)..(35)
<223> OTHER INFORMATION: Variable heavy chain CDR1
<220> FEATURE:
<221> NAME/KEY: misc_feature
<222> LOCATION: (50)..(69)
<223> OTHER INFORMATION: Variable heavy chain CDR2
<220> FEATURE:
<221> NAME/KEY: misc_feature
<222> LOCATION: (99)..(105)
<223> OTHER INFORMATION: Variable heavy chain CDR3
<220> FEATURE:
<221> NAME/KEY: misc_feature
<222> LOCATION: (133)..(240)
<223> OTHER INFORMATION: Variable light chain
<220> FEATURE:
<221> NAME/KEY: misc_feature
<222> LOCATION: (156)..(166)
<223> OTHER INFORMATION: Variable light chain CDR1
<220> FEATURE:
<221> NAME/KEY: misc_feature
<222> LOCATION: (182)..(188)
<223> OTHER INFORMATION: Variable light chain CDR2
<220> FEATURE:
<221> NAME/KEY: misc_feature
<222> LOCATION: (223)..(229)
<223> OTHER INFORMATION: Variable light chain CDR3

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Gln Arg Gly Arg Lys Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Arg Arg Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Met Ala Ser His Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Pro Arg
    210                 215                 220

Ser Thr Pro Leu Thr Phe Gly Gln Gly Thr Lys Val Glu Ile Lys Arg
225                 230                 235                 240


<210> SEQ ID NO 3
<211> LENGTH: 116
<212> TYPE: PRT
<213> ORGANISM: Artificial Sequence
<220> FEATURE:
<223> OTHER INFORMATION: Description of Artificial Sequence: Synthetic
      clone 1 variable heavy chain polypeptide

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Gln Arg Gly Arg Lys Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Arg Arg Phe Asp Tyr Trp Gly Gln Gly Thr Leu Val
            100                 105                 110

Thr Val Ser Ser
```

```
        115


<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      clone 1 variable heavy chain CDR1 peptide

<400> SEQUENCE: 4

Ser Tyr Ala Met Ser
1               5


<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      clone 1 variable heavy chain CDR2 peptide

<400> SEQUENCE: 5

Ser Ile Ser Gln Arg Gly Arg Lys Thr Leu Tyr Ala Asp Ser Val Lys
1               5                   10                  15

Gly Arg Phe Thr
            20


<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 1 variable heavy chain CDR3 peptide

<400> SEQUENCE: 6

Gly Leu Arg Arg Phe Asp Tyr
1               5


<210> SEQ ID NO 7
<211> LENGTH: 108
<212> TYPE: PRT
<213> ORGANISM: Artificial Sequence
<220> FEATURE:
<223> OTHER INFORMATION: Description of Artificial Sequence: Synthetic
      clone 1 variable light chain polypeptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Met Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Arg Ser Thr Pro Leu
                85                  90                  95

Thr Phe Gly Gln Gly Thr Lys Val Glu Ile Lys Arg
            100                 105
```

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic clone 1 variable light chain CDR1 peptide

<400> SEQUENCE: 8

```
Arg Ala Ser Gln Ser Ile Ser Ser Tyr Leu Asn
1               5                   10
```

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic clone 1 variable light chain CDR2 peptide

<400> SEQUENCE: 9

```
Met Ala Ser His Leu Gln Ser
1               5
```

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic clone 1 variable light chain CDR3 peptide

<400> SEQUENCE: 10

```
Pro Arg Ser Thr Pro Leu Thr
1               5
```

<210> SEQ ID NO 11
<211> LENGTH: 720
<212> TYPE: DNA
<213> ORGANISM: Artificial Sequence
<220> FEATURE:
<223> OTHER INFORMATION: Description of Artificial Sequence: Synthetic clone 2 polynucleotide

<400> SEQUENCE: 11

```
gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcaacg attactacta ctggtaccgc gacatggtac    180

gcagactccg tgaagggccg gttcaccatc tccagagaca attccaagaa cacgctgtat    240

ctgcaaatga acagcctgag agccgaggac acggccgtat attactgtgc gaaaactctt    300

cagcgttttg actactgggg ccagggaacc ctggtcaccg tctcgagcgg tggaggcggt    360

tcaggcggag gtggcagcgg cggtggcggg tcgacggaca tccagatgac ccagtctcca    420

tcctccctgt ctgcatctgt aggagacaga gtcaccatca cttgccgggc aagtcagagc    480

attagcagct atttaaattg gtatcagcag aaaccaggga aagcccctaa gctcctgatc    540

tatgaggcat ccgtgttgca aagtggggtc ccatcaaggt tcagtggcag tggatctggg    600

acagatttca ctctcaccat cagcagtctg caacccgaag attttgcaac ttactactgt    660

caacagccga ggtctctgcc tatgacgttc ggccaaggga ccaaggtgga aatcaaacgg    720
```

<210> SEQ ID NO 12

```
<211> LENGTH: 240
<212> TYPE: PRT
<213> ORGANISM: Artificial Sequence
<220> FEATURE:
<223> OTHER INFORMATION: Description of Artificial Sequence: Synthetic
      clone 2 polypeptide
<220> FEATURE:
<221> NAME/KEY: misc_feature
<222> LOCATION: (1)..(116)
<223> OTHER INFORMATION: Variable heavy chain
<220> FEATURE:
<221> NAME/KEY: misc_feature
<222> LOCATION: (31)..(35)
<223> OTHER INFORMATION: Variable heavy chain CDR1
<220> FEATURE:
<221> NAME/KEY: misc_feature
<222> LOCATION: (50)..(69)
<223> OTHER INFORMATION: Variable heavy chain CDR2
<220> FEATURE:
<221> NAME/KEY: misc_feature
<222> LOCATION: (99)..(105)
<223> OTHER INFORMATION: Variable heavy chain CDR3
<220> FEATURE:
<221> NAME/KEY: misc_feature
<222> LOCATION: (133)..(240)
<223> OTHER INFORMATION: Variable light chain
<220> FEATURE:
<221> NAME/KEY: misc_feature
<222> LOCATION: (156)..(166)
<223> OTHER INFORMATION: Variable light chain CDR1
<220> FEATURE:
<221> NAME/KEY: misc_feature
<222> LOCATION: (182)..(188)
<223> OTHER INFORMATION: Variable light chain CDR2
<220> FEATURE:
<221> NAME/KEY: misc_feature
<222> LOCATION: (223)..(229)
<223> OTHER INFORMATION: Variable light chain CDR3

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Thr Thr Thr Gly Thr Ala Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Leu Gln Arg Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Glu Ala Ser Val Leu Gln Ser Gly Val Pro Ser
            180                 185                 190

Arg Phe Ser Gly Ser Gly Ser Gly Thr Asp Phe Thr Leu Thr Ile Ser
        195                 200                 205
```

```
Ser Leu Gln Pro Glu Asp Phe Ala Thr Tyr Tyr Cys Gln Gln Pro Arg
    210                 215                 220

Ser Leu Pro Met Thr Phe Gly Gln Gly Thr Lys Val Glu Ile Lys Arg
225                 230                 235                 240


<210> SEQ ID NO 13
<211> LENGTH: 116
<212> TYPE: PRT
<213> ORGANISM: Artificial Sequence
<220> FEATURE:
<223> OTHER INFORMATION: Description of Artificial Sequence: Synthetic
      clone 2 variable heavy chain polypeptide

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Thr Thr Thr Gly Thr Ala Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Leu Gln Arg Phe Asp Tyr Trp Gly Gln Gly Thr Leu Val
            100                 105                 110

Thr Val Ser Ser
        115


<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      clone 2 variable heavy chain CDR1 peptide

<400> SEQUENCE: 14

Ser Tyr Ala Met Ser
1               5


<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      clone 2 variable heavy chain CDR2 peptide

<400> SEQUENCE: 15

Thr Ile Thr Thr Thr Gly Thr Ala Thr Trp Tyr Ala Asp Ser Val Lys
1               5                   10                  15

Gly Arg Phe Thr
            20


<210> SEQ ID NO 16
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      clone 2 variable heavy chain CDR3 peptide

<400> SEQUENCE: 16

Thr Leu Gln Arg Phe Asp Tyr
1               5


<210> SEQ ID NO 17
<211> LENGTH: 108
<212> TYPE: PRT
<213> ORGANISM: Artificial Sequence
<220> FEATURE:
<223> OTHER INFORMATION: Description of Artificial Sequence: Synthetic
      clone 2 variable light chain polypeptide

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Glu Ala Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Arg Ser Leu Pro Met
                85                  90                  95

Thr Phe Gly Gln Gly Thr Lys Val Glu Ile Lys Arg
            100                 105


<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      clone 2 variable light chain CDR1 peptide

<400> SEQUENCE: 18

Arg Ala Ser Gln Ser Ile Ser Ser Tyr Leu Asn
1               5                   10


<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 2 variable light chain CDR2 peptide

<400> SEQUENCE: 19

Glu Ala Ser Val Leu Gln Ser
1               5


<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 2 variable light chain CDR3 peptide

<400> SEQUENCE: 20
```

```
Pro Arg Ser Leu Pro Met Thr
1               5


<210> SEQ ID NO 21
<211> LENGTH: 720
<212> TYPE: DNA
<213> ORGANISM: Artificial Sequence
<220> FEATURE:
<223> OTHER INFORMATION: Description of Artificial Sequence: Synthetic
      clone 3 polynucleotide

<400> SEQUENCE: 21

gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcaggg attgggctta gtggtggggg gacacagtac    180

gcagactccg tgaagggcag gttcaccatc tccagagaca attccaagaa cacgctgtat    240

ctgcaaatga acagcctgag agccgaggac acggccgtat attactgtgc gaaaggtact    300

actcggtttg actactgggg ccagggaacc ctggtcaccg tctcgagcgg tggaggcggt    360

tcaggcggag gtggcagcgg cggtggcggg tcgacgaaca tccagatgac ccagtctcca    420

tcctccctgt ctgcatctgt aggagacaga gtcaccatca cttgccgggc aagtcagagc    480

attagcagct atttaaattg gtatcagcag aaaccaggga aagcccctaa gctcctgatc    540

tataaggcat cccgtttgca aagtggggtc ccatcaaggt tcagtggcag tggatctggg    600

acagatttca ctctcaccat cagcagtctg caacctgaag attttgcaac ttactactgt    660

caacagtttt tggttcttcc tcgtacgttc ggccaaggga ccaaggtgga aatcaaacgg    720


<210> SEQ ID NO 22
<211> LENGTH: 240
<212> TYPE: PRT
<213> ORGANISM: Artificial Sequence
<220> FEATURE:
<223> OTHER INFORMATION: Description of Artificial Sequence: Synthetic
      clone 3 polypeptide
<220> FEATURE:
<221> NAME/KEY: misc_feature
<222> LOCATION: (1)..(116)
<223> OTHER INFORMATION: Variable heavy chain
<220> FEATURE:
<221> NAME/KEY: misc_feature
<222> LOCATION: (31)..(35)
<223> OTHER INFORMATION: Variable heavy chain CDR1
<220> FEATURE:
<221> NAME/KEY: misc_feature
<222> LOCATION: (50)..(69)
<223> OTHER INFORMATION: Variable heavy chain CDR2
<220> FEATURE:
<221> NAME/KEY: misc_feature
<222> LOCATION: (99)..(105)
<223> OTHER INFORMATION: Variable heavy chain CDR3
<220> FEATURE:
<221> NAME/KEY: misc_feature
<222> LOCATION: (133)..(240)
<223> OTHER INFORMATION: Variable light chain
<220> FEATURE:
<221> NAME/KEY: misc_feature
<222> LOCATION: (156)..(166)
<223> OTHER INFORMATION: Variable light chain CDR1
<220> FEATURE:
<221> NAME/KEY: misc_feature
<222> LOCATION: (182)..(188)
<223> OTHER INFORMATION: Variable light chain CDR2
<220> FEATURE:
<221> NAME/KEY: misc_feature
<222> LOCATION: (223)..(229)
<223> OTHER INFORMATION: Variable light chain CDR3
```

-continued

```
<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Gly Leu Ser Gly Gly Gly Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Arg Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asn Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Lys Ala Ser Arg Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Phe Leu
    210                 215                 220

Val Leu Pro Arg Thr Phe Gly Gln Gly Thr Lys Val Glu Ile Lys Arg
225                 230                 235                 240


<210> SEQ ID NO 23
<211> LENGTH: 116
<212> TYPE: PRT
<213> ORGANISM: Artificial Sequence
<220> FEATURE:
<223> OTHER INFORMATION: Description of Artificial Sequence: Synthetic
      clone 3 variable heavy chain polypeptide

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Gly Leu Ser Gly Gly Gly Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Arg Phe Asp Tyr Trp Gly Gln Gly Thr Leu Val
            100                 105                 110
```

Thr Val Ser Ser
115

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic clone 3 variable heavy chain CDR1 peptide

<400> SEQUENCE: 24

Ser Tyr Ala Met Ser
1 5

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic clone 3 variable heavy chain CDR2 peptide

<400> SEQUENCE: 25

Gly Ile Gly Leu Ser Gly Gly Gly Thr Gln Tyr Ala Asp Ser Val Lys
1 5 10 15

Gly Arg Phe Thr
20

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic clone 3 variable heavy chain CDR3 peptide

<400> SEQUENCE: 26

Gly Thr Thr Arg Phe Asp Tyr
1 5

<210> SEQ ID NO 27
<211> LENGTH: 108
<212> TYPE: PRT
<213> ORGANISM: Artificial Sequence
<220> FEATURE:
<223> OTHER INFORMATION: Description of Artificial Sequence: Synthetic clone 3 variable light chain polypeptide

<400> SEQUENCE: 27

Asn Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Lys Ala Ser Arg Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Leu Val Leu Pro Arg
85 90 95

Thr Phe Gly Gln Gly Thr Lys Val Glu Ile Lys Arg
100 105

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic clone 3 variable light chain CDR1 peptide

<400> SEQUENCE: 28

Arg Ala Ser Gln Ser Ile Ser Ser Tyr Leu Asn
1 5 10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic clone 3 variable light chain CDR2 peptide

<400> SEQUENCE: 29

Lys Ala Ser Arg Leu Gln Ser
1 5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic clone 3 variable light chain CDR3 peptide

<400> SEQUENCE: 30

Phe Leu Val Leu Pro Arg Thr
1 5

<210> SEQ ID NO 31
<211> LENGTH: 720
<212> TYPE: DNA
<213> ORGANISM: Artificial Sequence
<220> FEATURE:
<223> OTHER INFORMATION: Description of Artificial Sequence: Synthetic clone 4 polynucleotide

<400> SEQUENCE: 31
gaggtgcagc tgttggagtc tgggggaggc ttggtacagc ctggggggtc cctgagactc 60
tcctgtgcag cctctggatt cacctttagc agctatgcca tgagctgggt ccgccaggct 120
ccagggaagg ggctggagtg ggtctcaagt attaatggtt atggtgataa tacagattac 180
gcagactccg tgaagggcag gttcaccatc tccagagaca attccaagaa cacgctgtat 240
ctgcaaatga acagcctgag agccgaggac acggccgtat attactgtgc gaaaggttct 300
tctgattttg actactgggg ccagggaacc ctggtcaccg tctcgagcgg tggaggcggt 360
tcaggcggag gtggcagcgg cggtggcggg tcgacggaca tccagatgac ccagtctcca 420
tcctccctgt ctgcatctgt aggagacaga gtcaccatca cttgccgggc aagtcagagc 480
attagcagct atttaaattg gtatcagcag aaaccaggga aagcccctaa gctcctgatc 540
tatggtgcat cctctttgca aagtggggtc ccatcaaggt tcagtggcag tggatctggg 600
acagatttca ctctcaccat cagcagtctg caacctgaag attttgcaac ttactactgt 660
caacaggctg gttatgatcc tactacgttc ggccaaggga ccaaggtgga aatcaaacgg 720

```
<210> SEQ ID NO 32
<211> LENGTH: 240
<212> TYPE: PRT
<213> ORGANISM: Artificial Sequence
<220> FEATURE:
<223> OTHER INFORMATION: Description of Artificial Sequence: Synthetic
      clone 4 polypeptide
<220> FEATURE:
<221> NAME/KEY: misc_feature
<222> LOCATION: (1)..(116)
<223> OTHER INFORMATION: Variable heavy chain
<220> FEATURE:
<221> NAME/KEY: misc_feature
<222> LOCATION: (31)..(35)
<223> OTHER INFORMATION: Variable heavy chain CDR1
<220> FEATURE:
<221> NAME/KEY: misc_feature
<222> LOCATION: (50)..(69)
<223> OTHER INFORMATION: Variable heavy chain CDR2
<220> FEATURE:
<221> NAME/KEY: misc_feature
<222> LOCATION: (99)..(105)
<223> OTHER INFORMATION: Variable heavy chain CDR3
<220> FEATURE:
<221> NAME/KEY: misc_feature
<222> LOCATION: (132)..(240)
<223> OTHER INFORMATION: Variable light chain
<220> FEATURE:
<221> NAME/KEY: misc_feature
<222> LOCATION: (156)..(166)
<223> OTHER INFORMATION: Variable light chain CDR1
<220> FEATURE:
<221> NAME/KEY: misc_feature
<222> LOCATION: (182)..(188)
<223> OTHER INFORMATION: Variable light chain CDR2
<220> FEATURE:
<221> NAME/KEY: misc_feature
<222> LOCATION: (223)..(229)
<223> OTHER INFORMATION: Variable light chain CDR3

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asn Gly Tyr Gly Asp Asn Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ser Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Gly Ala Ser Ser Leu Gln Ser Gly Val Pro Ser
            180                 185                 190

Arg Phe Ser Gly Ser Gly Ser Gly Thr Asp Phe Thr Leu Thr Ile Ser
```

```
        195                 200                 205

Ser Leu Gln Pro Glu Asp Phe Ala Thr Tyr Tyr Cys Gln Gln Ala Gly
    210                 215                 220

Tyr Asp Pro Thr Thr Phe Gly Gln Gly Thr Lys Val Glu Ile Lys Arg
225                 230                 235                 240


<210> SEQ ID NO 33
<211> LENGTH: 116
<212> TYPE: PRT
<213> ORGANISM: Artificial Sequence
<220> FEATURE:
<223> OTHER INFORMATION: Description of Artificial Sequence: Synthetic
      clone 4 variable heavy chain polypeptide

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asn Gly Tyr Gly Asp Asn Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ser Asp Phe Asp Tyr Trp Gly Gln Gly Thr Leu Val
            100                 105                 110

Thr Val Ser Ser
        115


<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      clone 4 variable heavy chain CDR1 peptide

<400> SEQUENCE: 34

Ser Tyr Ala Met Ser
1               5


<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic
      clone 4 variable heavy chain CDR2 peptide

<400> SEQUENCE: 35

Ser Ile Asn Gly Tyr Gly Asp Asn Thr Asp Tyr Ala Asp Ser Val Lys
1               5                   10                  15

Gly Arg Phe Thr
            20


<210> SEQ ID NO 36
<211> LENGTH: 7
<212> TYPE: PRT
<213> ORGANISM: Artificial Sequence
```

<220> FEATURE:
<223> OTHER INFORMATION: Description of Artificial Sequence: Synthetic
clone 4 variable heavy chain CDR3 peptide

<400> SEQUENCE: 36

```
Gly Ser Ser Asp Phe Asp Tyr
1               5
```

<210> SEQ ID NO 37
<211> LENGTH: 109
<212> TYPE: PRT
<213> ORGANISM: Artificial Sequence
<220> FEATURE:
<223> OTHER INFORMATION: Description of Artificial Sequence: Synthetic
clone 4 variable light chain polypeptide

<400> SEQUENCE: 37

```
Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Gly Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ala Gly Tyr Asp Pro
                85                  90                  95

Thr Thr Phe Gly Gln Gly Thr Lys Val Glu Ile Lys Arg
            100                 105
```

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
clone 4 variable light chain CDR1 peptide

<400> SEQUENCE: 38

```
Arg Ala Ser Gln Ser Ile Ser Ser Tyr Leu Asn
1               5                   10
```

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
clone 4 variable light chain CDR2 peptide

<400> SEQUENCE: 39

```
Gly Ala Ser Ser Leu Gln Ser
1               5
```

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
clone 4 variable light chain CDR3 peptide

<400> SEQUENCE: 40

```
Ala Gly Tyr Asp Pro Thr Thr
1               5


<210> SEQ ID NO 41
<211> LENGTH: 720
<212> TYPE: DNA
<213> ORGANISM: Artificial Sequence
<220> FEATURE:
<223> OTHER INFORMATION: Description of Artificial Sequence: Synthetic
      clone 5 polynucleotide

<400> SEQUENCE: 41

gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcagct attgctaatg ctggtgctac tacaaattac    180

gcagactccg tgaagggcag gttcaccatc tccagagaca attccaagaa cacgctgtat    240

ctgcaaatga acagcctgag agccgaggac acggccgtat attactgtgc gaaaggtagt    300

agtgattttg actactgggg ccagggaacc ctggtcaccg tctcgagcgg tggaggcggt    360

tcaggcggag gtggcagcgg cggtggcggg tcgacggaca tccagatgac ccagtctcca    420

tcctccctgt ctgcatctgt aggagacaga gtcaccatca cttgccgggc aagtcagagc    480

attagcagct atttaaattg gtatcagcag aaaccaggga aagcccctaa gctcctgatc    540

tatggtgcat ccaatttgca aagtggggtc ccatcaaggt tcagtggcag tggatctggg    600

acagatttca ctctcaccat cagcagtctg caacctgaag attttgcaac ttactactgt    660

caacagagtg gttatgatcc tagtacgttc ggccaaggga ccaaggtgga aatcaaacgg    720


<210> SEQ ID NO 42
<211> LENGTH: 240
<212> TYPE: PRT
<213> ORGANISM: Artificial Sequence
<220> FEATURE:
<223> OTHER INFORMATION: Description of Artificial Sequence: Synthetic
      clone 5 polypeptide
<220> FEATURE:
<221> NAME/KEY: misc_feature
<222> LOCATION: (1)..(116)
<223> OTHER INFORMATION: Variable heavy chain
<220> FEATURE:
<221> NAME/KEY: misc_feature
<222> LOCATION: (31)..(35)
<223> OTHER INFORMATION: Variable heavy chain CDR1
<220> FEATURE:
<221> NAME/KEY: misc_feature
<222> LOCATION: (50)..(69)
<223> OTHER INFORMATION: Variable heavy chain CDR2
<220> FEATURE:
<221> NAME/KEY: misc_feature
<222> LOCATION: (99)..(105)
<223> OTHER INFORMATION: Variable heavy chain CDR3
<220> FEATURE:
<221> NAME/KEY: misc_feature
<222> LOCATION: (132)..(240)
<223> OTHER INFORMATION: Variable light chain
<220> FEATURE:
<221> NAME/KEY: misc_feature
<222> LOCATION: (156)..(166)
<223> OTHER INFORMATION: Variable light chain CDR1
<220> FEATURE:
<221> NAME/KEY: misc_feature
<222> LOCATION: (182)..(188)
<223> OTHER INFORMATION: Variable light chain CDR2
<220> FEATURE:
<221> NAME/KEY: misc_feature
<222> LOCATION: (223)..(229)
<223> OTHER INFORMATION: Variable light chain CDR3
```

<400> SEQUENCE: 42

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ala Asn Ala Gly Ala Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ser Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Gly Ala Ser Asn Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Gly
    210                 215                 220

Tyr Asp Pro Ser Thr Phe Gly Gln Gly Thr Lys Val Glu Ile Lys Arg
225                 230                 235                 240
```

<210> SEQ ID NO 43
<211> LENGTH: 116
<212> TYPE: PRT
<213> ORGANISM: Artificial Sequence
<220> FEATURE:
<223> OTHER INFORMATION: Description of Artificial Sequence: Synthetic clone 5 variable heavy chain polypeptide

<400> SEQUENCE: 43

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ala Asn Ala Gly Ala Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ser Asp Phe Asp Tyr Trp Gly Gln Gly Thr Leu Val
            100                 105                 110
```

```
Thr Val Ser Ser
        115


<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      clone 5 variable heavy chain CDR1 peptide

<400> SEQUENCE: 44

Ser Tyr Ala Met Ser
1               5


<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      clone 5 variable heavy chain CDR2 peptide

<400> SEQUENCE: 45

Ala Ile Ala Asn Ala Gly Ala Thr Thr Asn Tyr Ala Asp Ser Val Lys
1               5                   10                  15

Gly Arg Phe Thr
            20


<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 5 variable heavy chain CDR3 peptide

<400> SEQUENCE: 46

Gly Ser Ser Asp Phe Asp Tyr
1               5


<210> SEQ ID NO 47
<211> LENGTH: 109
<212> TYPE: PRT
<213> ORGANISM: Artificial Sequence
<220> FEATURE:
<223> OTHER INFORMATION: Description of Artificial Sequence: Synthetic
      clone 5 variable light chain polypeptide

<400> SEQUENCE: 47

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Gly Ala Ser Asn Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Gly Tyr Asp Pro
                85                  90                  95

Ser Thr Phe Gly Gln Gly Thr Lys Val Glu Ile Lys Arg
```

100 105

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic clone 5 variable light chain CDR1 peptide

<400> SEQUENCE: 48

Arg Ala Ser Gln Ser Ile Ser Ser Tyr Leu Asn
1 5 10

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic clone 5 variable light chain CDR2 peptide

<400> SEQUENCE: 49

Gly Ala Ser Asn Leu Gln Ser
1 5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic clone 5 variable light chain CDR3 peptide

<400> SEQUENCE: 50

Ser Gly Tyr Asp Pro Ser Thr
1 5

<210> SEQ ID NO 51
<211> LENGTH: 720
<212> TYPE: DNA
<213> ORGANISM: Artificial Sequence
<220> FEATURE:
<223> OTHER INFORMATION: Description of Artificial Sequence: Synthetic clone 9 polynucleotide

<400> SEQUENCE: 51
gaggtgcagc tgttggagtc tgggggaggc ttggtacagc ctggggggtc cctgagactc 60
tcctgtgcag cctctggatt cacctttagc agctatgcca tgagctgggt ccgccaggct 120
ccagggaagg ggctggagtg ggtctcaacg attcaggggc gtggtcatag gacagcgtac 180
gcagactccg tgaagggccg gttcaccatc tccagagaca attccaagaa cacgctgtat 240
ctgcaaatga acagcctgag agccgaggac acggccgtat attactgtgc gaaatcgtcg 300
cttgtttttg actactgggg ccagggaacc ctggtcaccg tctcgagcgg tggaggcggt 360
tcaggcggag gtggcagcgg cggtggcggg tcgacggaca tccagatgac ccagtctcca 420
tcctccctgt ctgcatctgt aggagacaga gtcaccatca cttgccgggc aagtcagagc 480
attagcagct atttaaattg gtatcagcag aaaccaggga aagcccctaa gctcctgatc 540
tataaggcat ccagattgca aagtggggtc ccatcaaggt tcagtggcag tggatctggg 600
acagatttca ctctcaccat cagcagtctg caacctgaag attttgcaac ttactactgt 660
caacagagta tgctgaagcc tccgacgttc ggccaaggga ccaaggtgga aatcaaacgg 720

```
<210> SEQ ID NO 52
<211> LENGTH: 240
<212> TYPE: PRT
<213> ORGANISM: Artificial Sequence
<220> FEATURE:
<223> OTHER INFORMATION: Description of Artificial Sequence: Synthetic
      clone 9 polypeptide
<220> FEATURE:
<221> NAME/KEY: misc_feature
<222> LOCATION: (1)..(116)
<223> OTHER INFORMATION: Variable heavy chain
<220> FEATURE:
<221> NAME/KEY: misc_feature
<222> LOCATION: (31)..(35)
<223> OTHER INFORMATION: Variable heavy chain CDR1
<220> FEATURE:
<221> NAME/KEY: misc_feature
<222> LOCATION: (50)..(69)
<223> OTHER INFORMATION: Variable heavy chain CDR2
<220> FEATURE:
<221> NAME/KEY: misc_feature
<222> LOCATION: (99)..(105)
<223> OTHER INFORMATION: Variable heavy chain CDR3
<220> FEATURE:
<221> NAME/KEY: misc_feature
<222> LOCATION: (132)..(240)
<223> OTHER INFORMATION: Variable light chain
<220> FEATURE:
<221> NAME/KEY: misc_feature
<222> LOCATION: (156)..(166)
<223> OTHER INFORMATION: Variable light chain CDR1
<220> FEATURE:
<221> NAME/KEY: misc_feature
<222> LOCATION: (182)..(188)
<223> OTHER INFORMATION: Variable light chain CDR2
<220> FEATURE:
<221> NAME/KEY: misc_feature
<222> LOCATION: (223)..(229)
<223> OTHER INFORMATION: Variable light chain CDR3

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Gln Gly Arg Gly His Arg Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Leu Val Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Lys Ala Ser Arg Leu Gln Ser Gly Val Pro Ser
            180                 185                 190
```

```
Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Met
    210                 215                 220

Leu Lys Pro Pro Thr Phe Gly Gln Gly Thr Lys Val Glu Ile Lys Arg
225                 230                 235                 240


<210> SEQ ID NO 53
<211> LENGTH: 116
<212> TYPE: PRT
<213> ORGANISM: Artificial Sequence
<220> FEATURE:
<223> OTHER INFORMATION: Description of Artificial Sequence: Synthetic
      clone 9 variable heavy chain polypeptide

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Gln Gly Arg Gly His Arg Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Leu Val Phe Asp Tyr Trp Gly Gln Gly Thr Leu Val
            100                 105                 110

Thr Val Ser Ser
        115


<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      clone 9 variable heavy chain CDR1 peptide

<400> SEQUENCE: 54

Ser Tyr Ala Met Ser
1               5


<210> SEQ ID NO 55
<211> LENGTH: 20
<212> TYPE: PRT
<213> ORGANISM: Artificial Sequence
<220> FEATURE:
<223> OTHER INFORMATION: Description of Artificial Sequence: Synthetic
      clone 9 variable heavy chain CDR2 peptide

<400> SEQUENCE: 55

Thr Ile Gln Gly Arg Gly His Arg Thr Ala Tyr Ala Asp Ser Val Lys
1               5                   10                  15

Gly Arg Phe Thr
            20


<210> SEQ ID NO 56
<211> LENGTH: 7
<212> TYPE: PRT
```

<213> ORGANISM: Artificial Sequence
<220> FEATURE:
<223> OTHER INFORMATION: Description of Artificial Sequence: Synthetic
clone 9 variable heavy chain CDR3 peptide

<400> SEQUENCE: 56

Ser Ser Leu Val Phe Asp Tyr
1 5

<210> SEQ ID NO 57
<211> LENGTH: 109
<212> TYPE: PRT
<213> ORGANISM: Artificial Sequence
<220> FEATURE:
<223> OTHER INFORMATION: Description of Artificial Sequence: Synthetic
clone 9 variable light chain polypeptide

<400> SEQUENCE: 57

Thr Asp Ile Gln Met Thr Gln Ser Pro Ser Ser Leu Ser Ala Ser Val
1 5 10 15

Gly Asp Arg Val Thr Ile Thr Cys Arg Ala Ser Gln Ser Ile Ser Ser
20 25 30

Tyr Leu Asn Trp Tyr Gln Gln Lys Pro Gly Lys Ala Pro Lys Leu Leu
35 40 45

Ile Tyr Lys Ala Ser Arg Leu Gln Ser Gly Val Pro Ser Arg Phe Ser
50 55 60

Gly Ser Gly Ser Gly Thr Asp Phe Thr Leu Thr Ile Ser Ser Leu Gln
65 70 75 80

Pro Glu Asp Phe Ala Thr Tyr Tyr Cys Gln Gln Ser Met Leu Lys Pro
85 90 95

Pro Thr Phe Gly Gln Gly Thr Lys Val Glu Ile Lys Arg
100 105

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
clone 9 variable light chain CDR1 peptide

<400> SEQUENCE: 58

Arg Ala Ser Gln Ser Ile Ser Ser Tyr Leu Asn
1 5 10

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
clone 9 variable light chain CDR2 peptide

<400> SEQUENCE: 59

Lys Ala Ser Arg Leu Gln Ser
1 5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
clone 9 variable light chain CDR3 peptide

<400> SEQUENCE: 60

Ser Met Leu Lys Pro Pro Thr
1               5

<210> SEQ ID NO 61
<211> LENGTH: 720
<212> TYPE: DNA
<213> ORGANISM: Artificial Sequence
<220> FEATURE:
<223> OTHER INFORMATION: Description of Artificial Sequence: Synthetic
      clone 11 polynucleotide

<400> SEQUENCE: 61
gaggtgcagc tgttggagtc tgggggaggc ttggtacagc ctggggggtc cctgagactc     60
tcctgtgcag cctctggatt cacctttagc agctatgcca tgagctgggt ccgccaggct    120
ccagggaagg ggctggagtg ggtctcatct attagtgcta ctggtgctac tacaggttac    180
gcagactccg tgaagggccg gttcaccatc tccagagaca attccaagaa cacgctgtat    240
ctgcaaatga acagcctgag agccgaggac acggccgtat attactgtgc gaaatctggt    300
actgattttg actactgggg ccagggaacc ctggtcaccg tctcgagcgg tggaggcggt    360
tcaggcggag gtggcagcgg cggtggcggg tcgacggaca tccagatgac ccagtctcca    420
tcctccctgt ctgcatctgt aggagacaga gtcaccatca cttgccgggc aagtcagagc    480
attagcagct atttaaattg gtatcagcag aaaccaggga aagcccctaa gctcctgatc    540
tatggtgcat cctatttgca aagtggggtc ccatcaaggt tcagtggcag tggatctggg    600
acagatttca ctctcaccat cagcagtctg caacctgaag attttgcaac ttactactgt    660
caacagagtg gtaatgatcc tactacgttc ggccaaggga ccaaggtgga aatcaaacgg    720

<210> SEQ ID NO 62
<211> LENGTH: 240
<212> TYPE: PRT
<213> ORGANISM: Artificial Sequence
<220> FEATURE:
<223> OTHER INFORMATION: Description of Artificial Sequence: Synthetic
      clone 11 polypeptide
<220> FEATURE:
<221> NAME/KEY: misc_feature
<222> LOCATION: (1)..(116)
<223> OTHER INFORMATION: Variable heavy chain
<220> FEATURE:
<221> NAME/KEY: misc_feature
<222> LOCATION: (31)..(35)
<223> OTHER INFORMATION: Variable heavy chain CDR1
<220> FEATURE:
<221> NAME/KEY: misc_feature
<222> LOCATION: (50)..(69)
<223> OTHER INFORMATION: Variable heavy chain CDR2
<220> FEATURE:
<221> NAME/KEY: misc_feature
<222> LOCATION: (99)..(105)
<223> OTHER INFORMATION: Variable heavy chain CDR3
<220> FEATURE:
<221> NAME/KEY: misc_feature
<222> LOCATION: (132)..(240)
<223> OTHER INFORMATION: Variable light chain
<220> FEATURE:
<221> NAME/KEY: misc_feature
<222> LOCATION: (156)..(166)
<223> OTHER INFORMATION: Variable light chain CDR1
<220> FEATURE:
<221> NAME/KEY: misc_feature
<222> LOCATION: (182)..(188)
<223> OTHER INFORMATION: Variable light chain CDR2
<220> FEATURE:
<221> NAME/KEY: misc_feature
<222> LOCATION: (223)..(229)

```
<223> OTHER INFORMATION: Variable light chain CDR3

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ala Thr Gly Ala Thr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Thr Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Gly Ala Ser Tyr Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Gly
    210                 215                 220

Asn Asp Pro Thr Thr Phe Gly Gln Gly Thr Lys Val Glu Ile Lys Arg
225                 230                 235                 240


<210> SEQ ID NO 63
<211> LENGTH: 116
<212> TYPE: PRT
<213> ORGANISM: Artificial Sequence
<220> FEATURE:
<223> OTHER INFORMATION: Description of Artificial Sequence: Synthetic
      clone 11 variable heavy chain polypeptide

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ala Thr Gly Ala Thr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Thr Asp Phe Asp Tyr Trp Gly Gln Gly Thr Leu Val
```

```
            100                 105                 110

Thr Val Ser Ser
        115


<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      clone 11 variable heavy chain CDR1 peptide

<400> SEQUENCE: 64

Ser Tyr Ala Met Ser
1               5


<210> SEQ ID NO 65
<211> LENGTH: 20
<212> TYPE: PRT
<213> ORGANISM: Artificial Sequence
<220> FEATURE:
<223> OTHER INFORMATION: Description of Artificial Sequence: Synthetic
      clone 11 variable heavy chain CDR2 peptide

<400> SEQUENCE: 65

Ser Ile Ser Ala Thr Gly Ala Thr Thr Gly Tyr Ala Asp Ser Val Lys
1               5                   10                  15

Gly Arg Phe Thr
            20


<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 11 variable heavy chain CDR3 peptide

<400> SEQUENCE: 66

Ser Gly Thr Asp Phe Asp Tyr
1               5


<210> SEQ ID NO 67
<211> LENGTH: 109
<212> TYPE: PRT
<213> ORGANISM: Artificial Sequence
<220> FEATURE:
<223> OTHER INFORMATION: Description of Artificial Sequence: Synthetic
      clone 11 variable light chain polypeptide

<400> SEQUENCE: 67

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Gly Ala Ser Tyr Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Gly Asn Asp Pro
                85                  90                  95
```

```
Thr Thr Phe Gly Gln Gly Thr Lys Val Glu Ile Lys Arg
            100                 105


<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      clone 11 variable light chain CDR1 peptide

<400> SEQUENCE: 68

Arg Ala Ser Gln Ser Ile Ser Ser Tyr Leu Asn
1               5                   10


<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 11 variable light chain CDR2 peptide

<400> SEQUENCE: 69

Gly Ala Ser Tyr Leu Gln Ser
1               5


<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 11 variable light chain CDR3 peptide

<400> SEQUENCE: 70

Ser Gly Asn Asp Pro Thr Thr
1               5


<210> SEQ ID NO 71
<211> LENGTH: 720
<212> TYPE: DNA
<213> ORGANISM: Artificial Sequence
<220> FEATURE:
<223> OTHER INFORMATION: Description of Artificial Sequence: Synthetic
      clone 13 polynucleotide

<400> SEQUENCE: 71

gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcatct atttatccgc agggtctgcg gacatattac    180

gcagactccg tgaagggccg gttcaccatc tccagagaca attccaagaa cacgctgtat    240

ctgcaaatga acagcctgag agccgaggac acggccgtat attactgtgc gaaaaatctt    300

gctaagtttg actactgggg ccagggaacc ctggtcaccg tctcgagcgg tggaggcggt    360

tcaggcggag gtggcagcgg cggtggcggg tcgacggaca tccagatgac ccagtctcca    420

tcctccctgt ctgcatctgt aggagacaga gtcaccatca cttgccgggc aagtcagagc    480

attagcagct atttaaattg gtatcagcag aaaccaggga aagcccctaa gctcctgatc    540

tatagggcat ccactttgca aagtggggtc ccatcaaggt tcagtggcag tggatctggg    600

acagatttca ctctcaccat cagcagtctg caacctgaag attttgcaac ttactactgt    660

caacagcctc gggcgcttcc tggtacgttc ggccaaggga ccaaggtgga aatcaaacgg    720
```

<210> SEQ ID NO 72
<211> LENGTH: 240
<212> TYPE: PRT
<213> ORGANISM: Artificial Sequence
<220> FEATURE:
<223> OTHER INFORMATION: Description of Artificial Sequence: Synthetic clone 13 polypeptide
<220> FEATURE:
<221> NAME/KEY: misc_feature
<222> LOCATION: (1)..(116)
<223> OTHER INFORMATION: Variable heavy chain
<220> FEATURE:
<221> NAME/KEY: misc_feature
<222> LOCATION: (31)..(35)
<223> OTHER INFORMATION: Variable heavy chain CDR1
<220> FEATURE:
<221> NAME/KEY: misc_feature
<222> LOCATION: (50)..(69)
<223> OTHER INFORMATION: Variable heavy chain CDR2
<220> FEATURE:
<221> NAME/KEY: misc_feature
<222> LOCATION: (99)..(105)
<223> OTHER INFORMATION: Variable heavy chain CDR3
<220> FEATURE:
<221> NAME/KEY: misc_feature
<222> LOCATION: (132)..(240)
<223> OTHER INFORMATION: Variable light chain
<220> FEATURE:
<221> NAME/KEY: misc_feature
<222> LOCATION: (156)..(166)
<223> OTHER INFORMATION: Variable light chain CDR1
<220> FEATURE:
<221> NAME/KEY: misc_feature
<222> LOCATION: (182)..(188)
<223> OTHER INFORMATION: Variable light chain CDR2
<220> FEATURE:
<221> NAME/KEY: misc_feature
<222> LOCATION: (223)..(229)
<223> OTHER INFORMATION: Variable light chain CDR3

<400> SEQUENCE: 72

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Tyr Pro Gln Gly Leu Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Ala Lys Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Arg Ala Ser Thr Leu Gln Ser Gly Val Pro Ser
            180                 185                 190
```

```
Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Pro Arg
    210                 215                 220

Ala Leu Pro Gly Thr Phe Gly Gln Gly Thr Lys Val Glu Ile Lys Arg
225                 230                 235                 240


<210> SEQ ID NO 73
<211> LENGTH: 116
<212> TYPE: PRT
<213> ORGANISM: Artificial Sequence
<220> FEATURE:
<223> OTHER INFORMATION: Description of Artificial Sequence: Synthetic
      clone 13 variable heavy chain polypeptide

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Tyr Pro Gln Gly Leu Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Ala Lys Phe Asp Tyr Trp Gly Gln Gly Thr Leu Val
            100                 105                 110

Thr Val Ser Ser
        115


<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      clone 13 variable heavy chain CDR1 peptide

<400> SEQUENCE: 74

Ser Tyr Ala Met Ser
1               5


<210> SEQ ID NO 75
<211> LENGTH: 20
<212> TYPE: PRT
<213> ORGANISM: Artificial Sequence
<220> FEATURE:
<223> OTHER INFORMATION: Description of Artificial Sequence: Synthetic
      clone 13 variable heavy chain CDR2 peptide

<400> SEQUENCE: 75

Ser Ile Tyr Pro Gln Gly Leu Arg Thr Tyr Tyr Ala Asp Ser Val Lys
1               5                   10                  15

Gly Arg Phe Thr
            20


<210> SEQ ID NO 76
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      clone 13 variable heavy chain CDR3 peptide

<400> SEQUENCE: 76

Asn Leu Ala Lys Phe Asp Tyr
1               5


<210> SEQ ID NO 77
<211> LENGTH: 109
<212> TYPE: PRT
<213> ORGANISM: Artificial Sequence
<220> FEATURE:
<223> OTHER INFORMATION: Description of Artificial Sequence: Synthetic
      clone 13 variable light chain polypeptide

<400> SEQUENCE: 77

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Arg Ala Ser Thr Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Pro Arg Ala Leu Pro
                85                  90                  95

Gly Thr Phe Gly Gln Gly Thr Lys Val Glu Ile Lys Arg
            100                 105


<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      clone 13 variable light chain CDR1 peptide

<400> SEQUENCE: 78

Arg Ala Ser Gln Ser Ile Ser Ser Tyr Leu Asn
1               5                   10


<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 13 variable light chain CDR2 peptide

<400> SEQUENCE: 79

Arg Ala Ser Thr Leu Gln Ser
1               5


<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 13 variable light chain CDR3 peptide
```

<400> SEQUENCE: 80

Pro Arg Ala Leu Pro Gly Thr
1 5

<210> SEQ ID NO 81
<211> LENGTH: 720
<212> TYPE: DNA
<213> ORGANISM: Artificial Sequence
<220> FEATURE:
<223> OTHER INFORMATION: Description of Artificial Sequence: Synthetic
clone 16 polynucleotide

<400> SEQUENCE: 81

```
gaggtgcagc tgttggagtc tgggggaggc ttggtacagc ctggggggtc cctgagactc     60
tcctgtgcag cctctggatt cacctttagc agctatgcca tgagctgggt ccgccaggct    120
ccagggaagg ggctggagtg ggtctcacgg attactggtt ctggtggtca gacaacttac    180
gcagactccg tgaagggccg gttcaccatc tccagagaca attccaagaa cacgctgtat    240
ctgcaaatga acagcctgag agccgaggac acggccgtat attactgtgc gaaaggtatg    300
cgtcagtttg actactgggg ccagggaacc ctggtcaccg tctcgagcgg tggaggcggt    360
tcaggcggag gtggcagcgg cggtggcggg tcgacggaca tccagatgac ccagtctcca    420
tcctccctgt ctgcatctgt aggagacaga gtcaccatca cttgccgggc aagtcagagc    480
attagcagct atttaaattg gtatcagcag aaaccaggga aagcccctaa gctcctgatt    540
tatcgtgcat cctctttgca aagtggggtc ccatcaaggt tcagtggcag tggatctggg    600
acagatttca ctctcaccat cagcagtctg caacctgaag attttgcaac ttactactgt    660
caacaggcgc gtgtgccgcc tactacgttc ggccaaggga ccaaggtgga aatcaaacgg    720
```

<210> SEQ ID NO 82
<211> LENGTH: 240
<212> TYPE: PRT
<213> ORGANISM: Artificial Sequence
<220> FEATURE:
<223> OTHER INFORMATION: Description of Artificial Sequence: Synthetic
clone 16 polypeptide
<220> FEATURE:
<221> NAME/KEY: misc_feature
<222> LOCATION: (1)..(116)
<223> OTHER INFORMATION: Variable heavy chain
<220> FEATURE:
<221> NAME/KEY: misc_feature
<222> LOCATION: (31)..(35)
<223> OTHER INFORMATION: Variable heavy chain CDR1
<220> FEATURE:
<221> NAME/KEY: misc_feature
<222> LOCATION: (50)..(69)
<223> OTHER INFORMATION: Variable heavy chain CDR2
<220> FEATURE:
<221> NAME/KEY: misc_feature
<222> LOCATION: (99)..(105)
<223> OTHER INFORMATION: Variable heavy chain CDR3
<220> FEATURE:
<221> NAME/KEY: misc_feature
<222> LOCATION: (132)..(240)
<223> OTHER INFORMATION: Variable light chain
<220> FEATURE:
<221> NAME/KEY: misc_feature
<222> LOCATION: (156)..(166)
<223> OTHER INFORMATION: Variable light chain CDR1
<220> FEATURE:
<221> NAME/KEY: misc_feature
<222> LOCATION: (182)..(188)
<223> OTHER INFORMATION: Variable light chain CDR2
<220> FEATURE:
<221> NAME/KEY: misc_feature

```
<222> LOCATION: (223)..(229)
<223> OTHER INFORMATION: Variable light chain CDR3

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Thr Gly Ser Gly Gly Gln Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Met Arg Gln Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Arg Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ala Arg
    210                 215                 220

Val Pro Pro Thr Thr Phe Gly Gln Gly Thr Lys Val Glu Ile Lys Arg
225                 230                 235                 240


<210> SEQ ID NO 83
<211> LENGTH: 116
<212> TYPE: PRT
<213> ORGANISM: Artificial Sequence
<220> FEATURE:
<223> OTHER INFORMATION: Description of Artificial Sequence: Synthetic
      clone 16 variable heavy chain polypeptide

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Thr Gly Ser Gly Gly Gln Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Gly Met Arg Gln Phe Asp Tyr Trp Gly Gln Gly Thr Leu Val
            100                 105                 110

Thr Val Ser Ser
        115


<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
      clone 16 variable heavy chain CDR1 peptide

<400> SEQUENCE: 84

Ser Tyr Ala Met Ser
1               5


<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence: Synthetic
      clone 16 variable heavy chain CDR2 peptide

<400> SEQUENCE: 85

Arg Ile Thr Gly Ser Gly Gly Gln Thr Thr Tyr Ala Asp Ser Val Lys
1               5                   10                  15

Gly Arg Phe Thr
            20


<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 16 variable heavy chain CDR3 peptide

<400> SEQUENCE: 86

Gly Met Arg Gln Phe Asp Tyr
1               5


<210> SEQ ID NO 87
<211> LENGTH: 109
<212> TYPE: PRT
<213> ORGANISM: Artificial Sequence
<220> FEATURE:
<223> OTHER INFORMATION: Description of Artificial Sequence: Synthetic
      clone 16 variable light chain polypeptide

<400> SEQUENCE: 87

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Arg Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ala Arg Val Pro Pro
                85                  90                  95
```

```
Thr Thr Phe Gly Gln Gly Thr Lys Val Glu Ile Lys Arg
            100                 105


<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      clone 16 variable light chain CDR1 peptide

<400> SEQUENCE: 88

Arg Ala Ser Gln Ser Ile Ser Ser Tyr Leu Asn
1               5                   10


<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 16 variable light chain CDR2 peptide

<400> SEQUENCE: 89

Arg Ala Ser Ser Leu Gln Ser
1               5


<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 16 variable light chain CDR3 peptide

<400> SEQUENCE: 90

Ala Arg Val Pro Pro Thr Thr
1               5


<210> SEQ ID NO 91
<211> LENGTH: 720
<212> TYPE: DNA
<213> ORGANISM: Artificial Sequence
<220> FEATURE:
<223> OTHER INFORMATION: Description of Artificial Sequence: Synthetic
      clone 17 polynucleotide

<400> SEQUENCE: 91

gaggtgcagc tgttggagtc tgggggaggc ttggtacagc ctggggggtc cctgagactc      60

tcctgtgcag cctctggatt cacctttagc agctatgcca tgagctgggt ccgccaggct     120

ccagggaagg ggctggagtg ggtctcatcg attctgggtt atggtaggca gacaatgtac     180

gcagactccg tgaagggccg gttcaccatc tccagagaca attccaagaa cacgctgtat     240

ctgcaaatga acagcctgag agccgaggac acggccgtat attactgtgc gaaatggtat     300

cgtgcttttg actactgggg ccagggaacc ctggtcaccg tctcgagcgg tggaggcggt     360

tcaggcggag gtggcagcgg cggtggcggg tcgacggaca tccagatgac ccagtctcca     420

tcctccctgt ctgcatctgt aggagacaga gtcaccatca cttgccgggc aagtcagagc     480

attagcagct atttaaattg gtatcagcag aaaccaggga aagcccctaa gctcctgatc     540

tatgctgcat ccagtttgca aagtggggtc ccatcaaggt tcagtggcag tggatctggg     600

acagatttca ctctcaccat cagcagtctg caacctgaag attttgcaac ttactactgt     660
```

```
caacagagtt acagtacccc taatacgttc ggccaaggga ccaaggtgga aatcaaacgg    720


<210> SEQ ID NO 92
<211> LENGTH: 240
<212> TYPE: PRT
<213> ORGANISM: Artificial Sequence
<220> FEATURE:
<223> OTHER INFORMATION: Description of Artificial Sequence: Synthetic
      clone 17 polypeptide
<220> FEATURE:
<221> NAME/KEY: misc_feature
<222> LOCATION: (1)..(116)
<223> OTHER INFORMATION: Variable heavy chain
<220> FEATURE:
<221> NAME/KEY: misc_feature
<222> LOCATION: (31)..(35)
<223> OTHER INFORMATION: Variable heavy chain CDR1
<220> FEATURE:
<221> NAME/KEY: misc_feature
<222> LOCATION: (50)..(69)
<223> OTHER INFORMATION: Variable heavy chain CDR2
<220> FEATURE:
<221> NAME/KEY: misc_feature
<222> LOCATION: (99)..(105)
<223> OTHER INFORMATION: Variable heavy chain CDR3
<220> FEATURE:
<221> NAME/KEY: misc_feature
<222> LOCATION: (132)..(240)
<223> OTHER INFORMATION: Variable light chain
<220> FEATURE:
<221> NAME/KEY: misc_feature
<222> LOCATION: (156)..(166)
<223> OTHER INFORMATION: Variable light chain CDR1
<220> FEATURE:
<221> NAME/KEY: misc_feature
<222> LOCATION: (182)..(188)
<223> OTHER INFORMATION: Variable light chain CDR2
<220> FEATURE:
<221> NAME/KEY: misc_feature
<222> LOCATION: (223)..(229)
<223> OTHER INFORMATION: Variable light chain CDR3

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Leu Gly Tyr Gly Arg Gln Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Tyr Arg Ala Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
```

```
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Tyr
    210                 215                 220

Ser Thr Pro Asn Thr Phe Gly Gln Gly Thr Lys Val Glu Ile Lys Arg
225                 230                 235                 240


<210> SEQ ID NO 93
<211> LENGTH: 116
<212> TYPE: PRT
<213> ORGANISM: Artificial Sequence
<220> FEATURE:
<223> OTHER INFORMATION: Description of Artificial Sequence: Synthetic
      clone 17 variable heavy chain polypeptide

<400> SEQUENCE: 93

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Leu Gly Tyr Gly Arg Gln Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Tyr Arg Ala Phe Asp Tyr Trp Gly Gln Gly Thr Leu Val
            100                 105                 110

Thr Val Ser Ser
        115


<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      clone 17 variable heavy chain CDR1 peptide

<400> SEQUENCE: 94

Ser Tyr Ala Met Ser
1               5


<210> SEQ ID NO 95
<211> LENGTH: 20
<212> TYPE: PRT
<213> ORGANISM: Artificial Sequence
<220> FEATURE:
<223> OTHER INFORMATION: Description of Artificial Sequence: Synthetic
      clone 17 variable heavy chain CDR2 peptide

<400> SEQUENCE: 95

Ser Ile Leu Gly Tyr Gly Arg Gln Thr Met Tyr Ala Asp Ser Val Lys
1               5                   10                  15

Gly Arg Phe Thr
            20


<210> SEQ ID NO 96
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 17 variable heavy chain CDR3 peptide

<400> SEQUENCE: 96

Trp Tyr Arg Ala Phe Asp Tyr
1               5


<210> SEQ ID NO 97
<211> LENGTH: 109
<212> TYPE: PRT
<213> ORGANISM: Artificial Sequence
<220> FEATURE:
<223> OTHER INFORMATION: Description of Artificial Sequence: Synthetic
      clone 17 variable light chain polypeptide

<400> SEQUENCE: 97

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
                85                  90                  95

Asn Thr Phe Gly Gln Gly Thr Lys Val Glu Ile Lys Arg
            100                 105


<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      clone 17 variable light chain CDR1 peptide

<400> SEQUENCE: 98

Arg Ala Ser Gln Ser Ile Ser Ser Tyr Leu Asn
1               5                   10


<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 17 variable light chain CDR2 peptide

<400> SEQUENCE: 99

Ala Ala Ser Ser Leu Gln Ser
1               5


<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
```

clone 17 variable light chain CDR3 peptide

<400> SEQUENCE: 100

Ser Tyr Ser Thr Pro Asn Thr
1 5

<210> SEQ ID NO 101
<211> LENGTH: 720
<212> TYPE: DNA
<213> ORGANISM: Artificial Sequence
<220> FEATURE:
<223> OTHER INFORMATION: Description of Artificial Sequence: Synthetic clone 18 polynucleotide

<400> SEQUENCE: 101

```
gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcaacg attcataaga cgggttcgcc gacatattac    180

gcagactccg tgaagggccg gttcaccatc tccagagaca attccaagaa cacgctgtat    240

ctgcaaatga acagcctgag agccgaggac acggccgtat attactgtgc gaagtctttg    300

aagtattttg actactgggg ccagggaacc ctggtcaccg tctcgagcgg tggaggcggt    360

tcaggcggag gtggcagcgg cggtggcggg tcgacggaca tccagatgac ccagtctcca    420

tcctccctgt ctgcatctgt aggagacaga gtcaccatca cttgccgggc aagtcagagc    480

attagcagct atttaaattg gtatcagcag aaaccaggga aagcccctaa gctcctgatc    540

tatagggcat cccatttgca aagtggggtc ccatcaaggt tcagtggcag tggatctggg    600

acagatttca ctctcaccat cagcagtctg caacctgaag attttgcaac ttactactgt    660

caacagccgc ggagtctgcc tgctacgttc ggccaaggga ccaaggtgga aatcaaacgg    720
```

<210> SEQ ID NO 102
<211> LENGTH: 240
<212> TYPE: PRT
<213> ORGANISM: Artificial Sequence
<220> FEATURE:
<223> OTHER INFORMATION: Description of Artificial Sequence: Synthetic clone 18 polypeptide
<220> FEATURE:
<221> NAME/KEY: misc_feature
<222> LOCATION: (1)..(116)
<223> OTHER INFORMATION: Variable heavy chain
<220> FEATURE:
<221> NAME/KEY: misc_feature
<222> LOCATION: (31)..(35)
<223> OTHER INFORMATION: Variable heavy chain CDR1
<220> FEATURE:
<221> NAME/KEY: misc_feature
<222> LOCATION: (50)..(69)
<223> OTHER INFORMATION: Variable heavy chain CDR2
<220> FEATURE:
<221> NAME/KEY: misc_feature
<222> LOCATION: (99)..(105)
<223> OTHER INFORMATION: Variable heavy chain CDR3
<220> FEATURE:
<221> NAME/KEY: misc_feature
<222> LOCATION: (132)..(240)
<223> OTHER INFORMATION: Variable light chain
<220> FEATURE:
<221> NAME/KEY: misc_feature
<222> LOCATION: (156)..(166)
<223> OTHER INFORMATION: Variable light chain CDR1
<220> FEATURE:
<221> NAME/KEY: misc_feature
<222> LOCATION: (182)..(188)
<223> OTHER INFORMATION: Variable light chain CDR2
<220> FEATURE:

```
<221> NAME/KEY: misc_feature
<222> LOCATION: (223)..(229)
<223> OTHER INFORMATION: Variable light chain CDR3

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile His Lys Thr Gly Ser Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Leu Lys Tyr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Arg Ala Ser His Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Pro Arg
    210                 215                 220

Ser Leu Pro Ala Thr Phe Gly Gln Gly Thr Lys Val Glu Ile Lys Arg
225                 230                 235                 240


<210> SEQ ID NO 103
<211> LENGTH: 116
<212> TYPE: PRT
<213> ORGANISM: Artificial Sequence
<220> FEATURE:
<223> OTHER INFORMATION: Description of Artificial Sequence: Synthetic
      clone 18 variable heavy chain polypeptide

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile His Lys Thr Gly Ser Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Ser Leu Lys Tyr Phe Asp Tyr Trp Gly Gln Gly Thr Leu Val
            100                 105                 110

Thr Val Ser Ser
        115


<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      clone 18 variable heavy chain CDR1 peptide

<400> SEQUENCE: 104

Ser Tyr Ala Met Ser
1               5


<210> SEQ ID NO 105
<211> LENGTH: 20
<212> TYPE: PRT
<213> ORGANISM: Artificial Sequence
<220> FEATURE:
<223> OTHER INFORMATION: Description of Artificial Sequence: Synthetic
      clone 18 variable heavy chain CDR2 peptide

<400> SEQUENCE: 105

Thr Ile His Lys Thr Gly Ser Pro Thr Tyr Tyr Ala Asp Ser Val Lys
1               5                   10                  15

Gly Arg Phe Thr
            20


<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 18 variable heavy chain CDR3 peptide

<400> SEQUENCE: 106

Ser Leu Lys Tyr Phe Asp Tyr
1               5


<210> SEQ ID NO 107
<211> LENGTH: 109
<212> TYPE: PRT
<213> ORGANISM: Artificial Sequence
<220> FEATURE:
<223> OTHER INFORMATION: Description of Artificial Sequence: Synthetic
      clone 18 variable light chain polypeptide

<400> SEQUENCE: 107

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Arg Ala Ser His Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Pro Arg Ser Leu Pro
```

```
              85                  90                  95

Ala Thr Phe Gly Gln Gly Thr Lys Val Glu Ile Lys Arg
            100                 105


<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      clone 18 variable light chain CDR1 peptide

<400> SEQUENCE: 108

Arg Ala Ser Gln Ser Ile Ser Ser Tyr Leu Asn
1               5                   10


<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 18 variable light chain CDR2 peptide

<400> SEQUENCE: 109

Arg Ala Ser His Leu Gln Ser
1               5


<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 18 variable light chain CDR3 peptide

<400> SEQUENCE: 110

Pro Arg Ser Leu Pro Ala Thr
1               5


<210> SEQ ID NO 111
<211> LENGTH: 720
<212> TYPE: DNA
<213> ORGANISM: Artificial Sequence
<220> FEATURE:
<223> OTHER INFORMATION: Description of Artificial Sequence: Synthetic
      clone 21 polynucleotide

<400> SEQUENCE: 111

gaggtgcagc tgttggagtc tgggggaggc ttggtacagc ctggggggtc cctgagactc      60

tcctgtgcag cctctggatt cacctttagc agctatgcca tgagctgggt ccgccaggct     120

ccagggaagg ggctggagtg ggtctcaact atttatcgtg cgggtcagaa tacaaggtac     180

gcagactccg tgaagggccg gttcaccatc tccagagaca attccaagaa cacgctgtat     240

ctgcaaatga acagcctgag agccgaggac acggccgtat attactgtgc gaaatcgagt     300

cggacttttg actactgggg ccagggaacc ctggtcaccg tctcgagcgg tggaggcggt     360

tcaggcggag gtggcagcgg cggtggcggg tcgacggaca tccagatgac ccagtctcca     420

tcctccctgt ctgcatctgt aggagacaga gtcaccatca cttgccgggc aagtcagagc     480

attagcagct atttaaattg gtatcagcag aaaccaggga aagcccctaa gctcctgatc     540

tataaggcat cctcgttgca aagtggggtc ccatcaaggt tcagtggcag tggatctggg     600

acagatttca ctctcaccat cagcagtctg caacctgaag attttgcaac ttactactgt     660
```

```
caacaggcga cgctgcagcc tcggacgttc ggccaaggga ccaaggtgga aatcaaacgg    720


<210> SEQ ID NO 112
<211> LENGTH: 240
<212> TYPE: PRT
<213> ORGANISM: Artificial Sequence
<220> FEATURE:
<223> OTHER INFORMATION: Description of Artificial Sequence: Synthetic
      clone 21 polypeptide
<220> FEATURE:
<221> NAME/KEY: misc_feature
<222> LOCATION: (1)..(116)
<223> OTHER INFORMATION: Variable heavy chain
<220> FEATURE:
<221> NAME/KEY: misc_feature
<222> LOCATION: (31)..(35)
<223> OTHER INFORMATION: Variable heavy chain CDR1
<220> FEATURE:
<221> NAME/KEY: misc_feature
<222> LOCATION: (50)..(69)
<223> OTHER INFORMATION: Variable heavy chain CDR2
<220> FEATURE:
<221> NAME/KEY: misc_feature
<222> LOCATION: (99)..(105)
<223> OTHER INFORMATION: Variable heavy chain CDR3
<220> FEATURE:
<221> NAME/KEY: misc_feature
<222> LOCATION: (132)..(240)
<223> OTHER INFORMATION: Variable light chain
<220> FEATURE:
<221> NAME/KEY: misc_feature
<222> LOCATION: (156)..(166)
<223> OTHER INFORMATION: Variable light chain CDR1
<220> FEATURE:
<221> NAME/KEY: misc_feature
<222> LOCATION: (182)..(188)
<223> OTHER INFORMATION: Variable light chain CDR2
<220> FEATURE:
<221> NAME/KEY: misc_feature
<222> LOCATION: (223)..(229)
<223> OTHER INFORMATION: Variable light chain CDR3

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Tyr Arg Ala Gly Gln Asn Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Arg Thr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175
```

```
Lys Leu Leu Ile Tyr Lys Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ala Thr
    210                 215                 220

Leu Gln Pro Arg Thr Phe Gly Gln Gly Thr Lys Val Glu Ile Lys Arg
225                 230                 235                 240


<210> SEQ ID NO 113
<211> LENGTH: 116
<212> TYPE: PRT
<213> ORGANISM: Artificial Sequence
<220> FEATURE:
<223> OTHER INFORMATION: Description of Artificial Sequence: Synthetic
      clone 21 variable heavy chain polypeptide

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Tyr Arg Ala Gly Gln Asn Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Arg Thr Phe Asp Tyr Trp Gly Gln Gly Thr Leu Val
            100                 105                 110

Thr Val Ser Ser
        115


<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
      clone 21 variable heavy chain CDR1 peptide

<400> SEQUENCE: 114

Ser Tyr Ala Met Ser
1               5


<210> SEQ ID NO 115
<211> LENGTH: 20
<212> TYPE: PRT
<213> ORGANISM: Artificial Sequence
<220> FEATURE:
<223> OTHER INFORMATION: Description of Artificial Sequence: Synthetic
      clone 21 variable heavy chain CDR2 peptide

<400> SEQUENCE: 115

Thr Ile Tyr Arg Ala Gly Gln Asn Thr Arg Tyr Ala Asp Ser Val Lys
1               5                   10                  15

Gly Arg Phe Thr
            20
```

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic clone 21 variable heavy chain CDR3 peptide

<400> SEQUENCE: 116

Ser Ser Arg Thr Phe Asp Tyr
1 5

<210> SEQ ID NO 117
<211> LENGTH: 109
<212> TYPE: PRT
<213> ORGANISM: Artificial Sequence
<220> FEATURE:
<223> OTHER INFORMATION: Description of Artificial Sequence: Synthetic clone 21 variable light chain polypeptide

<400> SEQUENCE: 117

Thr Asp Ile Gln Met Thr Gln Ser Pro Ser Ser Leu Ser Ala Ser Val
1 5 10 15

Gly Asp Arg Val Thr Ile Thr Cys Arg Ala Ser Gln Ser Ile Ser Ser
20 25 30

Tyr Leu Asn Trp Tyr Gln Gln Lys Pro Gly Lys Ala Pro Lys Leu Leu
35 40 45

Ile Tyr Lys Ala Ser Ser Leu Gln Ser Gly Val Pro Ser Arg Phe Ser
50 55 60

Gly Ser Gly Ser Gly Thr Asp Phe Thr Leu Thr Ile Ser Ser Leu Gln
65 70 75 80

Pro Glu Asp Phe Ala Thr Tyr Tyr Cys Gln Gln Ala Thr Leu Gln Pro
85 90 95

Arg Thr Phe Gly Gln Gly Thr Lys Val Glu Ile Lys Arg
100 105

<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence: Synthetic clone 21 variable light chain CDR1 peptide

<400> SEQUENCE: 118

Arg Ala Ser Gln Ser Ile Ser Ser Tyr Leu Asn
1 5 10

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic clone 21 variable light chain CDR2 peptide

<400> SEQUENCE: 119

Lys Ala Ser Ser Leu Gln Ser
1 5

<210> SEQ ID NO 120
<211> LENGTH: 7
<212> TYPE: PRT
<213> ORGANISM: Artificial Sequence
<220> FEATURE:

<223> OTHER INFORMATION: Description of Artificial Sequence: Synthetic
      clone 21 variable light chain CDR3 peptide

<400> SEQUENCE: 120

Ala Thr Leu Gln Pro Arg Thr
1               5

<210> SEQ ID NO 121
<211> LENGTH: 720
<212> TYPE: DNA
<213> ORGANISM: Artificial Sequence
<220> FEATURE:
<223> OTHER INFORMATION: Description of Artificial Sequence: Synthetic
      clone 23 polynucleotide

<400> SEQUENCE: 121
gaggtgcagc tgttggagtc tgggggaggc ttggtacagc ctggggggtc cctgagactc 60
tcctgtgcag cctctggatt cacctttagc agctatgcca tgagctgggt ccgccaggct 120
ccagggaagg ggctggagtg ggtctcatct attagtgctt ctggtacttc tacaaattac 180
gcagactccg tgaagggccg gttcaccatc tccagagaca attccaagaa cacgctgtat 240
ctgcaaatga acagcctgag agccgaggac acggccgtat attactgtgc gaaaagtaat 300
agtgattttg actactgggg ccagggaacc ctggtcaccg tctcgagcgg tggaggcggt 360
tcaggcggag gtggcagcgg cggtggcggg tcgacggaca tccagatgac ccagtctcca 420
tcctccctgt ctgcatctgt aggagacaga gtcaccatca cttgccgggc aagtcagagc 480
attagcagct atttaaattg gtatcagcag aaaccaggga aagcccctaa gctcctgatc 540
tatggtgcat cctatttgca aagtggggtc ccatcaaggt tcagtggcag tggatctggg 600
acagatttca ctctcaccat cagcagtctg caacctgaag attttgcaac ttactactgt 660
caacagtctg gttatgatcc tgctacgttc ggccaaggga ccaaggtgga aatcaaacgg 720

<210> SEQ ID NO 122
<211> LENGTH: 240
<212> TYPE: PRT
<213> ORGANISM: Artificial Sequence
<220> FEATURE:
<223> OTHER INFORMATION: Description of Artificial Sequence: Synthetic
      clone 23 polypeptide
<220> FEATURE:
<221> NAME/KEY: misc_feature
<222> LOCATION: (1)..(116)
<223> OTHER INFORMATION: Variable heavy chain
<220> FEATURE:
<221> NAME/KEY: misc_feature
<222> LOCATION: (31)..(35)
<223> OTHER INFORMATION: Variable heavy chain CDR1
<220> FEATURE:
<221> NAME/KEY: misc_feature
<222> LOCATION: (50)..(69)
<223> OTHER INFORMATION: Variable heavy chain CDR2
<220> FEATURE:
<221> NAME/KEY: misc_feature
<222> LOCATION: (99)..(105)
<223> OTHER INFORMATION: Variable heavy chain CDR3
<220> FEATURE:
<221> NAME/KEY: misc_feature
<222> LOCATION: (132)..(240)
<223> OTHER INFORMATION: Variable light chain
<220> FEATURE:
<221> NAME/KEY: misc_feature
<222> LOCATION: (156)..(166)
<223> OTHER INFORMATION: Variable light chain CDR1
<220> FEATURE:
<221> NAME/KEY: misc_feature
<222> LOCATION: (182)..(188)
<223> OTHER INFORMATION: Variable light chain CDR2

```
<220> FEATURE:
<221> NAME/KEY: misc_feature
<222> LOCATION: (223)..(229)
<223> OTHER INFORMATION: Variable light chain CDR3

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ala Ser Gly Thr Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Asn Ser Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Gly Ala Ser Tyr Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Gly
    210                 215                 220

Tyr Asp Pro Ala Thr Phe Gly Gln Gly Thr Lys Val Glu Ile Lys Arg
225                 230                 235                 240


<210> SEQ ID NO 123
<211> LENGTH: 116
<212> TYPE: PRT
<213> ORGANISM: Artificial Sequence
<220> FEATURE:
<223> OTHER INFORMATION: Description of Artificial Sequence: Synthetic
      clone 23 variable heavy chain polypeptide

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ala Ser Gly Thr Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95

Ala Lys Ser Asn Ser Asp Phe Asp Tyr Trp Gly Gln Gly Thr Leu Val
            100                 105                 110

Thr Val Ser Ser
        115


<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      clone 23 variable heavy chain CDR1 peptide

<400> SEQUENCE: 124

Ser Tyr Ala Met Ser
1               5


<210> SEQ ID NO 125
<211> LENGTH: 20
<212> TYPE: PRT
<213> ORGANISM: Artificial Sequence
<220> FEATURE:
<223> OTHER INFORMATION: Description of Artificial Sequence: Synthetic
      clone 23 variable heavy chain CDR2 peptide

<400> SEQUENCE: 125

Ser Ile Ser Ala Ser Gly Thr Ser Thr Asn Tyr Ala Asp Ser Val Lys
1               5                   10                  15

Gly Arg Phe Thr
            20


<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 23 variable heavy chain CDR3 peptide

<400> SEQUENCE: 126

Ser Asn Ser Asp Phe Asp Tyr
1               5


<210> SEQ ID NO 127
<211> LENGTH: 109
<212> TYPE: PRT
<213> ORGANISM: Artificial Sequence
<220> FEATURE:
<223> OTHER INFORMATION: Description of Artificial Sequence: Synthetic
      clone 23 variable light chain polypeptide

<400> SEQUENCE: 127

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Gly Ala Ser Tyr Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80
```

```
Pro Glu Asp Phe Ala Thr Tyr Tyr Cys Gln Gln Ser Gly Tyr Asp Pro
                85                  90                  95

Ala Thr Phe Gly Gln Gly Thr Lys Val Glu Ile Lys Arg
            100                 105


<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      clone 23 variable light chain CDR1 peptide

<400> SEQUENCE: 128

Arg Ala Ser Gln Ser Ile Ser Ser Tyr Leu Asn
1               5                   10


<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 23 variable light chain CDR2 peptide

<400> SEQUENCE: 129

Gly Ala Ser Tyr Leu Gln Ser
1               5


<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 23 variable light chain CDR3 peptide

<400> SEQUENCE: 130

Ser Gly Tyr Asp Pro Ala Thr
1               5


<210> SEQ ID NO 131
<211> LENGTH: 720
<212> TYPE: DNA
<213> ORGANISM: Artificial Sequence
<220> FEATURE:
<223> OTHER INFORMATION: Description of Artificial Sequence: Synthetic
      clone 24 polynucleotide

<400> SEQUENCE: 131

gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcagct attgataata gtggtgctta tacatcttac    180

gcagactccg tgaagggcag gttcaccatc tccagagaca attccaagaa cacgctgtat    240

ctgcaaatga acagcctgag agccgaggac acggccgtat attactgtgc gaaaggtagt    300

tctgattttg actactgggg ccagggaacc ctggtcaccg tctcgagcgg tggaggcggt    360

tcaggcggag gtggcagcgg cggtggcggg tcgacggaca tccagatgac ccagtctcca    420

tcctccctgt ctgcatctgt aggagacaga gtcaccatca cttgccgggc aagtcagagc    480

attagcagct atttaaattg gtatcagcag aaaccaggga aagcccctaa gctcctgatc    540

tatggtgcat cctctttgca aagtggggtc ccatcaaggt tcagtggcag tggatctggg    600
```

```
acagatttca ctctcaccat cagcagtctg caacctgaag attttgcaac ttactactgt    660

caacaggctg gtaatgatcc ttctacgttc ggccaaggga ccaaggtgga aatcaaacgg    720


<210> SEQ ID NO 132
<211> LENGTH: 240
<212> TYPE: PRT
<213> ORGANISM: Artificial Sequence
<220> FEATURE:
<223> OTHER INFORMATION: Description of Artificial Sequence: Synthetic
      clone 24 polypeptide
<220> FEATURE:
<221> NAME/KEY: misc_feature
<222> LOCATION: (1)..(116)
<223> OTHER INFORMATION: Variable heavy chain
<220> FEATURE:
<221> NAME/KEY: misc_feature
<222> LOCATION: (31)..(35)
<223> OTHER INFORMATION: Variable heavy chain CDR1
<220> FEATURE:
<221> NAME/KEY: misc_feature
<222> LOCATION: (50)..(69)
<223> OTHER INFORMATION: Variable heavy chain CDR2
<220> FEATURE:
<221> NAME/KEY: misc_feature
<222> LOCATION: (100)..(105)
<223> OTHER INFORMATION: Variable heavy chain CDR3
<220> FEATURE:
<221> NAME/KEY: misc_feature
<222> LOCATION: (132)..(240)
<223> OTHER INFORMATION: Variable light chain
<220> FEATURE:
<221> NAME/KEY: misc_feature
<222> LOCATION: (156)..(166)
<223> OTHER INFORMATION: Variable light chain CDR1
<220> FEATURE:
<221> NAME/KEY: misc_feature
<222> LOCATION: (182)..(188)
<223> OTHER INFORMATION: Variable light chain CDR2
<220> FEATURE:
<221> NAME/KEY: misc_feature
<222> LOCATION: (223)..(229)
<223> OTHER INFORMATION: Variable light chain CDR3

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asp Asn Ser Gly Ala Tyr Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ser Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175
```

```
Lys Leu Leu Ile Tyr Gly Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ala Gly
    210                 215                 220

Asn Asp Pro Ser Thr Phe Gly Gln Gly Thr Lys Val Glu Ile Lys Arg
225                 230                 235                 240
```

<210> SEQ ID NO 133
<211> LENGTH: 116
<212> TYPE: PRT
<213> ORGANISM: Artificial Sequence
<220> FEATURE:
<223> OTHER INFORMATION: Description of Artificial Sequence: Synthetic clone 24 variable heavy chain polypeptide

<400> SEQUENCE: 133

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asp Asn Ser Gly Ala Tyr Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ser Asp Phe Asp Tyr Trp Gly Gln Gly Thr Leu Val
            100                 105                 110

Thr Val Ser Ser
        115
```

<210> SEQ ID NO 134
<211> LENGTH: 5
<212> TYPE: PRT
<213> ORGANISM: Artificial Sequence
<220> FEATURE:
<223> OTHER INFORMATION: Description of Artificial Sequence: Synthetic clone 24 variable heavy chain CDR1 peptide

<400> SEQUENCE: 134

```
Ser Tyr Ala Met Ser
1               5
```

<210> SEQ ID NO 135
<211> LENGTH: 20
<212> TYPE: PRT
<213> ORGANISM: Artificial Sequence
<220> FEATURE:
<223> OTHER INFORMATION: Description of Artificial Sequence: Synthetic clone 24 variable heavy chain CDR2 peptide

<400> SEQUENCE: 135

```
Ala Ile Asp Asn Ser Gly Ala Tyr Thr Ser Tyr Ala Asp Ser Val Lys
1               5                   10                  15

Gly Arg Phe Thr
            20
```

```
<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      clone 24 variable heavy chain CDR3 peptide

<400> SEQUENCE: 136

Ser Ser Asp Phe Asp Tyr
1               5


<210> SEQ ID NO 137
<211> LENGTH: 109
<212> TYPE: PRT
<213> ORGANISM: Artificial Sequence
<220> FEATURE:
<223> OTHER INFORMATION: Description of Artificial Sequence: Synthetic
      clone 24 variable light chain polypeptide

<400> SEQUENCE: 137

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Gly Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ala Gly Asn Asp Pro
                85                  90                  95

Ser Thr Phe Gly Gln Gly Thr Lys Val Glu Ile Lys Arg
            100                 105


<210> SEQ ID NO 138
<211> LENGTH: 11
<212> TYPE: PRT
<213> ORGANISM: Artificial Sequence
<220> FEATURE:
<223> OTHER INFORMATION: Description of Artificial Sequence: Synthetic
      clone 24 variable light chain CDR1 peptide

<400> SEQUENCE: 138

Arg Ala Ser Gln Ser Ile Ser Ser Tyr Leu Asn
1               5                   10


<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 24 variable light chain CDR2 peptide

<400> SEQUENCE: 139

Gly Ala Ser Ser Leu Gln Ser
1               5


<210> SEQ ID NO 140
<211> LENGTH: 7
<212> TYPE: PRT
<213> ORGANISM: Artificial Sequence
```

<220> FEATURE:
<223> OTHER INFORMATION: Description of Artificial Sequence: Synthetic
      clone 24 variable light chain CDR3 peptide

<400> SEQUENCE: 140

Ala Gly Asn Asp Pro Ser Thr
1               5

<210> SEQ ID NO 141
<211> LENGTH: 720
<212> TYPE: DNA
<213> ORGANISM: Artificial Sequence
<220> FEATURE:
<223> OTHER INFORMATION: Description of Artificial Sequence: Synthetic
      clone 26 polynucleotide

<400> SEQUENCE: 141
gaggtgcagc tgttggagtc tgggggaggc ttggtacagc ctggggggtc cctgagactc 60
tcctgtgcag cctctggatt cacctttagc agctatgcca tgagctgggt ccgccaggct 120
ccagggaagg ggctggagtg ggtctcagcg attactgcgc cgggtcctcg gacacagtac 180
gcagactccg tgaagggccg gttcaccatc tccagagaca attccaagaa cacgctgtat 240
ctgcaaatga acagcctgag agccgaggac acggccgtat attactgtgc gaaagggacg 300
cgtacgtttg actactgggg ccagggaacc ctggtcaccg tctcgagcgg tggaggcggt 360
tcaggcggag gtggcagcgg cggtggcggg tcgacggaca tccagatgac ccagtctcca 420
tcctccctgt ctgcatctgt aggagacaga gtcaccatca cttgccgggc aagtcagagc 480
attagcagct atttaaattg gtatcagcag aaaccaggga aagcccctaa gctcctgatc 540
tatggtgcat cccatttgca aagtggggtc ccatcaaggt tcagtggcag tggatctggg 600
acagatttca ctctcaccat cagcagtctg caacctgaag attttgcaac ttactactgt 660
caacagccga cgactacgcc tcgtacgttc ggccaaggga ccaaggtgga aatcaaacgg 720

<210> SEQ ID NO 142
<211> LENGTH: 240
<212> TYPE: PRT
<213> ORGANISM: Artificial Sequence
<220> FEATURE:
<223> OTHER INFORMATION: Description of Artificial Sequence: Synthetic
      clone 26 polypeptide
<220> FEATURE:
<221> NAME/KEY: misc_feature
<222> LOCATION: (1)..(116)
<223> OTHER INFORMATION: Variable heavy chain
<220> FEATURE:
<221> NAME/KEY: misc_feature
<222> LOCATION: (31)..(35)
<223> OTHER INFORMATION: Variable heavy chain CDR1
<220> FEATURE:
<221> NAME/KEY: misc_feature
<222> LOCATION: (50)..(69)
<223> OTHER INFORMATION: Variable heavy chain CDR2
<220> FEATURE:
<221> NAME/KEY: misc_feature
<222> LOCATION: (99)..(105)
<223> OTHER INFORMATION: Variable heavy chain CDR3
<220> FEATURE:
<221> NAME/KEY: misc_feature
<222> LOCATION: (133)..(240)
<223> OTHER INFORMATION: Variable light chain
<220> FEATURE:
<221> NAME/KEY: misc_feature
<222> LOCATION: (156)..(166)
<223> OTHER INFORMATION: Variable light chain CDR1
<220> FEATURE:
<221> NAME/KEY: misc_feature
<222> LOCATION: (182)..(188)

```
<223> OTHER INFORMATION: Variable light chain CDR2
<220> FEATURE:
<221> NAME/KEY: misc_feature
<222> LOCATION: (223)..(229)
<223> OTHER INFORMATION: Variable light chain CDR3

<400> SEQUENCE: 142

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Thr Ala Pro Gly Pro Arg Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Arg Thr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Gly Ala Ser His Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Pro Thr
    210                 215                 220

Thr Thr Pro Arg Thr Phe Gly Gln Gly Thr Lys Val Glu Ile Lys Arg
225                 230                 235                 240


<210> SEQ ID NO 143
<211> LENGTH: 116
<212> TYPE: PRT
<213> ORGANISM: Artificial Sequence
<220> FEATURE:
<223> OTHER INFORMATION: Description of Artificial Sequence: Synthetic
      clone 26 variable heavy chain polypeptide

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Thr Ala Pro Gly Pro Arg Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Gly Thr Arg Thr Phe Asp Tyr Trp Gly Gln Gly Thr Leu Val
            100                 105                 110

Thr Val Ser Ser
        115


<210> SEQ ID NO 144
<211> LENGTH: 5
<212> TYPE: PRT
<213> ORGANISM: Artificial Sequence
<220> FEATURE:
<223> OTHER INFORMATION: Description of Artificial Sequence: Synthetic
      clone 26 variable heavy chain CDR1 peptide

<400> SEQUENCE: 144

Ser Tyr Ala Met Ser
1               5


<210> SEQ ID NO 145
<211> LENGTH: 20
<212> TYPE: PRT
<213> ORGANISM: Artificial Sequence
<220> FEATURE:
<223> OTHER INFORMATION: Description of Artificial Sequence: Synthetic
      clone 26 variable heavy chain CDR2 peptide

<400> SEQUENCE: 145

Ala Ile Thr Ala Pro Gly Pro Arg Thr Gln Tyr Ala Asp Ser Val Lys
1               5                   10                  15

Gly Arg Phe Thr
            20


<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 26 variable heavy chain CDR3 peptide

<400> SEQUENCE: 146

Gly Thr Arg Thr Phe Asp Tyr
1               5


<210> SEQ ID NO 147
<211> LENGTH: 108
<212> TYPE: PRT
<213> ORGANISM: Artificial Sequence
<220> FEATURE:
<223> OTHER INFORMATION: Description of Artificial Sequence: Synthetic
      clone 26 variable light chain polypeptide

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Pro Thr Thr Thr Pro Arg
                85                  90                  95

Thr Phe Gly Gln Gly Thr Lys Val Glu Ile Lys Arg
            100                 105


<210> SEQ ID NO 148
<211> LENGTH: 11
<212> TYPE: PRT
<213> ORGANISM: Artificial Sequence
<220> FEATURE:
<223> OTHER INFORMATION: Description of Artificial Sequence: Synthetic
      clone 26 variable light chain CDR1 peptide

<400> SEQUENCE: 148

Arg Ala Ser Gln Ser Ile Ser Ser Tyr Leu Asn
1               5                   10


<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 26 variable light chain CDR2 peptide

<400> SEQUENCE: 149

Gly Ala Ser His Leu Gln Ser
1               5


<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 26 variable light chain CDR3 peptide

<400> SEQUENCE: 150

Pro Thr Thr Thr Pro Arg Thr
1               5


<210> SEQ ID NO 151
<211> LENGTH: 723
<212> TYPE: DNA
<213> ORGANISM: Artificial Sequence
<220> FEATURE:
<223> OTHER INFORMATION: Description of Artificial Sequence: Synthetic
      clone 27 polynucleotide

<400> SEQUENCE: 151

gaggtgcagc tgttggagtc tgggggaggc ttggtacagc ctggggggtc cctgagactc      60

tcctgtgcag cctctggatt cacctttagc agctatgcca tgagctgggt ccgccaggct     120

ccagggaagg ggctggagtg ggtctcaaag attaagccgc agggtgatgc gacacggtac     180

gcagactccg tgaagggccg gttcaccatc tccagagaca attccaagaa cacgctgtat     240

ctgcaaatga acagcctgag agccgaggac acggccgtat attactgtgc gaaaggggct     300

cggaggtttg actactgggg ccagggaacc ctggtcaccg tctcgagcgg tggaggcggt     360

tcaggcggag gtggcagcgg cggtggcggg tcgacggaca tccagatgac ccagtctcca     420

tcctccctgt ctgcatctgt aggagacaga gtcaccatca cttgccgggc aagtcagagc     480

attagcagct atttaaattg gtatcagcag aaaccaggga aagcccctaa gctcctgatc     540

tatcgtgcat cccgtttgca aagtggggtc ccatcaaggt tcagtggcag tggatctggg     600
```

```
acagatttca ctctcaccat cagcagtctg caacctgaag attttgcaac ttactactgt    660

caacagacta agcggcctcc tcagacgttc ggccaaggga ccaaggtgga aatcaaacgg    720

gcg                                                                  723


<210> SEQ ID NO 152
<211> LENGTH: 241
<212> TYPE: PRT
<213> ORGANISM: Artificial Sequence
<220> FEATURE:
<223> OTHER INFORMATION: Description of Artificial Sequence: Synthetic
      clone 27 polypeptide
<220> FEATURE:
<221> NAME/KEY: misc_feature
<222> LOCATION: (1)..(116)
<223> OTHER INFORMATION: Variable heavy chain
<220> FEATURE:
<221> NAME/KEY: misc_feature
<222> LOCATION: (31)..(35)
<223> OTHER INFORMATION: Variable heavy chain CDR1
<220> FEATURE:
<221> NAME/KEY: misc_feature
<222> LOCATION: (50)..(69)
<223> OTHER INFORMATION: Variable heavy chain CDR2
<220> FEATURE:
<221> NAME/KEY: misc_feature
<222> LOCATION: (99)..(105)
<223> OTHER INFORMATION: Variable heavy chain CDR3
<220> FEATURE:
<221> NAME/KEY: misc_feature
<222> LOCATION: (133)..(241)
<223> OTHER INFORMATION: Variable light chain
<220> FEATURE:
<221> NAME/KEY: misc_feature
<222> LOCATION: (156)..(166)
<223> OTHER INFORMATION: Variable light chain CDR1
<220> FEATURE:
<221> NAME/KEY: misc_feature
<222> LOCATION: (182)..(188)
<223> OTHER INFORMATION: Variable light chain CDR2
<220> FEATURE:
<221> NAME/KEY: misc_feature
<222> LOCATION: (223)..(229)
<223> OTHER INFORMATION: Variable light chain CDR3

<400> SEQUENCE: 152

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Lys Ile Lys Pro Gln Gly Asp Ala Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Arg Arg Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160
```

```
Ile Ser Ser Tyr Leu Asn Trp Tyr Gln Gln Lys Pro Gly Lys Ala Pro
                165                 170                 175

Lys Leu Leu Ile Tyr Arg Ala Ser Arg Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Thr Lys
    210                 215                 220

Arg Pro Pro Gln Thr Phe Gly Gln Gly Thr Lys Val Glu Ile Lys Arg
225                 230                 235                 240

Ala
```

<210> SEQ ID NO 153
<211> LENGTH: 116
<212> TYPE: PRT
<213> ORGANISM: Artificial Sequence
<220> FEATURE:
<223> OTHER INFORMATION: Description of Artificial Sequence: Synthetic clone 27 variable heavy chain polypeptide

<400> SEQUENCE: 153

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Lys Ile Lys Pro Gln Gly Asp Ala Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Arg Arg Phe Asp Tyr Trp Gly Gln Gly Thr Leu Val
            100                 105                 110

Thr Val Ser Ser
        115
```

<210> SEQ ID NO 154
<211> LENGTH: 5
<212> TYPE: PRT
<213> ORGANISM: Artificial Sequence
<220> FEATURE:
<223> OTHER INFORMATION: Description of Artificial Sequence: Synthetic clone 27 variable heavy chain CDR1 peptide

<400> SEQUENCE: 154

```
Ser Tyr Ala Met Ser
1               5
```

<210> SEQ ID NO 155
<211> LENGTH: 20
<212> TYPE: PRT
<213> ORGANISM: Artificial Sequence
<220> FEATURE:
<223> OTHER INFORMATION: Description of Artificial Sequence: Synthetic clone 27 variable heavy chain CDR2 peptide

<400> SEQUENCE: 155

```
Lys Ile Lys Pro Gln Gly Asp Ala Thr Arg Tyr Ala Asp Ser Val Lys
```

```
1               5                   10                  15

Gly Arg Phe Thr
            20


<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 27 variable heavy chain CDR3 peptide

<400> SEQUENCE: 156

Gly Ala Arg Arg Phe Asp Tyr
1               5


<210> SEQ ID NO 157
<211> LENGTH: 109
<212> TYPE: PRT
<213> ORGANISM: Artificial Sequence
<220> FEATURE:
<223> OTHER INFORMATION: Description of Artificial Sequence: Synthetic
      clone 27 variable light chain polypeptide

<400> SEQUENCE: 157

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Lys Arg Pro Pro Gln
                85                  90                  95

Thr Phe Gly Gln Gly Thr Lys Val Glu Ile Lys Arg Ala
            100                 105


<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      clone 27 variable light chain CDR1 peptide

<400> SEQUENCE: 158

Arg Ala Ser Gln Ser Ile Ser Ser Tyr Leu Asn
1               5                   10


<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 27 variable light chain CDR2 peptide

<400> SEQUENCE: 159

Arg Ala Ser Arg Leu Gln Ser
1               5
```

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic clone 27 variable light chain CDR3 peptide

<400> SEQUENCE: 160

Thr Lys Arg Pro Pro Gln Thr
1 5

<210> SEQ ID NO 161
<211> LENGTH: 720
<212> TYPE: DNA
<213> ORGANISM: Artificial Sequence
<220> FEATURE:
<223> OTHER INFORMATION: Description of Artificial Sequence: Synthetic clone 41 polynucleotide

<400> SEQUENCE: 161
gaggtgcagc tgttggagtc tgggggaggc ttggtacagc ctggggggtc cctgagactc 60
tcctgtgcag cctctggatt cacctttagc agctatgcca tgagctgggt ccgccaggct 120
ccagggaagg ggctggagtg ggtctcaacg attaagcaga cgggtacgca gacaaagtac 180
gcagactccg tgaagggccg gttcaccatc tccagagaca attccaagaa cacgctgtat 240
ctgcaaatga acagcctgag agccgaggac acggccgtat attactgtgc gaaaagtggt 300
cggcggtttg actactgggg ccagggaacc ctggtcaccg tctcgagcgg tggaggcggt 360
tcaggcggag gtggcagcgg cggtggcggg tcgacggaca tccagatgac ccagtctcca 420
tcctccctgt ctgcatctgt aggagacaga gtcaccatca cttgccgggc aagtcagagc 480
attagcagct atttaaattg gtatcagcag aaaccaggga aagcccctaa gctcctgatc 540
tataaggcat cccgtttgca aagtggggtc ccatcaaggt tcagtggcag tggatctggg 600
acagatttca ctctcaccat cagcagtctg caacctgaag attttgcaac ttactactgt 660
caacaggcta gtcttacgcc tccgacgttc ggccaaggga ccaaggtgga aatcaaacgg 720

<210> SEQ ID NO 162
<211> LENGTH: 240
<212> TYPE: PRT
<213> ORGANISM: Artificial Sequence
<220> FEATURE:
<223> OTHER INFORMATION: Description of Artificial Sequence: Synthetic clone 41 polypeptide
<220> FEATURE:
<221> NAME/KEY: misc_feature
<222> LOCATION: (1)..(116)
<223> OTHER INFORMATION: Variable heavy chain
<220> FEATURE:
<221> NAME/KEY: misc_feature
<222> LOCATION: (31)..(35)
<223> OTHER INFORMATION: Variable heavy chain CDR1
<220> FEATURE:
<221> NAME/KEY: misc_feature
<222> LOCATION: (50)..(69)
<223> OTHER INFORMATION: Variable heavy chain CDR2
<220> FEATURE:
<221> NAME/KEY: misc_feature
<222> LOCATION: (99)..(105)
<223> OTHER INFORMATION: Variable heavy chain CDR3
<220> FEATURE:
<221> NAME/KEY: misc_feature
<222> LOCATION: (133)..(240)
<223> OTHER INFORMATION: Variable light chain
<220> FEATURE:
<221> NAME/KEY: misc_feature

```
<222> LOCATION: (156)..(166)
<223> OTHER INFORMATION: Variable light chain CDR1
<220> FEATURE:
<221> NAME/KEY: misc_feature
<222> LOCATION: (182)..(187)
<223> OTHER INFORMATION: Variable light chain CDR2
<220> FEATURE:
<221> NAME/KEY: misc_feature
<222> LOCATION: (223)..(229)
<223> OTHER INFORMATION: Variable light chain CDR3

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Lys Gln Thr Gly Thr Gln Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Arg Arg Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Lys Ala Ser Arg Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ala Ser
    210                 215                 220

Leu Thr Pro Pro Thr Phe Gly Gln Gly Thr Lys Val Glu Ile Lys Arg
225                 230                 235                 240


<210> SEQ ID NO 163
<211> LENGTH: 116
<212> TYPE: PRT
<213> ORGANISM: Artificial Sequence
<220> FEATURE:
<223> OTHER INFORMATION: Description of Artificial Sequence: Synthetic
      clone 41 variable heavy chain polypeptide

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Lys Gln Thr Gly Thr Gln Thr Lys Tyr Ala Asp Ser Val
```

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Arg Arg Phe Asp Tyr Trp Gly Gln Gly Thr Leu Val
            100                 105                 110

Thr Val Ser Ser
        115


<210> SEQ ID NO 164
<211> LENGTH: 5
<212> TYPE: PRT
<213> ORGANISM: Artificial Sequence
<220> FEATURE:
<223> OTHER INFORMATION: Description of Artificial Sequence: Synthetic
      clone 41 variable heavy chain CDR1 peptide

<400> SEQUENCE: 164

Ser Tyr Ala Met Ser
1               5


<210> SEQ ID NO 165
<211> LENGTH: 20
<212> TYPE: PRT
<213> ORGANISM: Artificial Sequence
<220> FEATURE:
<223> OTHER INFORMATION: Description of Artificial Sequence: Synthetic
      clone 41 variable heavy chain CDR2 peptide

<400> SEQUENCE: 165

Thr Ile Lys Gln Thr Gly Thr Gln Thr Lys Tyr Ala Asp Ser Val Lys
1               5                   10                  15

Gly Arg Phe Thr
            20


<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 41 variable heavy chain CDR3 peptide

<400> SEQUENCE: 166

Ser Gly Arg Arg Phe Asp Tyr
1               5


<210> SEQ ID NO 167
<211> LENGTH: 108
<212> TYPE: PRT
<213> ORGANISM: Artificial Sequence
<220> FEATURE:
<223> OTHER INFORMATION: Description of Artificial Sequence: Synthetic
      clone 41 variable light chain polypeptide

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Lys Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Leu Thr Pro Pro
                85                  90                  95

Thr Phe Gly Gln Gly Thr Lys Val Glu Ile Lys Arg
            100                 105


<210> SEQ ID NO 168
<211> LENGTH: 11
<212> TYPE: PRT
<213> ORGANISM: Artificial Sequence
<220> FEATURE:
<223> OTHER INFORMATION: Description of Artificial Sequence: Synthetic
      clone 41 variable light chain CDR1 peptide

<400> SEQUENCE: 168

Arg Ala Ser Gln Ser Ile Ser Ser Tyr Leu Asn
1               5                   10


<210> SEQ ID NO 169
<211> LENGTH: 6
<212> TYPE: PRT
<213> ORGANISM: Artificial Sequence
<220> FEATURE:
<223> OTHER INFORMATION: Description of Artificial Sequence: Synthetic
      clone 41 variable light chain CDR2 peptide

<400> SEQUENCE: 169

Lys Ala Ser Arg Leu Gln
1               5


<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      clone 41 variable light chain CDR3 peptide

<400> SEQUENCE: 170

Ala Ser Leu Thr Pro Pro Thr
1               5


<210> SEQ ID NO 171
<211> LENGTH: 990
<212> TYPE: DNA
<213> ORGANISM: Homo sapiens
<220> FEATURE:
<223> OTHER INFORMATION: human IgG1

<400> SEQUENCE: 171

gctagcacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagaa agttgagccc    300

aaatcttgtg acaaaactca cacatgccca ccgtgcccag cacctgaact cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480
```

```
tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcctccatc tcgggatgag    720

ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctat agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa                                      990


<210> SEQ ID NO 172
<211> LENGTH: 330
<212> TYPE: PRT
<213> ORGANISM: Homo sapiens
<220> FEATURE:
<223> OTHER INFORMATION: human IgG1

<400> SEQUENCE: 172

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 173
<211> LENGTH: 318
<212> TYPE: DNA
<213> ORGANISM: Homo sapiens
<220> FEATURE:
<223> OTHER INFORMATION: human CK

<400> SEQUENCE: 173

accgtggcgg cgccatctgt cttcatcttc ccgccatctg atgagcagtt gaaatctggt      60

accgctagcg ttgtgtgcct gctgaataac ttctatccca gagaggccaa agtacagtgg     120

aaggtggata acgccctcca atcgggtaac tcccaggaga gtgtcacaga gcaggacagc     180

aaggacagca cctacagcct cagcagcacc ctgacgctga gcaaagcaga ctacgagaaa     240

cacaaagtct acgcctgcga agtcacccat cagggcctga gctcgcccgt cacaaagagc     300

ttcaacaggg gagagtgt                                                   318


<210> SEQ ID NO 174
<211> LENGTH: 106
<212> TYPE: PRT
<213> ORGANISM: Homo sapiens
<220> FEATURE:
<223> OTHER INFORMATION: human CK

<400> SEQUENCE: 174

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105


<210> SEQ ID NO 175
<211> LENGTH: 1338
<212> TYPE: DNA
<213> ORGANISM: Artificial Sequence
<220> FEATURE:
<223> OTHER INFORMATION: Description of Artificial Sequence: Synthetic
      clone 1 VH-CH123 polynucleotide

<400> SEQUENCE: 175

gaggtgcagc tgttggagtc tgggggaggc ttggtacagc ctggggggtc cctgagactc      60
```

-continued

```
tcctgtgcag cctctggatt cacctttagc agctatgcca tgagctgggt ccgccaggct    120

ccagggaagg ggctggagtg ggtctcatcg atttctcagc ggggtcggaa gacactgtac    180

gcagactccg tgaagggccg gttcaccatc tccagagaca attccaagaa cacgctgtat    240

ctgcaaatga acagcctgag agccgaggac acggccgtat attactgtgc gaaaggtctg    300

cgtcgttttg actactgggg ccagggaacc ctggtcaccg tctcgagcgc tagcaccaag    360

ggcccatcgg tcttcccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gacaagaaag ttgagcccaa atcttgtgac    660

aaaactcaca catgcccacc gtgcccagca cctgaactcc tggggggacc gtcagtcttc    720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cccagccccc atcgagaaaa ccatctccaa agccaaaggg   1020

cagccccgag aaccacaggt gtacaccctg cctccatctc gggatgagct gaccaagaac   1080

caggtcagcc tgacctgcct ggtcaaaggc ttctatccca gcgacatcgc cgtggagtgg   1140

gagagcaatg ggcagccgga gaacaactac aagaccacgc ctcccgtgct ggactccgac   1200

ggctccttct tcctctatag caagctcacc gtggacaaga gcaggtggca gcaggggaac   1260

gtcttctcat gctccgtgat gcatgaggct ctgcacaacc actacacgca gaagagcctc   1320

tccctgtctc cgggtaaa                                                 1338
```

```
<210> SEQ ID NO 176
<211> LENGTH: 446
<212> TYPE: PRT
<213> ORGANISM: Artificial Sequence
<220> FEATURE:
<223> OTHER INFORMATION: Description of Artificial Sequence: Synthetic
      clone 1 VH-CH123 polypeptide

<400> SEQUENCE: 176

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Gln Arg Gly Arg Lys Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Arg Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125
```

```
Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 177
<211> LENGTH: 642
<212> TYPE: DNA
<213> ORGANISM: Artificial Sequence
<220> FEATURE:
<223> OTHER INFORMATION: Description of Artificial Sequence: Synthetic clone 1 VL-CK polynucleotide

<400> SEQUENCE: 177

```
gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatatg gcatccccatt tgcaaagtgg ggtcccatca    180

aggttcagtg gcagtggatc tgggacagat ttcactctca ccatcagcag tctgcaacct    240
```

```
gaagattttg caacttacta ctgtcaacag ccgcgttcta cgcctttgac gttcggtcaa    300

gggaccaagg tggaaatcaa acggaccgtg gcggcgccat ctgtcttcat cttcccgcca    360

tctgatgagc agttgaaatc tggtaccgct agcgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                        642
```

<210> SEQ ID NO 178
<211> LENGTH: 214
<212> TYPE: PRT
<213> ORGANISM: Artificial Sequence
<220> FEATURE:
<223> OTHER INFORMATION: Description of Artificial Sequence: Synthetic clone 1 VL-CK polypeptide

<400> SEQUENCE: 178

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Met Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Arg Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 179
<211> LENGTH: 1338
<212> TYPE: DNA
<213> ORGANISM: Artificial Sequence
<220> FEATURE:
<223> OTHER INFORMATION: Description of Artificial Sequence: Synthetic clone 2 VH-CH123 polynucleotide

<400> SEQUENCE: 179

```
gaggtgcagc tgttggagtc tgggggaggc ttggtacagc ctgggggtc cctgagactc     60
```

```
tcctgtgcag cctctggatt cacctttagc agctatgcca tgagctgggt ccgccaggct    120

ccagggaagg ggctggagtg ggtctcaacg attactacta ctggtaccgc gacatggtac    180

gcagactccg tgaagggccg gttcaccatc tccagagaca attccaagaa cacgctgtat    240

ctgcaaatga acagcctgag agccgaggac acggccgtat attactgtgc gaaaactctt    300

cagcgttttg actactgggg ccagggaacc ctggtcaccg tctcgagcgc tagcaccaag    360

ggcccatcgg tcttccccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gacaagaaag ttgagcccaa atcttgtgac    660

aaaactcaca catgcccacc gtgcccagca cctgaactcc tggggggacc gtcagtcttc    720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cccagccccc atcgagaaaa ccatctccaa agccaaaggg   1020

cagccccgag aaccacaggt gtacaccctg cctccatctc gggatgagct gaccaagaac   1080

caggtcagcc tgacctgcct ggtcaaaggc ttctatccca gcgacatcgc cgtggagtgg   1140

gagagcaatg ggcagccgga gaacaactac aagaccacgc ctcccgtgct ggactccgac   1200

ggctccttct tcctctatag caagctcacc gtggacaaga gcaggtggca gcaggggaac   1260

gtcttctcat gctccgtgat gcatgaggct ctgcacaacc actacacgca gaagagcctc   1320

tccctgtctc cgggtaaa                                                 1338
```

```
<210> SEQ ID NO 180
<211> LENGTH: 446
<212> TYPE: PRT
<213> ORGANISM: Artificial Sequence
<220> FEATURE:
<223> OTHER INFORMATION: Description of Artificial Sequence: Synthetic
      clone 2 VH-CH123 polypeptide

<400> SEQUENCE: 180

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Thr Thr Thr Gly Thr Ala Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Leu Gln Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125
```

```
Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 181
<211> LENGTH: 642
<212> TYPE: DNA
<213> ORGANISM: Artificial Sequence
<220> FEATURE:
<223> OTHER INFORMATION: Description of Artificial Sequence: Synthetic clone 2 VL-CK polynucleotide

<400> SEQUENCE: 181

```
gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatgag gcatccgtgt tgcaaagtgg ggtcccatca    180

aggttcagtg gcagtggatc tgggacagat ttcactctca ccatcagcag tctgcaaccc    240
```

```
gaagattttg caacttacta ctgtcaacag ccgaggtctc tgcctatgac gttcggccaa    300

gggaccaagg tggaaatcaa acggaccgtg gcggcgccat ctgtcttcat cttcccgcca    360

tctgatgagc agttgaaatc tggtaccgct agcgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                        642
```

<210> SEQ ID NO 182
<211> LENGTH: 214
<212> TYPE: PRT
<213> ORGANISM: Artificial Sequence
<220> FEATURE:
<223> OTHER INFORMATION: Description of Artificial Sequence: Synthetic clone 2 VL-CK polypeptide

<400> SEQUENCE: 182

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Glu Ala Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Arg Ser Leu Pro Met
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 183
<211> LENGTH: 1338
<212> TYPE: DNA
<213> ORGANISM: Artificial Sequence
<220> FEATURE:
<223> OTHER INFORMATION: Description of Artificial Sequence: Synthetic clone 3 VH-CH123 polynucleotide

<400> SEQUENCE: 183

```
gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcaggg attgggctta gtggtggggg gacacagtac    180

gcagactccg tgaagggcag gttcaccatc tccagagaca attccaagaa cacgctgtat    240

ctgcaaatga acagcctgag agccgaggac acggccgtat attactgtgc gaaaggtact    300

actcggtttg actactgggg ccagggaacc ctggtcaccg tctcgagcgc tagcaccaag    360

ggcccatcgg tcttccccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gacaagaaag ttgagcccaa atcttgtgac    660

aaaactcaca catgcccacc gtgcccagca cctgaactcc tggggggacc gtcagtcttc    720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cccagccccc atcgagaaaa ccatctccaa agccaaaggg   1020

cagccccgag aaccacaggt gtacaccctg cctccatctc gggatgagct gaccaagaac   1080

caggtcagcc tgacctgcct ggtcaaaggc ttctatccca gcgacatcgc cgtggagtgg   1140

gagagcaatg ggcagccgga gaacaactac aagaccacgc ctcccgtgct ggactccgac   1200

ggctccttct tcctctatag caagctcacc gtggacaaga gcaggtggca gcaggggaac   1260

gtcttctcat gctccgtgat gcatgaggct ctgcacaacc actacacgca gaagagcctc   1320

tccctgtctc cgggtaaa                                                 1338


<210> SEQ ID NO 184
<211> LENGTH: 446
<212> TYPE: PRT
<213> ORGANISM: Artificial Sequence
<220> FEATURE:
<223> OTHER INFORMATION: Description of Artificial Sequence: Synthetic
      clone 3 VH-CH123 polypeptide

<400> SEQUENCE: 184

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Gly Leu Ser Gly Gly Gly Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
```

```
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 185
<211> LENGTH: 642
<212> TYPE: DNA
<213> ORGANISM: Artificial Sequence
<220> FEATURE:
<223> OTHER INFORMATION: Description of Artificial Sequence: Synthetic clone 3 VL-CK polynucleotide

<400> SEQUENCE: 185

```
aacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctataag gcatcccgtt tgcaaagtgg ggtcccatca    180
```

```
aggttcagtg gcagtggatc tgggacagat ttcactctca ccatcagcag tctgcaacct    240

gaagattttg caacttacta ctgtcaacag tttttggttc ttcctcgtac gttcggccaa    300

gggaccaagg tggaaatcaa acggaccgtg gcggcgccat ctgtcttcat cttcccgcca    360

tctgatgagc agttgaaatc tggtaccgct agcgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                        642
```

```
<210> SEQ ID NO 186
<211> LENGTH: 214
<212> TYPE: PRT
<213> ORGANISM: Artificial Sequence
<220> FEATURE:
<223> OTHER INFORMATION: Description of Artificial Sequence: Synthetic
      clone 3 VL-CK polypeptide

<400> SEQUENCE: 186

Asn Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Lys Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Leu Val Leu Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 187
<211> LENGTH: 1338
<212> TYPE: DNA
<213> ORGANISM: Artificial Sequence
<220> FEATURE:
<223> OTHER INFORMATION: Description of Artificial Sequence: Synthetic
      clone 4 VH-CH123 polynucleotide

<400> SEQUENCE: 187
```

```
gaggtgcagc tgttggagtc tgggggaggc ttggtacagc ctggggggtc cctgagactc      60

tcctgtgcag cctctggatt cacctttagc agctatgcca tgagctgggt ccgccaggct     120

ccagggaagg ggctggagtg ggtctcaagt attaatggtt atggtgataa tacagattac     180

gcagactccg tgaagggcag gttcaccatc tccagagaca attccaagaa cacgctgtat     240

ctgcaaatga acagcctgag agccgaggac acggccgtat attactgtgc gaaaggttct     300

tctgattttg actactgggg ccagggaacc ctggtcaccg tctcgagcgc tagcaccaag     360

ggcccatcgg tcttccccct ggcaccctcc tccaagagca cctctggggg cacagcggcc     420

ctgggctgcc tggtcaagga ctacttcccc gaaccggtga cggtgtcgtg gaactcaggc     480

gccctgacca gcggcgtgca caccttcccg gctgtcctac agtcctcagg actctactcc     540

ctcagcagcg tggtgaccgt gccctccagc agcttgggca cccagaccta catctgcaac     600

gtgaatcaca agcccagcaa caccaaggtg gacaagaaag ttgagcccaa atcttgtgac     660

aaaactcaca catgcccacc gtgcccagca cctgaactcc tggggggacc gtcagtcttc     720

ctcttccccc caaaacccaa ggacaccctc atgatctccc ggacccctga ggtcacatgc     780

gtggtggtgg acgtgagcca cgaagaccct gaggtcaagt tcaactggta cgtggacggc     840

gtggaggtgc ataatgccaa gacaaagccg cgggaggagc agtacaacag cacgtaccgt     900

gtggtcagcg tcctcaccgt cctgcaccag gactggctga atggcaagga gtacaagtgc     960

aaggtctcca acaaagccct cccagccccc atcgagaaaa ccatctccaa agccaaaggg    1020

cagccccgag aaccacaggt gtacaccctg cctccatctc gggatgagct gaccaagaac    1080

caggtcagcc tgacctgcct ggtcaaaggc ttctatccca gcgacatcgc cgtggagtgg    1140

gagagcaatg ggcagccgga gaacaactac aagaccacgc ctcccgtgct ggactccgac    1200

ggctccttct tcctctatag caagctcacc gtggacaaga gcaggtggca gcaggggaac    1260

gtcttctcat gctccgtgat gcatgaggct ctgcacaacc actacacgca gaagagcctc    1320

tccctgtctc cgggtaaa                                                  1338
```

<210> SEQ ID NO 188
<211> LENGTH: 446
<212> TYPE: PRT
<213> ORGANISM: Artificial Sequence
<220> FEATURE:
<223> OTHER INFORMATION: Description of Artificial Sequence: Synthetic clone 4 VH-CH123 polypeptide

<400> SEQUENCE: 188

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asn Gly Tyr Gly Asp Asn Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ser Asp Phe Asp Tyr Trp Gly Gln Gly Thr Leu Val
            100                 105                 110
```

```
Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 189
<211> LENGTH: 642
<212> TYPE: DNA
<213> ORGANISM: Artificial Sequence
<220> FEATURE:
<223> OTHER INFORMATION: Description of Artificial Sequence: Synthetic clone 4 VL-CK polynucleotide

<400> SEQUENCE: 189

```
gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatggt gcatcctctt tgcaaagtgg ggtcccatca    180
```

```
aggttcagtg gcagtggatc tgggacagat ttcactctca ccatcagcag tctgcaacct    240

gaagattttg caacttacta ctgtcaacag gctggttatg atcctactac gttcggccaa    300

gggaccaagg tggaaatcaa acggaccgtg gcggcgccat ctgtcttcat cttcccgcca    360

tctgatgagc agttgaaatc tggtaccgct agcgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

```
<210> SEQ ID NO 190
<211> LENGTH: 214
<212> TYPE: PRT
<213> ORGANISM: Artificial Sequence
<220> FEATURE:
<223> OTHER INFORMATION: Description of Artificial Sequence: Synthetic
      clone 4 VL-CK polypeptide

<400> SEQUENCE: 190

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Gly Tyr Asp Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 191
<211> LENGTH: 1338
<212> TYPE: DNA
<213> ORGANISM: Artificial Sequence
<220> FEATURE:
<223> OTHER INFORMATION: Description of Artificial Sequence: Synthetic
      clone 5 VH-CH123 polynucleotide
```

<400> SEQUENCE: 191

```
gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcagct attgctaatg ctggtgctac tacaaattac    180

gcagactccg tgaagggcag gttcaccatc tccagagaca attccaagaa cacgctgtat    240

ctgcaaatga acagcctgag agccgaggac acggccgtat attactgtgc gaaaggtagt    300

agtgattttg actactgggg ccagggaacc ctggtcaccg tctcgagcgc tagcaccaag    360

ggcccatcgg tcttccccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gacaagaaag ttgagcccaa atcttgtgac    660

aaaactcaca catgcccacc gtgcccagca cctgaactcc tggggggacc gtcagtcttc    720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cccagccccc atcgagaaaa ccatctccaa agccaaaggg   1020

cagccccgag aaccacaggt gtacaccctg cctccatctc gggatgagct gaccaagaac   1080

caggtcagcc tgacctgcct ggtcaaaggc ttctatccca gcgacatcgc cgtggagtgg   1140

gagagcaatg ggcagccgga gaacaactac aagaccacgc ctcccgtgct ggactccgac   1200

ggctccttct tcctctatag caagctcacc gtggacaaga gcaggtggca gcaggggaac   1260

gtcttctcat gctccgtgat gcatgaggct ctgcacaacc actacacgca gaagagcctc   1320

tccctgtctc cgggtaaa                                                 1338
```

<210> SEQ ID NO 192
<211> LENGTH: 446
<212> TYPE: PRT
<213> ORGANISM: Artificial Sequence
<220> FEATURE:
<223> OTHER INFORMATION: Description of Artificial Sequence: Synthetic
      clone 5 VH-CH123 polypeptide

<400> SEQUENCE: 192

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ala Asn Ala Gly Ala Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ser Asp Phe Asp Tyr Trp Gly Gln Gly Thr Leu Val
            100                 105                 110
```

```
Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 193
<211> LENGTH: 642
<212> TYPE: DNA
<213> ORGANISM: Artificial Sequence
<220> FEATURE:
<223> OTHER INFORMATION: Description of Artificial Sequence: Synthetic clone 5 VL-CK polynucleotide

<400> SEQUENCE: 193

```
gacatccaga tgacccagtc tccatcctcc ctgtctgcat ctgtaggaga cagagtcacc     60

atcacttgcc gggcaagtca gagcattagc agctatttaa attggtatca gcagaaacca    120
```

gggaaagccc ctaagctcct gatctatggt gcatccaatt tgcaaagtgg ggtcccatca 180
aggttcagtg gcagtggatc tgggacagat ttcactctca ccatcagcag tctgcaacct 240
gaagattttg caacttacta ctgtcaacag agtggttatg atcctagtac gttcggccaa 300
gggaccaagg tggaaatcaa acggaccgtg gcggcgccat ctgtcttcat cttcccgcca 360
tctgatgagc agttgaaatc tggtaccgct agcgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 194
<211> LENGTH: 214
<212> TYPE: PRT
<213> ORGANISM: Artificial Sequence
<220> FEATURE:
<223> OTHER INFORMATION: Description of Artificial Sequence: Synthetic clone 5 VL-CK polypeptide

<400> SEQUENCE: 194

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Gly Ala Ser Asn Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Gly Tyr Asp Pro Ser
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 195
<211> LENGTH: 1338
<212> TYPE: DNA
<213> ORGANISM: Artificial Sequence
<220> FEATURE:
<223> OTHER INFORMATION: Description of Artificial Sequence: Synthetic clone 9 VH-CH123 polynucleotide

<400> SEQUENCE: 195

```
gaggtgcagc tgttggagtc tgggggaggc ttggtacagc ctggggggtc cctgagactc     60
tcctgtgcag cctctggatt cacctttagc agctatgcca tgagctgggt ccgccaggct    120
ccagggaagg ggctggagtg ggtctcaacg attcaggggc gtggtcatag gacagcgtac    180
gcagactccg tgaagggccg gttcaccatc tccagagaca attccaagaa cacgctgtat    240
ctgcaaatga acagcctgag agccgaggac acggccgtat attactgtgc gaaatcgtcg    300
cttgtttttg actactgggg ccagggaacc ctggtcaccg tctcgagcgc tagcaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtacaccctg cctccatctc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctatag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                 1338
```

<210> SEQ ID NO 196
<211> LENGTH: 446
<212> TYPE: PRT
<213> ORGANISM: Artificial Sequence
<220> FEATURE:
<223> OTHER INFORMATION: Description of Artificial Sequence: Synthetic
      clone 9 VH-CH123 polypeptide

<400> SEQUENCE: 196

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Gln Gly Arg Gly His Arg Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Leu Val Phe Asp Tyr Trp Gly Gln Gly Thr Leu Val
```

```
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 197
<211> LENGTH: 642
<212> TYPE: DNA
<213> ORGANISM: Artificial Sequence
<220> FEATURE:
<223> OTHER INFORMATION: Description of Artificial Sequence: Synthetic clone 9 VL-CK polynucleotide

<400> SEQUENCE: 197

```
gacatccaga tgacccagtc tccatcctcc ctgtctgcat ctgtaggaga cagagtcacc     60

atcacttgcc gggcaagtca gagcattagc agctatttaa attggtatca gcagaaacca    120
```

```
gggaaagccc ctaagctcct gatctataag gcatccagat tgcaaagtgg ggtcccatca    180

aggttcagtg gcagtggatc tgggacagat ttcactctca ccatcagcag tctgcaacct    240

gaagattttg caacttacta ctgtcaacag agtatgctga agcctccgac gttcggccaa    300

gggaccaagg tggaaatcaa acggaccgtg gcggcgccat ctgtcttcat cttcccgcca    360

tctgatgagc agttgaaatc tggtaccgct agcgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 198
<211> LENGTH: 214
<212> TYPE: PRT
<213> ORGANISM: Artificial Sequence
<220> FEATURE:
<223> OTHER INFORMATION: Description of Artificial Sequence: Synthetic
      clone 9 VL-CK polypeptide

<400> SEQUENCE: 198

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Lys Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Met Leu Lys Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 199
<211> LENGTH: 1338
<212> TYPE: DNA
<213> ORGANISM: Artificial Sequence
<220> FEATURE:
<223> OTHER INFORMATION: Description of Artificial Sequence: Synthetic clone 11 VH-CH123 polynucleotide

<400> SEQUENCE: 199

```
gaggtgcagc tgttggagtc tgggggaggc ttggtacagc ctggggggtc cctgagactc     60
tcctgtgcag cctctggatt cacctttagc agctatgcca tgagctgggt ccgccaggct    120
ccagggaagg ggctggagtg ggtctcatct attagtgcta ctggtgctac tacaggttac    180
gcagactccg tgaagggccg gttcaccatc tccagagaca attccaagaa cacgctgtat    240
ctgcaaatga acagcctgag agccgaggac acggccgtat attactgtgc gaaatctggt    300
actgattttg actactgggg ccagggaacc ctggtcaccg tctcgagcgc tagcaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtacaccctg cctccatctc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctatag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                 1338
```

<210> SEQ ID NO 200
<211> LENGTH: 446
<212> TYPE: PRT
<213> ORGANISM: Artificial Sequence
<220> FEATURE:
<223> OTHER INFORMATION: Description of Artificial Sequence: Synthetic
clone 11 VH-CH123 polypeptide

<400> SEQUENCE: 200

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ala Thr Gly Ala Thr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Ser Gly Thr Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

```
<210> SEQ ID NO 201
<211> LENGTH: 642
<212> TYPE: DNA
<213> ORGANISM: Artificial Sequence
<220> FEATURE:
<223> OTHER INFORMATION: Description of Artificial Sequence: Synthetic
      clone 11 VL-CK polynucleotide

<400> SEQUENCE: 201

gacatccaga tgacccagtc tccatcctcc ctgtctgcat ctgtaggaga cagagtcacc     60
```

```
atcacttgcc gggcaagtca gagcattagc agctatttaa attggtatca gcagaaacca    120

gggaaagccc ctaagctcct gatctatggt gcatcctatt tgcaaagtgg ggtcccatca    180

aggttcagtg gcagtggatc tgggacagat ttcactctca ccatcagcag tctgcaacct    240

gaagattttg caacttacta ctgtcaacag agtggtaatg atcctactac gttcggccaa    300

gggaccaagg tggaaatcaa acggaccgtg gcggcgccat ctgtcttcat cttcccgcca    360

tctgatgagc agttgaaatc tggtaccgct agcgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                        642
```

```
<210> SEQ ID NO 202
<211> LENGTH: 214
<212> TYPE: PRT
<213> ORGANISM: Artificial Sequence
<220> FEATURE:
<223> OTHER INFORMATION: Description of Artificial Sequence: Synthetic
      clone 11 VL-CK polypeptide

<400> SEQUENCE: 202

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Asn Asp Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 203
<211> LENGTH: 1338
<212> TYPE: DNA
<213> ORGANISM: Artificial Sequence
<220> FEATURE:
```

<223> OTHER INFORMATION: Description of Artificial Sequence: Synthetic
      clone 13 VH-CH123 polynucleotide

<400> SEQUENCE: 203

```
gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcatct atttatccgc agggtctgcg gacatattac    180

gcagactccg tgaagggccg gttcaccatc tccagagaca attccaagaa cacgctgtat    240

ctgcaaatga acagcctgag agccgaggac acggccgtat attactgtgc gaaaaatctt    300

gctaagtttg actactgggg ccagggaacc ctggtcaccg tctcgagcgc tagcaccaag    360

ggcccatcgg tcttcccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gacaagaaag ttgagcccaa atcttgtgac    660

aaaactcaca catgcccacc gtgcccagca cctgaactcc tggggggacc gtcagtcttc    720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cccagccccc atcgagaaaa ccatctccaa agccaaaggg   1020

cagccccgag aaccacaggt gtacaccctg cctccatctc gggatgagct gaccaagaac   1080

caggtcagcc tgacctgcct ggtcaaaggc ttctatccca gcgacatcgc cgtggagtgg   1140

gagagcaatg ggcagccgga gaacaactac aagaccacgc ctcccgtgct ggactccgac   1200

ggctccttct tcctctatag caagctcacc gtggacaaga gcaggtggca gcaggggaac   1260

gtcttctcat gctccgtgat gcatgaggct ctgcacaacc actacacgca gaagagcctc   1320

tccctgtctc cgggtaaa                                                 1338
```

<210> SEQ ID NO 204
<211> LENGTH: 446
<212> TYPE: PRT
<213> ORGANISM: Artificial Sequence
<220> FEATURE:
<223> OTHER INFORMATION: Description of Artificial Sequence: Synthetic
      clone 13 VH-CH123 polypeptide

<400> SEQUENCE: 204

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Tyr Pro Gln Gly Leu Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Asn Leu Ala Lys Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 205
<211> LENGTH: 642
<212> TYPE: DNA
<213> ORGANISM: Artificial Sequence
<220> FEATURE:
<223> OTHER INFORMATION: Description of Artificial Sequence: Synthetic
      clone 13 VL-CK polynucleotide

<400> SEQUENCE: 205

```
gacatccaga tgacccagtc tccatcctcc ctgtctgcat ctgtaggaga cagagtcacc     60
```

```
atcacttgcc gggcaagtca gagcattagc agctatttaa attggtatca gcagaaacca    120

gggaaagccc ctaagctcct gatctatagg gcatccactt tgcaaagtgg ggtcccatca    180

aggttcagtg gcagtggatc tgggacagat ttcactctca ccatcagcag tctgcaacct    240

gaagattttg caacttacta ctgtcaacag cctcgggcgc ttcctggtac gttcggccaa    300

gggaccaagg tggaaatcaa acggaccgtg gcggcgccat ctgtcttcat cttcccgcca    360

tctgatgagc agttgaaatc tggtaccgct agcgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 206
<211> LENGTH: 214
<212> TYPE: PRT
<213> ORGANISM: Artificial Sequence
<220> FEATURE:
<223> OTHER INFORMATION: Description of Artificial Sequence: Synthetic clone 13 VL-CK polypeptide

<400> SEQUENCE: 206

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Arg Ala Leu Pro Gly
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 207
<211> LENGTH: 1338
<212> TYPE: DNA
<213> ORGANISM: Artificial Sequence
<220> FEATURE:
<223> OTHER INFORMATION: Description of Artificial Sequence: Synthetic
      clone 16 VH-CH123 polynucleotide

<400> SEQUENCE: 207

```
gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcacgg attactggtt ctggtggtca gacaacttac    180

gcagactccg tgaagggccg gttcaccatc tccagagaca attccaagaa cacgctgtat    240

ctgcaaatga acagcctgag agccgaggac acggccgtat attactgtgc gaaaggtatg    300

cgtcagtttg actactgggg ccagggaacc ctggtcaccg tctcgagcgc tagcaccaag    360

ggcccatcgg tcttccccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gacaagaaag ttgagcccaa atcttgtgac    660

aaaactcaca catgcccacc gtgcccagca cctgaactcc tggggggacc gtcagtcttc    720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cccagccccc atcgagaaaa ccatctccaa agccaaaggg   1020

cagccccgag aaccacaggt gtacaccctg cctccatctc gggatgagct gaccaagaac   1080

caggtcagcc tgacctgcct ggtcaaaggc ttctatccca gcgacatcgc cgtggagtgg   1140

gagagcaatg ggcagccgga gaacaactac aagaccacgc ctcccgtgct ggactccgac   1200

ggctccttct tcctctatag caagctcacc gtggacaaga gcaggtggca gcaggggaac   1260

gtcttctcat gctccgtgat gcatgaggct ctgcacaacc actacacgca gaagagcctc   1320

tccctgtctc cgggtaaa                                                 1338
```

<210> SEQ ID NO 208
<211> LENGTH: 446
<212> TYPE: PRT
<213> ORGANISM: Artificial Sequence
<220> FEATURE:
<223> OTHER INFORMATION: Description of Artificial Sequence: Synthetic
      clone 16 VH-CH123 polypeptide

<400> SEQUENCE: 208

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Thr Gly Ser Gly Gly Gln Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95

Ala Lys Gly Met Arg Gln Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 209
<211> LENGTH: 642
<212> TYPE: DNA
<213> ORGANISM: Artificial Sequence
<220> FEATURE:
<223> OTHER INFORMATION: Description of Artificial Sequence: Synthetic
clone 16 VL-CK polynucleotide

<400> SEQUENCE: 209

```
gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatttatcgt gcatcctctt tgcaaagtgg ggtcccatca    180

aggttcagtg gcagtggatc tgggacagat ttcactctca ccatcagcag tctgcaacct    240

gaagattttg caacttacta ctgtcaacag gcgcgtgtgc cgcctactac gttcggccaa    300

gggaccaagg tggaaatcaa acggaccgtg gcggcgccat ctgtcttcat cttcccgcca    360

tctgatgagc agttgaaatc tggtaccgct agcgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                        642
```

```
<210> SEQ ID NO 210
<211> LENGTH: 214
<212> TYPE: PRT
<213> ORGANISM: Artificial Sequence
<220> FEATURE:
<223> OTHER INFORMATION: Description of Artificial Sequence: Synthetic
      clone 16 VL-CK polypeptide

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Arg Val Pro Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 211
<211> LENGTH: 1338
<212> TYPE: DNA
```

<213> ORGANISM: Artificial Sequence
<220> FEATURE:
<223> OTHER INFORMATION: Description of Artificial Sequence: Synthetic clone 17 VH-CH123 polynucleotide

<400> SEQUENCE: 211

```
gaggtgcagc tgttggagtc tgggggaggc ttggtacagc ctggggggtc cctgagactc     60
tcctgtgcag cctctggatt cacctttagc agctatgcca tgagctgggt ccgccaggct    120
ccagggaagg ggctggagtg ggtctcatcg attctgggtt atggtaggca gacaatgtac    180
gcagactccg tgaagggccg gttcaccatc tccagagaca attccaagaa cacgctgtat    240
ctgcaaatga acagcctgag agccgaggac acggccgtat attactgtgc gaaatggtat    300
cgtgcttttg actactgggg ccagggaacc ctggtcaccg tctcgagcgc tagcaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtacaccctg cctccatctc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctatag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                  1338
```

<210> SEQ ID NO 212
<211> LENGTH: 446
<212> TYPE: PRT
<213> ORGANISM: Artificial Sequence
<220> FEATURE:
<223> OTHER INFORMATION: Description of Artificial Sequence: Synthetic clone 17 VH-CH123 polypeptide

<400> SEQUENCE: 212

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Leu Gly Tyr Gly Arg Gln Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Trp Tyr Arg Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 213
<211> LENGTH: 642
<212> TYPE: DNA
<213> ORGANISM: Artificial Sequence
<220> FEATURE:
<223> OTHER INFORMATION: Description of Artificial Sequence: Synthetic clone 17 VL-CK polynucleotide

<400> SEQUENCE: 213

```
gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttacta ctgtcaacag agttacagta cccctaatac gttcggccaa    300

gggaccaagg tggaaatcaa acggaccgtg gcggcgccat ctgtcttcat cttcccgcca    360

tctgatgagc agttgaaatc tggtaccgct agcgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

```
<210> SEQ ID NO 214
<211> LENGTH: 214
<212> TYPE: PRT
<213> ORGANISM: Artificial Sequence
<220> FEATURE:
<223> OTHER INFORMATION: Description of Artificial Sequence: Synthetic
      clone 17 VL-CK polypeptide

<400> SEQUENCE: 214

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 215
<211> LENGTH: 1338
```

<212> TYPE: DNA
<213> ORGANISM: Artificial Sequence
<220> FEATURE:
<223> OTHER INFORMATION: Description of Artificial Sequence: Synthetic
      clone 18 VH-CH123 polynucleotide

<400> SEQUENCE: 215

```
gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcaacg attcataaga cgggttcgcc gacatattac    180

gcagactccg tgaagggccg gttcaccatc tccagagaca attccaagaa cacgctgtat    240

ctgcaaatga acagcctgag agccgaggac acggccgtat attactgtgc gaagtctttg    300

aagtattttg actactgggg ccagggaacc ctggtcaccg tctcgagcgc tagcaccaag    360

ggcccatcgg tcttccccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gacaagaaag ttgagcccaa atcttgtgac    660

aaaactcaca catgcccacc gtgcccagca cctgaactcc tggggggacc gtcagtcttc    720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cccagccccc atcgagaaaa ccatctccaa agccaaaggg   1020

cagccccgag aaccacaggt gtacaccctg cctccatctc gggatgagct gaccaagaac   1080

caggtcagcc tgacctgcct ggtcaaaggc ttctatccca gcgacatcgc cgtggagtgg   1140

gagagcaatg ggcagccgga gaacaactac aagaccacgc ctcccgtgct ggactccgac   1200

ggctccttct tcctctatag caagctcacc gtggacaaga gcaggtggca gcaggggaac   1260

gtcttctcat gctccgtgat gcatgaggct ctgcacaacc actacacgca gaagagcctc   1320

tccctgtctc cgggtaaa                                                 1338
```

<210> SEQ ID NO 216
<211> LENGTH: 446
<212> TYPE: PRT
<213> ORGANISM: Artificial Sequence
<220> FEATURE:
<223> OTHER INFORMATION: Description of Artificial Sequence: Synthetic
      clone 18 VH-CH123 polypeptide

<400> SEQUENCE: 216

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile His Lys Thr Gly Ser Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Ser Leu Lys Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 217
<211> LENGTH: 642
<212> TYPE: DNA
<213> ORGANISM: Artificial Sequence
<220> FEATURE:
<223> OTHER INFORMATION: Description of Artificial Sequence: Synthetic
      clone 18 VL-CK polynucleotide

<400> SEQUENCE: 217

```
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatagg gcatcccatt tgcaaagtgg ggtcccatca    180
aggttcagtg gcagtggatc tgggacagat ttcactctca ccatcagcag tctgcaacct    240
gaagattttg caacttacta ctgtcaacag ccgcggagtc tgcctgctac gttcggccaa    300
gggaccaagg tggaaatcaa acggaccgtg gcggcgccat ctgtcttcat cttcccgcca    360
tctgatgagc agttgaaatc tggtaccgct agcgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 218
<211> LENGTH: 214
<212> TYPE: PRT
<213> ORGANISM: Artificial Sequence
<220> FEATURE:
<223> OTHER INFORMATION: Description of Artificial Sequence: Synthetic clone 18 VL-CK polypeptide

<400> SEQUENCE: 218

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Arg Ser Leu Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 219

```
<211> LENGTH: 1338
<212> TYPE: DNA
<213> ORGANISM: Artificial Sequence
<220> FEATURE:
<223> OTHER INFORMATION: Description of Artificial Sequence: Synthetic
      clone 21 VH-CH123 polynucleotide

<400> SEQUENCE: 219

gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcaact atttatcgtg cgggtcagaa tacaaggtac    180

gcagactccg tgaagggccg gttcaccatc tccagagaca attccaagaa cacgctgtat    240

ctgcaaatga acagcctgag agccgaggac acggccgtat attactgtgc gaaatcgagt    300

cggacttttg actactgggg ccagggaacc ctggtcaccg tctcgagcgc tagcaccaag    360

ggcccatcgg tcttccccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gacaagaaag ttgagcccaa atcttgtgac    660

aaaactcaca catgcccacc gtgcccagca cctgaactcc tggggggacc gtcagtcttc    720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cccagccccc atcgagaaaa ccatctccaa agccaaaggg   1020

cagccccgag aaccacaggt gtacaccctg cctccatctc gggatgagct gaccaagaac   1080

caggtcagcc tgacctgcct ggtcaaaggc ttctatccca gcgacatcgc cgtggagtgg   1140

gagagcaatg ggcagccgga gaacaactac aagaccacgc ctcccgtgct ggactccgac   1200

ggctccttct tcctctatag caagctcacc gtggacaaga gcaggtggca gcaggggaac   1260

gtcttctcat gctccgtgat gcatgaggct ctgcacaacc actacacgca gaagagcctc   1320

tccctgtctc cgggtaaa                                                 1338


<210> SEQ ID NO 220
<211> LENGTH: 446
<212> TYPE: PRT
<213> ORGANISM: Artificial Sequence
<220> FEATURE:
<223> OTHER INFORMATION: Description of Artificial Sequence: Synthetic
      clone 21 VH-CH123 polypeptide

<400> SEQUENCE: 220

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Tyr Arg Ala Gly Gln Asn Thr Arg Tyr Ala Asp Ser Val
    50                  55                  60

Lys Gly Arg Phe Thr Ile Ser Arg Asp Asn Ser Lys Asn Thr Leu Tyr
```

```
65                  70                  75                  80

Leu Gln Met Asn Ser Leu Arg Ala Glu Asp Thr Ala Val Tyr Tyr Cys
                85                  90                  95

Ala Lys Ser Ser Arg Thr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 221
<211> LENGTH: 642
<212> TYPE: DNA
<213> ORGANISM: Artificial Sequence
<220> FEATURE:
<223> OTHER INFORMATION: Description of Artificial Sequence: Synthetic clone 21 VL-CK polynucleotide

<400> SEQUENCE: 221

```
gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctataag gcatcctcgt tgcaaagtgg ggtcccatca    180

aggttcagtg gcagtggatc tgggacagat ttcactctca ccatcagcag tctgcaacct    240

gaagattttg caacttacta ctgtcaacag gcgacgctgc agcctcggac gttcggccaa    300

gggaccaagg tggaaatcaa acggaccgtg gcggcgccat ctgtcttcat cttcccgcca    360

tctgatgagc agttgaaatc tggtaccgct agcgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 222
<211> LENGTH: 214
<212> TYPE: PRT
<213> ORGANISM: Artificial Sequence
<220> FEATURE:
<223> OTHER INFORMATION: Description of Artificial Sequence: Synthetic clone 21 VL-CK polypeptide

<400> SEQUENCE: 222

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Lys Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Thr Leu Gln Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 223
<211> LENGTH: 1338
<212> TYPE: DNA
<213> ORGANISM: Artificial Sequence
<220> FEATURE:
<223> OTHER INFORMATION: Description of Artificial Sequence: Synthetic
      clone 23 VH-CH123 polynucleotide

<400> SEQUENCE: 223

gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcatct attagtgctt ctggtacttc tacaaattac    180

gcagactccg tgaagggccg gttcaccatc tccagagaca attccaagaa cacgctgtat    240

ctgcaaatga acagcctgag agccgaggac acggccgtat attactgtgc gaaaagtaat    300

agtgattttg actactgggg ccagggaacc ctggtcaccg tctcgagcgc tagcaccaag    360

ggcccatcgg tcttccccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gacaagaaag ttgagcccaa atcttgtgac    660

aaaactcaca catgcccacc gtgcccagca cctgaactcc tggggggacc gtcagtcttc    720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cccagccccc atcgagaaaa ccatctccaa agccaaaggg   1020

cagccccgag aaccacaggt gtacaccctg cctccatctc gggatgagct gaccaagaac   1080

caggtcagcc tgacctgcct ggtcaaaggc ttctatccca gcgacatcgc cgtggagtgg   1140

gagagcaatg ggcagccgga gaacaactac aagaccacgc ctcccgtgct ggactccgac   1200

ggctccttct tcctctatag caagctcacc gtggacaaga gcaggtggca gcaggggaac   1260

gtcttctcat gctccgtgat gcatgaggct ctgcacaacc actacacgca gaagagcctc   1320

tccctgtctc cgggtaaa                                                 1338


<210> SEQ ID NO 224
<211> LENGTH: 446
<212> TYPE: PRT
<213> ORGANISM: Artificial Sequence
<220> FEATURE:
<223> OTHER INFORMATION: Description of Artificial Sequence: Synthetic
      clone 23 VH-CH123 polypeptide

<400> SEQUENCE: 224

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ala Ser Gly Thr Ser Thr Asn Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Asn Ser Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 225
<211> LENGTH: 642
<212> TYPE: DNA
<213> ORGANISM: Artificial Sequence
<220> FEATURE:
<223> OTHER INFORMATION: Description of Artificial Sequence: Synthetic clone 23 VL-CK polynucleotide

<400> SEQUENCE: 225

```
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatggt gcatcctatt tgcaaagtgg ggtcccatca    180
aggttcagtg gcagtggatc tgggacagat ttcactctca ccatcagcag tctgcaacct    240
gaagattttg caacttacta ctgtcaacag tctggttatg atcctgctac gttcggccaa    300
gggaccaagg tggaaatcaa acggaccgtg gcggcgccat ctgtcttcat cttcccgcca    360
tctgatgagc agttgaaatc tggtaccgct agcgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 226
<211> LENGTH: 214
<212> TYPE: PRT
<213> ORGANISM: Artificial Sequence
<220> FEATURE:
<223> OTHER INFORMATION: Description of Artificial Sequence: Synthetic clone 23 VL-CK polypeptide

<400> SEQUENCE: 226

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Tyr Asp Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 227
<211> LENGTH: 1338
<212> TYPE: DNA
<213> ORGANISM: Artificial Sequence
<220> FEATURE:
<223> OTHER INFORMATION: Description of Artificial Sequence: Synthetic clone 24 VH-CH123 polynucleotide

<400> SEQUENCE: 227

```
gaggtgcagc tgttggagtc tgggggaggc ttggtacagc ctggggggtc cctgagactc     60
tcctgtgcag cctctggatt cacctttagc agctatgcca tgagctgggt ccgccaggct    120
ccagggaagg ggctggagtg ggtctcagct attgataata gtggtgctta tacatcttac    180
gcagactccg tgaagggcag gttcaccatc tccagagaca attccaagaa cacgctgtat    240
ctgcaaatga acagcctgag agccgaggac acggccgtat attactgtgc gaaaggtagt    300
tctgattttg actactgggg ccagggaacc ctggtcaccg tctcgagcgc tagcaccaag    360
ggcccatcgg tcttcccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtacaccctg cctccatctc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctatag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                 1338
```

<210> SEQ ID NO 228
<211> LENGTH: 446
<212> TYPE: PRT
<213> ORGANISM: Artificial Sequence
<220> FEATURE:
<223> OTHER INFORMATION: Description of Artificial Sequence: Synthetic clone 24 VH-CH123 polypeptide

<400> SEQUENCE: 228

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asp Asn Ser Gly Ala Tyr Thr Ser Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ser Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 229
<211> LENGTH: 642
<212> TYPE: DNA
<213> ORGANISM: Artificial Sequence
<220> FEATURE:

<223> OTHER INFORMATION: Description of Artificial Sequence: Synthetic clone 24 VL-CK polynucleotide

<400> SEQUENCE: 229

```
gacatccaga tgacccagtc tccatcctcc ctgtctgcat ctgtaggaga cagagtcacc      60

atcacttgcc gggcaagtca gagcattagc agctatttaa attggtatca gcagaaacca     120

gggaaagccc ctaagctcct gatctatggt gcatcctctt tgcaaagtgg ggtcccatca     180

aggttcagtg gcagtggatc tgggacagat ttcactctca ccatcagcag tctgcaacct     240

gaagattttg caacttacta ctgtcaacag gctggtaatg atccttctac gttcggccaa     300

gggaccaagg tggaaatcaa acggaccgtg gcggcgccat ctgtcttcat cttcccgcca     360

tctgatgagc agttgaaatc tggtaccgct agcgttgtgt gcctgctgaa taacttctat     420

cccagagagg ccaaagtaca gtggaaggtg gataacgccc tccaatcggg taactcccag     480

gagagtgtca cagagcagga cagcaaggac agcacctaca gcctcagcag caccctgacg     540

ctgagcaaag cagactacga gaaacacaaa gtctacgcct gcgaagtcac ccatcagggc     600

ctgagctcgc ccgtcacaaa gagcttcaac aggggagagt gt                        642
```

<210> SEQ ID NO 230
<211> LENGTH: 214
<212> TYPE: PRT
<213> ORGANISM: Artificial Sequence
<220> FEATURE:
<223> OTHER INFORMATION: Description of Artificial Sequence: Synthetic clone 24 VL-CK polypeptide

<400> SEQUENCE: 230

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Gly Asn Asp Pro Ser
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 231
<211> LENGTH: 1338
<212> TYPE: DNA
<213> ORGANISM: Artificial Sequence
<220> FEATURE:
<223> OTHER INFORMATION: Description of Artificial Sequence: Synthetic clone 26 VH-CH123 polynucleotide

<400> SEQUENCE: 231

```
gaggtgcagc tgttggagtc tggggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcagcg attactgcgc cgggtcctcg gacacagtac    180

gcagactccg tgaagggccg gttcaccatc tccagagaca attccaagaa cacgctgtat    240

ctgcaaatga acagcctgag agccgaggac acggccgtat attactgtgc gaaagggacg    300

cgtacgtttg actactgggg ccagggaacc ctggtcaccg tctcgagcgc tagcaccaag    360

ggcccatcgg tcttcccccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gacaagaaag ttgagcccaa atcttgtgac    660

aaaactcaca catgcccacc gtgcccagca cctgaactcc tggggggacc gtcagtcttc    720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cccagccccc atcgagaaaa ccatctccaa agccaaaggg   1020

cagccccgag aaccacaggt gtacaccctg cctccatctc gggatgagct gaccaagaac   1080

caggtcagcc tgacctgcct ggtcaaaggc ttctatccca gcgacatcgc cgtggagtgg   1140

gagagcaatg ggcagccgga gaacaactac aagaccacgc ctcccgtgct ggactccgac   1200

ggctccttct tcctctatag caagctcacc gtggacaaga gcaggtggca gcaggggaac   1260

gtcttctcat gctccgtgat gcatgaggct ctgcacaacc actacacgca gaagagcctc   1320

tccctgtctc cgggtaaa                                                 1338
```

<210> SEQ ID NO 232
<211> LENGTH: 446
<212> TYPE: PRT
<213> ORGANISM: Artificial Sequence
<220> FEATURE:
<223> OTHER INFORMATION: Description of Artificial Sequence: Synthetic clone 26 VH-CH123 polypeptide

<400> SEQUENCE: 232

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Thr Ala Pro Gly Pro Arg Thr Gln Tyr Ala Asp Ser Val
```

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Arg Thr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 233
<211> LENGTH: 642
<212> TYPE: DNA
<213> ORGANISM: Artificial Sequence

```
<220> FEATURE:
<223> OTHER INFORMATION: Description of Artificial Sequence: Synthetic
      clone 26 VL-CK polynucleotide

<400> SEQUENCE: 233

gacatccaga tgacccagtc tccatcctcc ctgtctgcat ctgtaggaga cagagtcacc      60

atcacttgcc gggcaagtca gagcattagc agctatttaa attggtatca gcagaaacca     120

gggaaagccc ctaagctcct gatctatggt gcatcccatt tgcaaagtgg ggtcccatca     180

aggttcagtg gcagtggatc tgggacagat ttcactctca ccatcagcag tctgcaacct     240

gaagattttg caacttacta ctgtcaacag ccgacgacta cgcctcgtac gttcggccaa     300

gggaccaagg tggaaatcaa acggaccgtg gcggcgccat ctgtcttcat cttcccgcca     360

tctgatgagc agttgaaatc tggtaccgct agcgttgtgt gcctgctgaa taacttctat     420

cccagagagg ccaaagtaca gtggaaggtg gataacgccc tccaatcggg taactcccag     480

gagagtgtca cagagcagga cagcaaggac agcacctaca gcctcagcag caccctgacg     540

ctgagcaaag cagactacga gaaacacaaa gtctacgcct gcgaagtcac ccatcagggc     600

ctgagctcgc ccgtcacaaa gagcttcaac aggggagagt gt                        642


<210> SEQ ID NO 234
<211> LENGTH: 214
<212> TYPE: PRT
<213> ORGANISM: Artificial Sequence
<220> FEATURE:
<223> OTHER INFORMATION: Description of Artificial Sequence: Synthetic
      clone 26 VL-CK polypeptide

<400> SEQUENCE: 234

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Thr Thr Thr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

210

<210> SEQ ID NO 235
<211> LENGTH: 1338
<212> TYPE: DNA
<213> ORGANISM: Artificial Sequence
<220> FEATURE:
<223> OTHER INFORMATION: Description of Artificial Sequence: Synthetic clone 27 VH-CH123 polynucleotide

<400> SEQUENCE: 235
gaggtgcagc tgttggagtc tgggggaggc ttggtacagc ctggggggtc cctgagactc 60
tcctgtgcag cctctggatt cacctttagc agctatgcca tgagctgggt ccgccaggct 120
ccagggaagg ggctggagtg ggtctcaaag attaagccgc agggtgatgc gacacggtac 180
gcagactccg tgaagggccg gttcaccatc tccagagaca attccaagaa cacgctgtat 240
ctgcaaatga acagcctgag agccgaggac acggccgtat attactgtgc gaaaggggct 300
cggaggtttg actactgggg ccagggaacc ctggtcaccg tctcgagcgc tagcaccaag 360
ggcccatcgg tcttccccct ggcaccctcc tccaagagca cctctggggg cacagcggcc 420
ctgggctgcc tggtcaagga ctacttcccc gaaccggtga cggtgtcgtg gaactcaggc 480
gccctgacca gcggcgtgca caccttcccg gctgtcctac agtcctcagg actctactcc 540
ctcagcagcg tggtgaccgt gccctccagc agcttgggca cccagaccta catctgcaac 600
gtgaatcaca agcccagcaa caccaaggtg gacaagaaag ttgagcccaa atcttgtgac 660
aaaactcaca catgcccacc gtgcccagca cctgaactcc tggggggacc gtcagtcttc 720
ctcttccccc caaaacccaa ggacaccctc atgatctccc ggacccctga ggtcacatgc 780
gtggtggtgg acgtgagcca cgaagaccct gaggtcaagt tcaactggta cgtggacggc 840
gtggaggtgc ataatgccaa gacaaagccg cgggaggagc agtacaacag cacgtaccgt 900
gtggtcagcg tcctcaccgt cctgcaccag gactggctga atggcaagga gtacaagtgc 960
aaggtctcca acaaagccct cccagccccc atcgagaaaa ccatctccaa agccaaaggg 1020
cagccccgag aaccacaggt gtacaccctg cctccatctc gggatgagct gaccaagaac 1080
caggtcagcc tgacctgcct ggtcaaaggc ttctatccca gcgacatcgc cgtggagtgg 1140
gagagcaatg ggcagccgga gaacaactac aagaccacgc ctcccgtgct ggactccgac 1200
ggctccttct tcctctatag caagctcacc gtggacaaga gcaggtggca gcaggggaac 1260
gtcttctcat gctccgtgat gcatgaggct ctgcacaacc actacacgca gaagagcctc 1320
tccctgtctc cgggtaaa 1338

<210> SEQ ID NO 236
<211> LENGTH: 446
<212> TYPE: PRT
<213> ORGANISM: Artificial Sequence
<220> FEATURE:
<223> OTHER INFORMATION: Description of Artificial Sequence: Synthetic clone 27 VH-CH123 polypeptide

<400> SEQUENCE: 236

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

```
Ser Lys Ile Lys Pro Gln Gly Asp Ala Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Arg Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 237
<211> LENGTH: 642
<212> TYPE: DNA

```
<213> ORGANISM: Artificial Sequence
<220> FEATURE:
<223> OTHER INFORMATION: Description of Artificial Sequence: Synthetic
      clone 27 VL-CK polynucleotide

<400> SEQUENCE: 237

gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatcgt gcatcccgtt tgcaaagtgg ggtcccatca    180

aggttcagtg gcagtggatc tgggacagat ttcactctca ccatcagcag tctgcaacct    240

gaagattttg caacttacta ctgtcaacag actaagcggc ctcctcagac gttcggccaa    300

gggaccaagg tggaaatcaa acggaccgtg gcggcgccat ctgtcttcat cttcccgcca    360

tctgatgagc agttgaaatc tggtaccgct agcgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                        642


<210> SEQ ID NO 238
<211> LENGTH: 214
<212> TYPE: PRT
<213> ORGANISM: Artificial Sequence
<220> FEATURE:
<223> OTHER INFORMATION: Description of Artificial Sequence: Synthetic
      clone 27 VL-CK polypeptide

<400> SEQUENCE: 238

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Lys Arg Pro Pro Gln
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210


<210> SEQ ID NO 239
<211> LENGTH: 1338
<212> TYPE: DNA
<213> ORGANISM: Artificial Sequence
<220> FEATURE:
<223> OTHER INFORMATION: Description of Artificial Sequence: Synthetic
      clone 41 VH-CH123 polynucleotide

<400> SEQUENCE: 239

gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcaacg attaagcaga cgggtacgca gacaaagtac    180

gcagactccg tgaagggccg gttcaccatc tccagagaca attccaagaa cacgctgtat    240

ctgcaaatga acagcctgag agccgaggac acggccgtat attactgtgc gaaaagtggt    300

cggcggtttg actactgggg ccagggaacc ctggtcaccg tctcgagcgc tagcaccaag    360

ggcccatcgg tcttccccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gacaagaaag ttgagcccaa atcttgtgac    660

aaaactcaca catgcccacc gtgcccagca cctgaactcc tggggggacc gtcagtcttc    720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cccagccccc atcgagaaaa ccatctccaa agccaaaggg   1020

cagccccgag aaccacaggt gtacaccctg cctccatctc gggatgagct gaccaagaac   1080

caggtcagcc tgacctgcct ggtcaaaggc ttctatccca gcgacatcgc cgtggagtgg   1140

gagagcaatg ggcagccgga gaacaactac aagaccacgc ctcccgtgct ggactccgac   1200

ggctccttct tcctctatag caagctcacc gtggacaaga gcaggtggca gcaggggaac   1260

gtcttctcat gctccgtgat gcatgaggct ctgcacaacc actacacgca gaagagcctc   1320

tccctgtctc cgggtaaa                                                  1338


<210> SEQ ID NO 240
<211> LENGTH: 446
<212> TYPE: PRT
<213> ORGANISM: Artificial Sequence
<220> FEATURE:
<223> OTHER INFORMATION: Description of Artificial Sequence: Synthetic
      clone 41 VH-CH123 polypeptide

<400> SEQUENCE: 240

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Thr Ile Lys Gln Thr Gly Thr Gln Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Arg Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 241
<211> LENGTH: 642

<212> TYPE: DNA
<213> ORGANISM: Artificial Sequence
<220> FEATURE:
<223> OTHER INFORMATION: Description of Artificial Sequence: Synthetic
clone 41 VL-CK polynucleotide

<400> SEQUENCE: 241

```
gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctataag gcatcccgtt tgcaaagtgg ggtcccatca    180

aggttcagtg gcagtggatc tgggacagat ttcactctca ccatcagcag tctgcaacct    240

gaagattttg caacttacta ctgtcaacag gctagtctta cgcctccgac gttcggccaa    300

gggaccaagg tggaaatcaa acggaccgtg gcggcgccat ctgtcttcat cttcccgcca    360

tctgatgagc agttgaaatc tggtaccgct agcgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                        642
```

<210> SEQ ID NO 242
<211> LENGTH: 214
<212> TYPE: PRT
<213> ORGANISM: Artificial Sequence
<220> FEATURE:
<223> OTHER INFORMATION: Description of Artificial Sequence: Synthetic
clone 41 VL-CK polypeptide

<400> SEQUENCE: 242

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Lys Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Leu Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210
```

ANTIBODIES TO HUMAN RESISTIN

CROSS-REFERENCE TO RELATED APPLICATIONS

This application is a 35 U.S.C. § 371 U.S. national entry of International Application PCT/US2014/042706, having an international filing date of Jun. 17, 2014, which claims the benefit of U.S. Provisional Application No. 61/835,855, filed Jun. 17, 2013, the content of each of the aforementioned applications is herein incorporated by reference in their entirety.

STATEMENT OF GOVERNMENTAL INTEREST

This invention was made with government support under grant no. P50HL107182 awarded by the National Institutes of Health. The government has certain rights in the invention.

FIELD OF THE INVENTION

The present invention relates to the field of pulmonary, cardiac and inflammatory disorders. More specifically, the present invention provides methods and compositions for treating disorders associated with Resistin.

INCORPORATION-BY-REFERENCE OF MATERIAL SUBMITTED ELECTRONICALLY

This application contains a sequence listing. It has been submitted electronically via EFS-Web as an ASCII text file entitled "P12269-02_Sequence_Listing.txt." The sequence listing is 291,637 bytes in size, and was created on Jun. 17, 2014. It is hereby incorporated by reference in its entirety.

BACKGROUND OF THE INVENTION

Resistin and Resistin-Like Molecule-Beta (RELM-beta) are the human analogs of a recently identified family of secreted proteins containing a conserved cysteine-rich C-terminus. The RELM family consists of Resistin (also called FIZZ3), RELM-alpha (FIZZ1), RELM-beta (FIZZ2) and RELM-gamma (FIZZ4). In human there are two isoforms, Resistin and RELM-Beta. The RELM family of proteins has been implicated in several human disease states including, but not limited to, pulmonary hypertension, cardiac hypertrophy and failure, asthma, lung inflammation, sepsis, acute lung injury, respiratory distress syndrome, pulmonary fibrosis, scleroderma, arteriosclerosis, chronic obstructive lung disease/emphysema, normal and abnormal wound healing, cancer, cell proliferation, stem cell growth and differentiation, diabetic retinopathy, and insulin resistance. There is a continuing need in the art to provide therapies for diseases, disorder and conditions mediated by the RELM family of proteins.

SUMMARY OF THE INVENTION

The present invention is based, at least in part, on the development of antibodies to Resistin. Thus, in particular embodiments, the present invention provides isolated antibodies that bind human Resistin. Such antibodies may also be cross-reactive with RELMB. In particular embodiments, the antibodies are recombinant or otherwise non-naturally occurring antibodies. In other embodiments, the present invention provides nucleotide sequences that encode an antibody that binds human Resistin. The present invention further provides amino acid sequences that encode an antibody that binds human Resistin. The antibody can be a single chain variable fragment (scFv), a dimeric scFv, a Fab, a Fab', a F(ab')2 fragment or a full length antibody.

In specific embodiments, the antibody comprises a variable heavy chain comprising SEQ ID NO:3, SEQ ID NO:13, SEQ ID NO:23, SEQ ID NO:33, SEQ ID NO:43, SEQ ID NO:53, SEQ ID NO:63, SEQ ID NO:73, SEQ ID NO:83, SEQ ID NO:93, SEQ ID NO:103, SEQ ID NO:113, SEQ ID NO:123, SEQ ID NO:133, SEQ ID NO:143, SEQ ID NO:153, SEQ ID NO:163, or fragments thereof. In other embodiments, the antibody comprises a variable heavy chain that is at least 90% identical to SEQ ID NO:3, SEQ ID NO:13, SEQ ID NO:23, SEQ ID NO:33, SEQ ID NO:43, SEQ ID NO:53, SEQ ID NO:63, SEQ ID NO:73, SEQ ID NO:83, SEQ ID NO:93, SEQ ID NO:103, SEQ ID NO:113, SEQ ID NO:123, SEQ ID NO:133, SEQ ID NO:143, SEQ ID NO:153, SEQ ID NO:163, or fragments thereof.

In certain embodiments, the antibody comprises a light chain comprising SEQ ID NO:7, SEQ ID NO:17, SEQ ID NO:27, SEQ ID NO:37, SEQ ID NO:47, SEQ ID NO:57, SEQ ID NO:67, SEQ ID NO:77, SEQ ID NO:87, SEQ ID NO:97, SEQ ID NO:107, SEQ ID NO:117, SEQ ID NO:127, SEQ ID NO:137, SEQ ID NO:147, SEQ ID NO:157, SEQ ID NO:167, or fragments thereof. Alternatively, the antibody comprises a light chain that is at least 90% identical to SEQ ID NO:7, SEQ ID NO:17, SEQ ID NO:27, SEQ ID NO:37, SEQ ID NO:47, SEQ ID NO:57, SEQ ID NO:67, SEQ ID NO:77, SEQ ID NO:87, SEQ ID NO:97, SEQ ID NO:107, SEQ ID NO:117, SEQ ID NO:127, SEQ ID NO:137, SEQ ID NO:147, SEQ ID NO:157, SEQ ID NO:167, or fragments thereof.

The present invention also provides antibodies in which the variable domain of the heavy chain comprises one or more complementarity determining regions (CDRs) selected from the group consisting of SEQ ID NO:4, SEQ ID NO:5, SEQ ID NO:6, SEQ ID NO:14, SEQ ID NO:15, SEQ ID NO:16, SEQ ID NO:24, SEQ ID NO:25, SEQ ID NO:26, SEQ ID NO:34, SEQ ID NO:35, SEQ ID NO:36, SEQ ID NO:44, SEQ ID NO:45, SEQ ID NO:46, SEQ ID NO:54, SEQ ID NO:55, SEQ ID NO:56, SEQ ID NO:64, SEQ ID NO:65, SEQ ID NO:66, SEQ ID NO:74, SEQ ID NO:75, SEQ ID NO:76, SEQ ID NO:4, SEQ ID NO:85, SEQ ID NO:86, SEQ ID NO:94, SEQ ID NO:95, SEQ ID NO:96, SEQ ID NO:104, SEQ ID NO:105, SEQ ID NO:106, SEQ ID NO:114, SEQ ID NO:115, SEQ ID NO:116, SEQ ID NO:124, SEQ ID NO:125, SEQ ID NO:126, SEQ ID NO:134, SEQ ID NO:135, SEQ ID NO:136, SEQ ID NO:144, SEQ ID NO:145, SEQ ID NO:146, SEQ ID NO:154, SEQ ID NO:155, SEQ ID NO:156, SEQ ID NO:164, SEQ ID NO:165, SEQ ID NO:166, and fragments thereof. In other embodiments, the variable domain of the heavy chain comprises one or more complementarity determining regions (CDRs) that are at least 90% identical to a CDR selected from the group consisting of SEQ ID NO:4, SEQ ID NO:15, SEQ ID NO:6, SEQ ID NO:14, SEQ ID NO:5, SEQ ID NO:16, SEQ ID NO:24, SEQ ID NO:25, SEQ ID NO:26, SEQ ID NO:34, SEQ ID NO:35, SEQ ID NO:36, SEQ ID NO:44, SEQ ID NO:45, SEQ ID NO:46, SEQ ID NO:54, SEQ ID NO:55, SEQ ID NO:56, SEQ ID NO:64, SEQ ID NO:65, SEQ ID NO:66, SEQ ID NO:74, SEQ ID NO:75, SEQ ID NO:76, SEQ ID NO:4, SEQ ID NO:85, SEQ ID NO:86, SEQ ID NO:94, SEQ ID NO:95, SEQ ID NO:96, SEQ ID NO:104, SEQ ID NO:105, SEQ ID NO:106, SEQ ID NO:114, SEQ ID NO:115, SEQ ID NO:116, SEQ ID NO:124, SEQ ID NO:125, SEQ ID NO:126, SEQ ID NO:134, SEQ ID NO:135, SEQ ID NO:136, SEQ ID NO:144, SEQ ID NO:145, SEQ ID NO:146, SEQ ID NO:154, SEQ ID NO:155, SEQ ID NO:156, SEQ ID NO:164, SEQ ID NO:165, SEQ ID NO:166, and fragments thereof.

The present invention also provides antibodies in which the variable domain of the light chain comprises one or more CDRs selected from the group consisting of SEQ ID NO:8, SEQ ID NO:9, SEQ ID NO:10, SEQ ID NO:18, SEQ ID NO:19, SEQ ID NO:20, SEQ ID NO:28, SEQ ID NO:29, SEQ ID NO:30, SEQ ID NO:38, SEQ ID NO:39, SEQ ID NO:40, SEQ ID NO:48, SEQ ID NO:49, SEQ ID NO:50, SEQ ID NO:58, SEQ ID NO:59, SEQ ID NO:60, SEQ ID NO:68, SEQ ID NO:69, SEQ ID NO:70, SEQ ID NO:78, SEQ ID NO:79, SEQ ID NO:80, SEQ ID NO:88, SEQ ID NO:89, SEQ ID NO:90, SEQ ID NO:98, SEQ ID NO:99, SEQ ID NO:100, SEQ ID NO:108, SEQ ID NO:109, SEQ ID NO:110, SEQ ID NO:118, SEQ ID NO:119, SEQ ID NO:120, SEQ ID NO:128, SEQ ID NO:129, SEQ ID NO:130, SEQ ID NO:138, SEQ ID NO:139, SEQ ID NO:140, SEQ ID NO:148, SEQ ID NO:149, SEQ ID NO:150, SEQ ID NO:158, SEQ ID NO:159, SEQ ID NO:160, SEQ ID NO:168, SEQ ID NO:169, SEQ ID NO:170, and fragments thereof. In alternative embodiments, the variable domain of the light chain comprises one or more CDRs that are at least 90% identical to a CDR selected from the group consisting of SEQ ID NO:8, SEQ ID NO:9, SEQ ID NO:10, SEQ ID NO:18, SEQ ID NO:19, SEQ ID NO:20, SEQ ID NO:28, SEQ ID NO:29, SEQ ID NO:30, SEQ ID NO:38, SEQ ID NO:39, SEQ ID NO:40, SEQ ID NO:48, SEQ ID NO:49, SEQ ID NO:50, SEQ ID NO:58, SEQ ID NO:59, SEQ ID NO:60, SEQ ID NO:68, SEQ ID NO:69, SEQ ID NO:70, SEQ ID NO:78, SEQ ID NO:79, SEQ ID NO:80, SEQ ID NO:88, SEQ ID NO:89, SEQ ID NO:90, SEQ ID NO:98, SEQ ID NO:99, SEQ ID NO:100, SEQ ID NO:108, SEQ ID NO:109, SEQ ID NO:110, SEQ ID NO:118, SEQ ID NO:119, SEQ ID NO:120, SEQ ID NO:128, SEQ ID NO:129, SEQ ID NO:130, SEQ ID NO:138, SEQ ID NO:139, SEQ ID NO:140, SEQ ID NO:148, SEQ ID NO:149, SEQ ID NO:150, SEQ ID NO:158, SEQ ID NO:159, SEQ ID NO:160, SEQ ID NO:168, SEQ ID NO:169, SEQ ID NO:170, and fragments thereof.

In specific embodiments, the present invention provides an scfv that binds human Resistin, wherein the scfv is encoded by SEQ ID NO:1, SEQ ID NO:11, SEQ ID NO:21, SEQ ID NO:31, SEQ ID NO:41, SEQ ID NO:51, SEQ ID NO:61, SEQ ID NO:71, SEQ ID NO:81, SEQ ID NO:91, SEQ ID NO:101, SEQ ID NO:111, SEQ ID NO:121, SEQ ID NO:131, SEQ ID NO:141, SEQ ID NO:151, SEQ ID NO:161 or fragments thereof. In other embodiments, the scfv is encoded by nucleotide sequence that is at least 90% identical to SEQ ID NO:1, SEQ ID NO:11, SEQ ID NO:21, SEQ ID NO:31, SEQ ID NO:41, SEQ ID NO:51, SEQ ID NO:61, SEQ ID NO:71, SEQ ID NO:81, SEQ ID NO:91, SEQ ID NO:101, SEQ ID NO:111, SEQ ID NO:121, SEQ ID NO:131, SEQ ID NO:141, SEQ ID NO:151, SEQ ID NO:161 or fragments thereof.

The present invention also provides an scfv that binds human Resistin, wherein the scfv comprises SEQ ID NO:2, SEQ ID NO:12, SEQ ID NO:22, SEQ ID NO:32, SEQ ID NO:42, SEQ ID NO:52, SEQ ID NO:62, SEQ ID NO:72, SEQ ID NO:82, SEQ ID NO:92, SEQ ID NO:102, SEQ ID NO:112, SEQ ID NO:122, SEQ ID NO:132, SEQ ID NO:142, SEQ ID NO:152, SEQ ID NO:162 or fragments thereof. In alternative embodiments, the scfv comprises an amino acid sequence that is at least 90% identical to SEQ ID NO:2, SEQ ID NO:12, SEQ ID NO:22, SEQ ID NO:32, SEQ ID NO:42, SEQ ID NO:52, SEQ ID NO:62, SEQ ID NO:72, SEQ ID NO:82, SEQ ID NO:92, SEQ ID NO:102, SEQ ID NO:112, SEQ ID NO:122, SEQ ID NO:132, SEQ ID NO:142, SEQ ID NO:152, SEQ ID NO:162 or fragments thereof.

The antibodies of the present invention can further comprise a constant domain comprising SEQ ID NO:172, SEQ ID NO:174 or a fragment thereof. In other embodiments, the antibodies can further comprise a constant domain that is at least 90% identical to SEQ ID NO:172, SEQ ID NO:174 or a fragment thereof.

In specific embodiments, the present invention also provides a Resistin antibody comprising a heavy chain selected from the group consisting of SEQ ID NO:176, SEQ ID NO:180, SEQ ID NO:184, SEQ ID NO:188, SEQ ID NO:192, SEQ ID NO:196, SEQ ID NO:200, SEQ ID NO:204, SEQ ID NO:208, SEQ ID NO:212, SEQ ID NO:216, SEQ ID NO:220, SEQ ID NO:224, SEQ ID NO:228, SEQ ID NO:232, SEQ ID NO:236, and SEQ ID NO:240. In additional embodiments, a Resistin antibody comprises a light chain selected from the group consisting of SEQ ID NO:178, SEQ ID NO:182, SEQ ID NO:186, SEQ ID NO:190, SEQ ID NO:194, SEQ ID NO:198, SEQ ID NO:202, SEQ ID NO:206, SEQ ID NO:210, SEQ ID NO:214, SEQ ID NO:218, SEQ ID NO:222, SEQ ID NO:226, SEQ ID NO:230, SEQ ID NO:234, SEQ ID NO:238, and SEQ ID NO: 242. In further embodiments, the present invention provides a Resistin antibody comprising (a) a heavy chain selected from the group consisting of SEQ ID NO:176, SEQ ID NO:180, SEQ ID NO:184, SEQ ID NO:188, SEQ ID NO:192, SEQ ID NO:196, SEQ ID NO:200, SEQ ID NO:204, SEQ ID NO:208, SEQ ID NO:212, SEQ ID NO:216, SEQ ID NO:220, SEQ ID NO:224, SEQ ID NO:228, SEQ ID NO:232, SEQ ID NO:236, and SEQ ID NO:240 and (b) a light chain selected from the group consisting of SEQ ID NO:178, SEQ ID NO:182, SEQ ID NO:186, SEQ ID NO:190, SEQ ID NO:194, SEQ ID NO:198, SEQ ID NO:202, SEQ ID NO:206, SEQ ID NO:210, SEQ ID NO:214, SEQ ID NO:218, SEQ ID NO:222, SEQ ID NO:226, SEQ ID NO:230, SEQ ID NO:234, SEQ ID NO:238, and SEQ ID NO: 242.

In several embodiments, the present invention provides Resistin antibodies that are also cross-reactive with Resistin Like Molecule Beta (RELMβ). In other embodiments, Resistin scfv are also cross-reactive with RELMβ. In further embodiments, the antibodies and/or fragments thereof are recombinant.

In another aspect, the present invention provides methods for using the antibodies described herein. In particular embodiments, the present invention provides a method for treating a disease, disorder or condition mediated by human Resistin in a patient comprising the step of administering to the patient an antibody an scfv described herein. In specific embodiments, the disease, disorder or condition is one or more of pulmonary hypertension, cardiac hypertrophy and failure, asthma, lung inflammation, sepsis, acute lung injury, respiratory distress syndrome, pulmonary fibrosis, scleroderma, arteriosclerosis, chronic obstructive lung disease/emphysema, normal and abnormal wound healing, cancer, cell proliferation, stem cell growth and differentiation, diabetic retinopathy, and insulin resistance.

BRIEF DESCRIPTION OF THE FIGURES

FIG. 8 shows the plate layout for the hResistin antibody screen of Ab1, Ab13, Ab17, Ab21, Ab31 and R&D antibody. A-5, B-2, C-1, and D-0.5 μg/ml Ab concentrations.

FIG. 10 shows the constructs for human IgG1. CH123 is the heavy constant region. CK is the light constant region.

FIG. 11 is a table showing a quality control rIgG ELISA of 17 anti-human Resistin IgGs.

FIG. 12 is a table showing ELISA results.

DETAILED DESCRIPTION OF THE INVENTION

Figure 1:
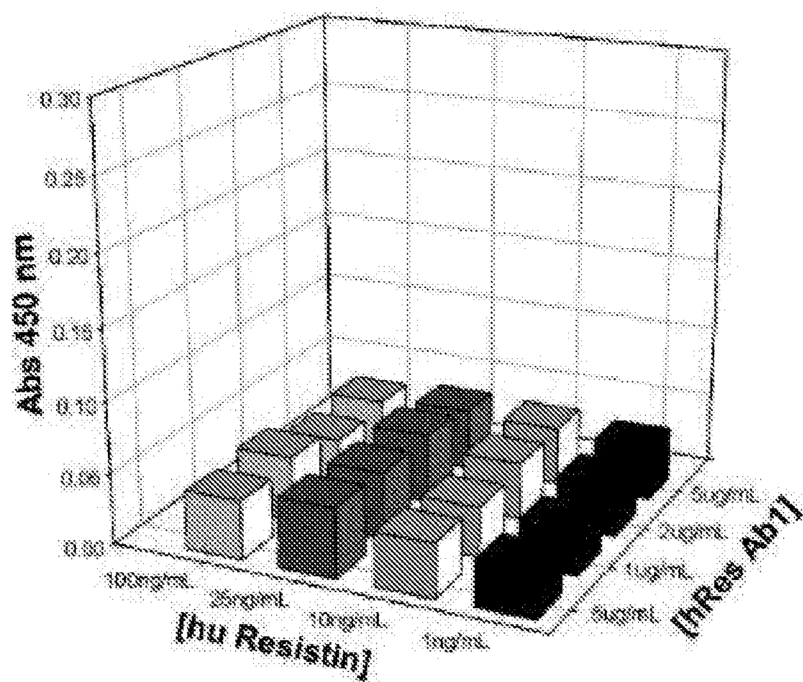
FIG. 1 is a graph showing the binding reactivity of Ab1 to human Resistin (hResistin) at absorbance 450 nm.
Figure 2:
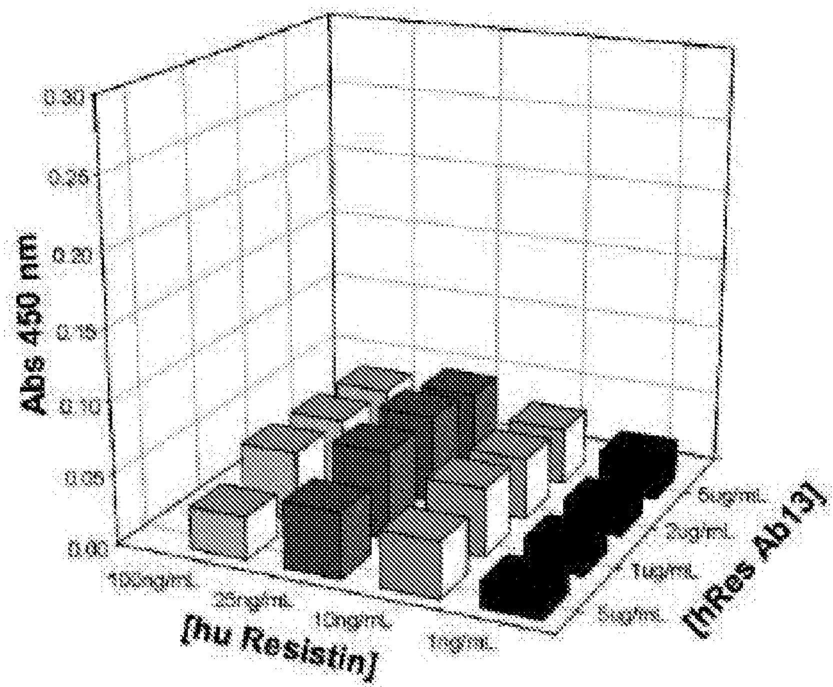
FIG. 2 is a graph showing the binding reactivity of Ab13 to human Resistin (hResistin) at absorbance 450 nm.
Figure 3:
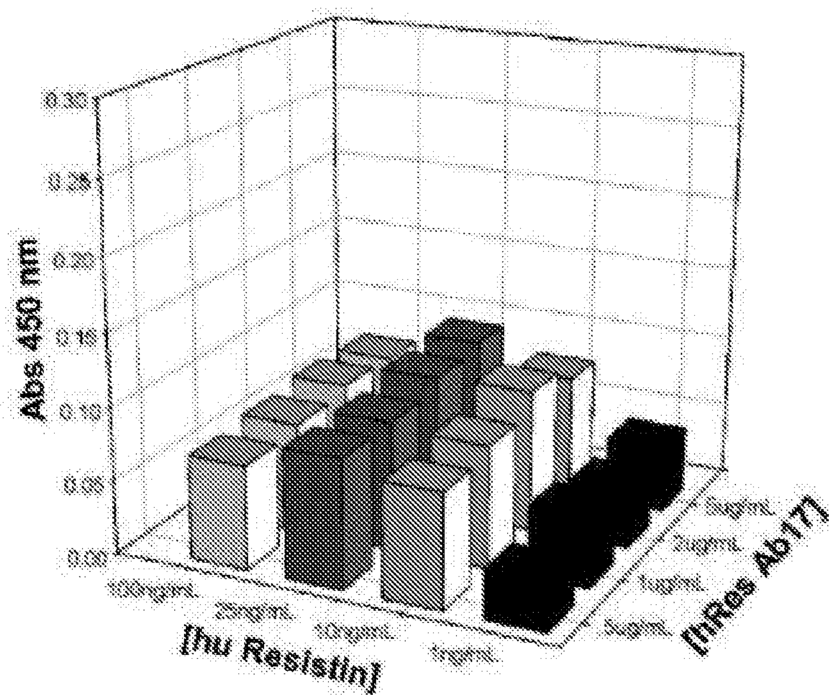
FIG. 3 is a graph showing the binding reactivity of Ab17 to human Resistin (hResistin) at absorbance 450 nm.
Figure 4:
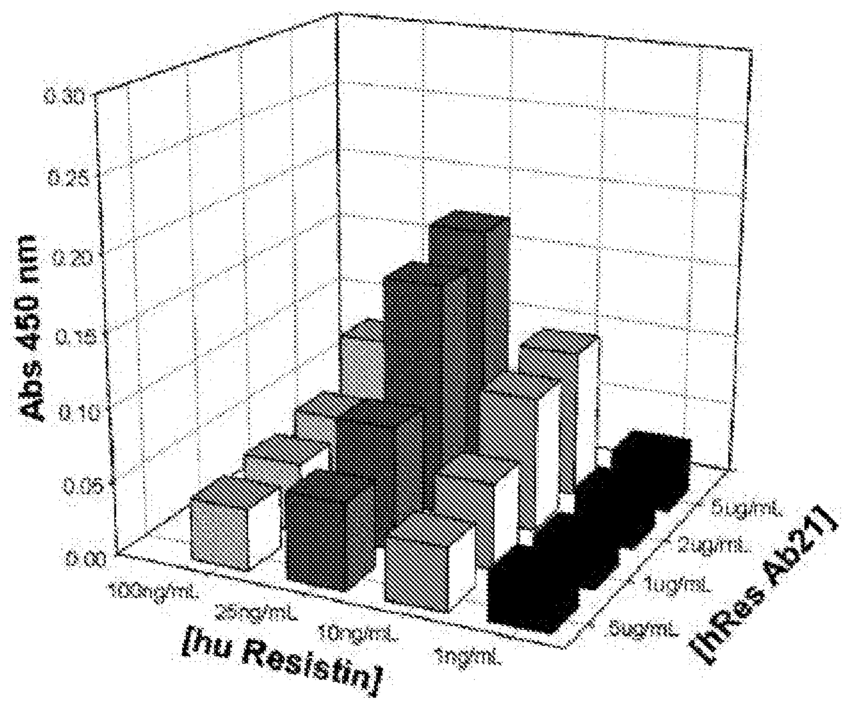
FIG. 4 is a graph showing the binding reactivity of Ab21 to human Resistin (hResistin) at absorbance 450 nm.
Figure 5:
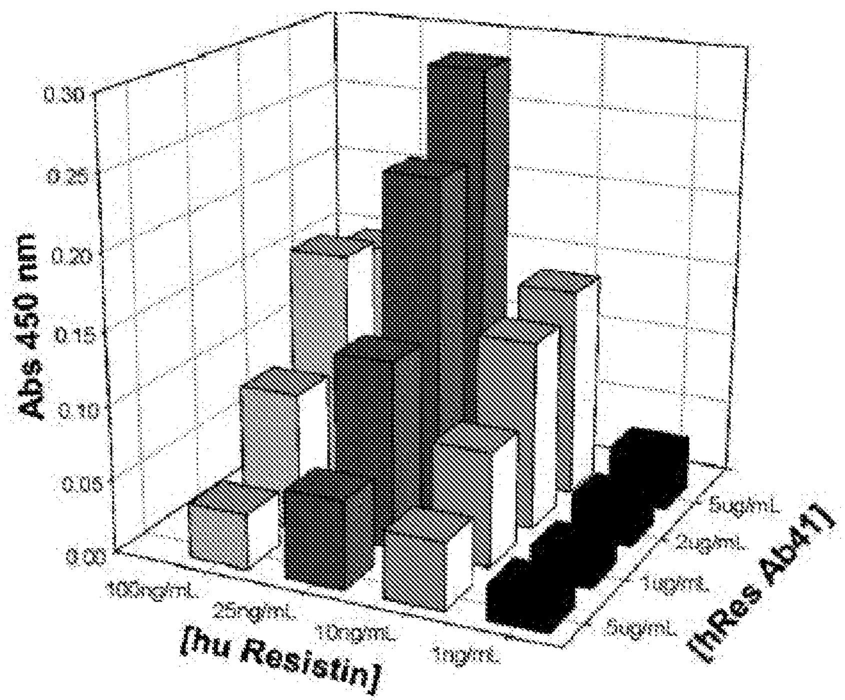
FIG. 5 is a graph showing the binding reactivity of Ab41 to human Resistin (hResistin) at absorbance 450 nm.
Figure 6:
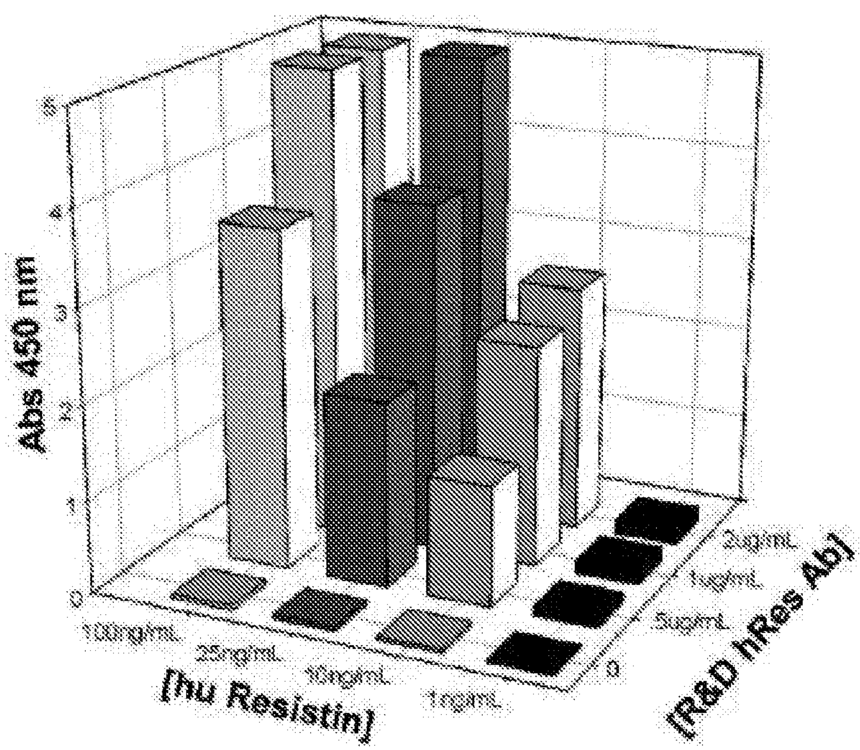
FIG. 6 is a graph showing the binding reactivity of R&D Ab to human Resistin (hResistin) at absorbance 450 nm.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, gamma-carboxyglutamate, and O-phosphoserine, phosphothreonine.

An "amino acid analog" refers to a compound that has the same basic chemical structure as a naturally occurring amino acid, i.e., a carbon that is bound to a hydrogen, a carboxyl group, an amino group, and an R group (e.g., homoserine, norleucine, methionine sulfoxide, methionine methyl sulfonium), but that contains some alteration not found in a naturally occurring amino acid (e.g., a modified side chain). Amino acids and analogs are well known in the art. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The term "amino acid mimetic" refers to chemical compounds that have a structure that is different from the general chemical structure of an amino acid, but that function in a manner similar to a naturally occurring amino acid Amino acid analogs may have modified R groups (for example, norleucine) or modified peptide backbones, but retain the same basic chemical structure as a naturally occurring amino acid. In certain embodiments, an amino acid analog is a D-amino acid, a beta-amino acid, or an N-methyl amino acid.

By "antibody" is meant any immunoglobulin polypeptide, or fragment thereof, having immunogen binding ability. As used herein, the terms "antibody fragments", "fragment", or "fragment thereof" refer to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments. In most embodiments, the terms also refer to fragments that bind an antigen of a target molecule (e.g., Resistin) and can be referred to as "antigen-binding fragments."

The term "conjugate" refers to a complex of two molecules linked together, for example, linked together by a covalent bond. In one embodiment, an antibody is linked to an effector molecule; for example, an antibody that specifically binds to Resistin covalently linked to an effector molecule. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

The terms "conjugating," "joining," "bonding," "labeling" or "linking" refer to making two molecules into one contiguous molecule; for example, linking two polypeptides into one contiguous polypeptide, or covalently attaching an effector molecule or detectable marker radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Conservative variants: "Conservative" amino acid substitutions are those substitutions that do not substantially decrease the binding affinity of an antibody for an antigen (for example, the binding affinity of an antibody for Resistin). For example, a human antibody that specifically binds Resistin can include at most about 1, at most about 2, at most about 5, at most about 10, or at most about 1 5 conservative substitutions and specifically bind the Resistin polypeptide. The term conservative variation also includes the use of a substituted amino acid in place of an unsubstituted parent amino acid, provided that antibody retains binding affinity for Resistin. Non-conservative substitutions are those that reduce an activity or binding to Resistin.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (I), Lysine ( );
5) Isoleucine (I), Leucine (L), Methionine (M), Valine (V); and
6) Phenylalanine (F), Tyrosine (Y), Tryptophan (W).

An "effector molecule" means a molecule intended to have or produce a desired effect; for example, a desired effect on a cell to which the effector molecule is targeted. Effector molecules include such molecules as polypeptides, radioisotopes and small molecules. Non-limiting examples of effector molecules include toxins, chemotherapeutic agents and anti-angiogenic agents. The skilled artisan will understand that some effector molecules may have or produce more than one desired effect. In one example, an effector molecule is the portion of a chimeric molecule, for example a chimeric molecule that includes a disclosed antibody or fragment thereof, that is intended to have a desired effect on a cell to which the chimeric molecule is targeted.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. An antigenic determinant can compete with the intact antigen (i.e., the "immunogen" used to elicit the immune response) for binding to an antibody.

By "an effective amount" is meant the amount of a required to ameliorate the symptoms of a disease relative to an untreated patient. The effective amount of active compound(s) used to practice the present invention for therapeutic treatment of a vascular disease varies depending upon the manner of administration, the age, body weight, and general health of the subject. Ultimately, the attending physician or veterinarian will decide the appropriate amount and dosage regimen. Such amount is referred to as an "effective" amount.

An "expression vector" is a nucleic acid construct, generated recombinantly or synthetically, bearing a series of specified nucleic acid elements that enable transcription of a particular gene in a host cell. Typically, gene expression is placed under the control of certain regulatory elements, including constitutive or inducible promoters, tissue-preferred regulatory elements, and enhancers.

By "fragment" is meant a portion (e.g., at least about 5, 10, 25, 50, 100, 125, 150, 200, 250, 300, 350, 400, or 500 amino acids or nucleic acids) of a protein or nucleic acid molecule that is substantially identical to a reference protein or nucleic acid and retains at least one biological activity of the reference. In some embodiments the portion retains at least 50%, 75%, or 80%, or more preferably 90%, 95%, or even 99% of the biological activity of the reference protein or nucleic acid described herein.

A "host cell" is any prokaryotic or eukaryotic cell that contains either a cloning vector or an expression vector. This term also includes those prokaryotic or eukaryotic cells that have been genetically engineered to contain the cloned gene(s) in the chromosome or genome of the host cell.

As used herein, "humanized" forms of non-human (e.g., murine) antibodies are chimeric antibodies that contain minimal sequence, or no sequence, derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues that are not found in the recipient antibody or in the donor antibody. These modifications are generally made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FR residues are those of a human immunoglobulin sequence. The humanized antibody can also comprise at least a portion of an immunoglobulin constant region (Fc), typically that of a human immunoglobulin. Examples of methods used to generate humanized antibodies are described in U.S. Pat. No. 5,225,539.

The term "human antibody" as used herein means an antibody produced by a human or an antibody having an amino acid sequence corresponding to an antibody produced by a human made using any of the techniques known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

"Hybrid antibodies" are immunoglobulin molecules in which pairs of heavy and light chains from antibodies with different antigenic determinant regions are assembled together so that two different epitopes or two different antigens can be recognized and bound by the resulting tetramer.

The terms "isolated," "purified," or "biologically pure" refer to material that is free to varying degrees from components which normally accompany it as found in its native state. Various levels of purity may be applied as needed according to this invention in the different methodologies set forth herein; the customary purity standards known in the art may be used if no standard is otherwise specified. Indeed, the term "purified" does not require the material to be present in a form exhibiting absolute purity, exclusive of the presence of other compounds. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. A isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

By "modulation" is meant a change (increase or decrease) in the expression level or biological activity of a gene or polypeptide as detected by standard methods known in the art. As used herein, modulation includes at least about 10% change, 25%, 40%, 50% or a greater change in expression levels or biological activity (e.g., about 75%, 85%, 95% or more).

The term "mimetic" means an agent having a structure that is different from the general chemical structure of a reference agent, but that has at least one biological function of the reference.

The term "neutralizing antibody" refers to an antibody that is able to specifically bind to a target protein in such a way as to inhibit a biological function associated with that target protein. In general, any protein that can perform this type of specific blocking activity is considered a neutralizing protein; neutralizing antibodies are therefore a specific class of neutralizing protein.

The term "nucleic acid" refers to an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. Such modified or substituted oligonucleotides are often preferred over native forms because of properties such as, for example, enhanced stability in the presence of nucleases.

Specific examples of some nucleic acids envisioned for this invention may contain phosphorothioates, phosphotriesters, methyl phosphonates, short chain alkyl or cycloalkyl intersugar linkages or short chain heteroatomic or heterocyclic intersugar linkages. Also preferred are oligonucleotides having morpholino backbone structures (Summerton, J. E. and Weller, D. D., U.S. Pat. No. 5,034,506). In other preferred embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone (P. E. Nielsen et al. Science 199: 254, 1997). Other preferred oligonucleotides may contain alkyl and halogen-substituted sugar moieties comprising one of the following at the 2' position: OH, SH, $SCH_3$, F, OCN, $O(CH_2)_nNH_2$ or $O(CH_2)_nCH_3$, where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group. Other preferred embodiments may include at least one modified base form. Some specific examples of such modified bases include 2-(amino)adenine, 2-(methylamino)adenine, 2-(imidazolylalkyl)adenine, 2-(aminoalklyamino)adenine, or other heterosubstituted alkyladenines.

The term "operably linked" means that a first polynucleotide is positioned adjacent to a second polynucleotide that directs transcription of the first polynucleotide when appropriate molecules (e.g., transcriptional activator proteins) are bound to the second polynucleotide.

By "recombinant" is meant the product of genetic engineering or chemical synthesis. By "positioned for expression" is meant that the polynucleotide of the present invention (e.g., a DNA molecule) is positioned adjacent to a DNA sequence that directs transcription and translation of the sequence (i.e., facilitates the production of, for example, a recombinant protein of the present invention, or an RNA molecule).

The term "reference" means a standard or control condition.

The terms "specifically binds to," "specific for," and related grammatical variants refer to that binding which occurs between such paired species as antibody/antigen, aptamer/target, enzyme/substrate, receptor/agonist and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, in certain embodiments, "specific binding" occurs between a paired species where there is interaction between the two which produces a bound complex having the characteristics of, for example, an antibody/antigen. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M. In certain embodiments, the term refers to a molecule (e.g., an antibody) that binds to a target (e.g., Resistin) with at least five-fold greater affinity as compared to any non-targets, e.g., at least 10-, 20-, 50-, or 100-fold greater affinity.

By "subject" is meant a mammal, including, but not limited to, a human or non-human mammal, such as a bovine, equine, canine, ovine, or feline.

By "substantially identical" is meant a protein or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and most preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e.sup.-3 and e.sup.-100 indicating a closely related sequence.

By "transformed cell" is meant a cell into which (or into an ancestor of which) has been introduced, by means of recombinant DNA techniques, a polynucleotide molecule encoding (as used herein) a protein of the present invention.

II. Antibodies to Resistin and Resistin-Like Molecule Beta (RELMB)

The present invention provides antibodies to Resistin. In some embodiments, the antibodies are also cross-reactive with Resistin-Like Molecule Beta (RELMB). An "antibody" is a polypeptide ligand including at least the complementarity determining regions (CDRs) of a light chain or heavy chain immunoglobulin variable region which specifically binds an epitope of an antigen or a fragment thereof. Antibodies include intact immunoglobulins and the variants of them well known in the art, such as Fab', F(ab)'2 fragments, single chain Fv proteins (scFv), and disulfide stabilized Fv proteins (dsFv). A scFvprotein is a fusion protein in which a light chain variable region of an antibody and a heavy chain variable region of an antibody are bound by a linker, while in dsFvs, the chains have been mutated to introduce a disulfide bond to stabilize the association of the chains. The term "antibody" also includes genetically engineered forms such as chimeric antibodies (for example, humanized murine antibodies) and heteroconjugate antibodies (such as, bispecific antibodies).

Typically, a naturally occurring immunoglobulin has heavy (H) chains and light (L) chains interconnected by disulfide bonds. There are two types of light chains, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region (the regions are also known as domains). References to "VH" or "VH" refer to the variable region of an immunoglobulin heavy chain, including that of an Fv, scFv, dsFv or Fab. References to "VL" or "VL" refer to the variable region of an immunoglobulin light chain, including that of an Fv, scFv, dsFv or Fab. In combination, the heavy and the light chain variable regions specifically bind the antigen. Light and heavy chain variable regions contain a framework region interrupted by three hypervariable regions, also called complementarity-determining regions or CDRs. The extent of the framework region and CDRs have been defined (see, for example, Kabat et al., (1991) Sequences of Proteins of Immunological Interest, 5lh Edition, U.S. Department of Health and Human Services, Public Health Service, National Institutes of Health, Bethesda, Md. (NIH Publication No. 91-3242), which is hereby incorporated by reference). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The precise amino acid sequence boundaries of a given CDR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), and Al-Lazikani et al., (1997) JMB 273, 927-948 ("Chothia" numbering scheme). The CDRs of each chain are typically referred to as CDR1, CDR2, and CDR3, numbered sequentially starting from the N-terminus, and are also typically identified by the chain in which the particular CDR is located. Thus, a HCDR1 is the CDR 1 from the variable domain of the heavy chain of the antibody in which it is found, whereas a LCDR 1 is the CDR1 from the variable domain of the light chain of the antibody in which it is found. An antibody that specifically binds an antigen of interest has a specific VH region and VL region sequence, and thus specific CDR sequences. Antibodies with different specificities (due to different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

A single-chain antibody (scFv) is a genetically engineered molecule containing the VH and VL domains of one or more antibody(ies) linked by a suitable polypeptide linker as a genetically fused single chain molecule. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites. A chimeric antibody is an antibody that contains one or more regions from one antibody and one or more regions from one or more other antibodies. An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

The antibodies disclosed herein specifically bind only to a defined target (or multiple targets, in the case of a bi-specific antibody). Thus, an antibody that specifically binds to Resistin is an antibody that binds substantially to Resistin, including cells or tissue expressing Resistin, substrate to which the Resistin is attached, or Resistin in a biological specimen. It is, of course, recognized that a certain degree of non-specific interaction may occur between an antibody or conjugate including an antibody (such as an antibody that specifically binds Resistin or conjugate including such antibody) and a non-target (such as a cell that does not express Resistin). Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope.

In one embodiment, an antibody that binds Resistin is monoclonal. Alternatively, the Resistin antibody is a polyclonal antibody. The preparation and use of polyclonal antibodies are also known the skilled artisan. The present invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "$F(ab\alpha)_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fabα fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (RIA) or enzyme-linked immunosorbent assay (ELISA) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated, such as from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different ways using recombinant DNA technology to generate alternative antibodies. In one embodiment, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

In some embodiments, of the present invention the monoclonal antibody against Resistin is a humanized antibody. Humanized antibodies are antibodies that contain minimal sequences from non-human (e.g., murine) antibodies within the variable regions. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDR of a human antibody with that of a non-human antibody (e.g., mouse, rat, rabbit, hamster, etc.) having the desired specificity, affinity, and capability (Jones et al., 1986, Nature, 321:522-525; Riechmann et al., 1988, Nature, 332:323-327; Verhoeyen et al., 1988, Science, 239:1534-1536). The humanized antibody can be further modified by the substitution of additional residue either in the Fv framework region and/or within the replaced non-human residues to refine and optimize antibody specificity, affinity, and/or capability.

Human antibodies can be directly prepared using various techniques known in the art. Immortalized human B lymphocytes immunized in vitro or isolated from an immunized individual that produce an antibody directed against a target antigen can be generated (See, for example, Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). Also, the human antibody can be selected from a phage library, where that phage library expresses human antibodies (Vaughan et al., 1996, Nature Biotechnology, 14:309-314; Sheets et al., 1998, PNAS, 95:6157-6162; Hoogenboom and Winter, 1991, J. Mol. Biol., 227:381; Marks et al., 1991, J. Mol. Biol., 222:581). Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain embodiments of the invention, it may be desirable to use an antibody fragment, rather than an intact antibody. Various techniques are known for the production of antibody fragments. Traditionally, these fragments are derived via proteolytic digestion of intact antibodies (for example Morimoto et al., 1993, Journal of Biochemical and Biophysical Methods 24:107-117 and Brennan et al., 1985, Science, 229:81). However, these fragments are now typically produced directly by recombinant host cells as described above. Thus Fab, Fv, and scFv antibody fragments can all be expressed in and secreted from *E. coli* or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent.

The present invention further embraces variants and equivalents which are substantially homologous to the chimeric, humanized and human antibodies, or antibody fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: Human Resistin Antibody Screen (ELISA)

Purpose.

Screen five candidate antibodies to human resistin for prospect at use in neutralization experiments against human resistin.

Background.

A direct-coat ELISA was performed (resistin coated to wells of plate, then run antibodies against immobilized antigen, see Protocol 1), identifying 12 antibodies to have "positive" reactivity, albeit to varying degree. From these 12, five have been selected for further analysis (all 17 candidate antibodies showed some level of success in binding human resistin, via immunoprecipitation); these five are those showing highest positive reactivity in the matrix: Ab1, Ab13, Ab17, Ab21, and Ab41. For potential as neutralizing antibodies, recognition of immobilized antigen is not sufficient. Direct evaluation of the antibodies with neutralization experiments are costly and can be inefficient as controls become detailed; thus, sandwich-type ELISA becomes a valid tool for evaluating which antibodies may be best suited for further analysis. Furthermore, this ELISA assay should provide useful information with regard to effective concentration(s) of the tested antibodies against a standard human resistin protein.

General Description of ELISA.

Indirect ELISA utilizes a set of two antibodies that recognize the target antigen arranged such that one antibody (capture antibody) is pre-adsorbed to the wells of a 96-well plate. A solution containing the antigen of interest is passed over the adsorbed capture antibody and some amount of antigen is usually removed from solution. The second antibody recognizing the antigen of interest is then added to the wells, and again some level of previously captured antigen is recognized by this second (detection antibody) antibody. Finally, a secondary antibody (commonly HRP tagged) that recognized the host species for production of the detection antibody is added to the wells, and substrate added for eventual quantification. There are several variations to this method.

Points of Note:

*It is imperative that the capture and detection antibodies are a "matched pair" in that they do not compete with one another for binding the target antigen, as this would deliver a false negative reading. Indirect/sandwich type ELISA kits from commercial sources have been vetted for this condition and will be labeled as such. Additionally, if the capture and detection antibody are from monoclonal and polyclonal sources, it is most common to use the monoclonal for capture, and the polyclonal as the detection antibody for maximum specificity.

*In the case of utilization of the indirect/sandwich ELISA for evaluation of a capture/detection antibody, it is possible to use a non-antigen specific antibody paired with the antibody under evaluation. For example, if the antigen can be had in a FLAG or HIS tag, or something similar, and provided the antibody under evaluation binding is not interrupted by the presence of such a tag or addition, then the second antibody (commonly the detection antibody) can be directed toward this additional motif (FLAG, HIS). This allows evaluation of antibodies without having to have more than one antibody directed toward the target antigen. Caution must be exercised here with regard to adequate controls for non-specific binding (wells with no capture antibody, wells with no antigen solution, wells with no detection antibody, etc.).

Specific Background on this ELISA:

Using part of R&D Systems Six-Pack (Cat # SRSN00; R&D Protocol):

Wash Buffer Concentrate #895003 (20 mL diluted to 500 mL with DI H2O)

hResistin standard #892671 (reconstituted with 1.0 mL DI H2O as per R&D Protocol)

hResistin conjugate #892670 (used as detection antibody as packaged)

Substrate solution #895000 and 895001 (11 mL each Solution A and B, mixed and used within 15 minutes as per R&D Protocol)

Stop Solution #895032 (used as packaged as per R&D Protocol)

For comparison, using a commercial monoclonal Ms anti-huRes (R&D #13591 clone 184305) as one of coated capture antibodies 96-well plate from R&D: # DY990, Lot 301409

Using range of resistin concentrations (normal is 25-50 ng/mL) to show effectiveness in detecting within, above, and below normal range.

Protocol:

Day 1:

1. Prepare ELISA coating buffer:

0.05 M Na2CO3/NaHCO3 (in one embodiment, 0.05 M is used; 0.05-0.1 M is common range)

2.173 g Na2CO3

3.528 g NaHCO3

Dissolve both in 1 L beaker, ~700 mL DI H2O. Correct pH to ~9.5 (9.51)

Q.S. to 1 L, re-check and adjust pH (9.54, 9.51 final)

Transfer to 1 L bottle, label, store at 4 C (Cold Room)

2. Prepare dilutions of 5 candidate capture antibodies (Ab1, Ab13, Ab17, Ab21, Ab41) for final concentrations: 5, 2, 1, 0.5 g/mL (Range is 1-12 g/mL in commercial kits, but for testing purposes and as some antibody quantities are limited, used 0.5-5 g/mL; 0.5-1.0 mL each prepared: 4 wells per concentration, 100 L/wl). Also made R&D Ab at 2, 1, 0.5 g/mL (leave 4 wells for 'blank,' see Plate Layout).

3. Add 100 L/well as per Plate Layout, each of 4 candidate antibodies at 4 dilutions in 4 wells each; Comparison R&D antibody at 3 dilutions in 4 wells each. Column 12, rows A-D left blank, loaded only coating buffer. *Used eppendorf repeating pipette for delivery of solutions.

4. Covered with sealing adhesive strip, put on rotator in cold room at 4° C. overnight.

Day 2:

5. Remove coating antibody and solution by inverting in sink, then wash 4 times with wash buffer, removing all liquid each time. After final rinse, invert on paper towels to blot excess liquid before adding Blocking Solution.

6. Add 250 L Blocking Solution: 2% BSA (w/v) in PBS-T (PBS [Commercial, Gibco] with 0.05% Tween 20). Cover with new sealing adhesive strip, block overnight at 4 C in cold room on rotator again.

*In some embodiments, probably not necessary to block overnight, was due to concurrent experiments in this case; 2 h at RT to overnight at 4 C is acceptable.

Day 3:

7. Set up dilutions of hResistin standard protein (as directed in R&D Protocol *Consult Protocol from R&D): 100, 25, 10, 1 ng/mL in PBST (See step 6 for preparation of PBST). Add 100 L each to appropriate wells (see plate layout). Add new sealing adhesive strip, incubate at room temperature 2 hours on rotator.

8. Remove hResistin protein and wash 4-5× as before. Add hRes conjugate antibody, 200 L/well ALL WELLS. Add new sealing adhesive strip, incubate at room temperature 2 hours on rotator. *With 5 minutes remaining, combine equal volumes of Substrate solution A and B, mix, let sit (must be used within 15 minutes of mixing) and protect from light.

9. Remove hResistin conjugate and wash 4-5× as above. Add 200 L/well ALL WELLS mixed Substrate Solution, cover with new adhesive sealing strip, tap sides gently to mix. Cover with foil to protect from light and place in drawer for 30 minutes.

10. Remove adhesive strip, add 50 L Stop Solution per well ALL WELLS, tap gently to mix. Read within 30 minutes at 450 and either 540 or 570 nm (subtract reading at 540 or 570 from 450 for correction).

Results

Antibodies 13, 17, 21, and 41 all show some reactivity in binding hResistin. Ab1 did not show sufficient reactivity to be considered above baseline. Overall, all five tested antibodies were far less competent in binding and pulling hResistin out of solution in comparison to the commercial R&D antibody.

Figure 7:
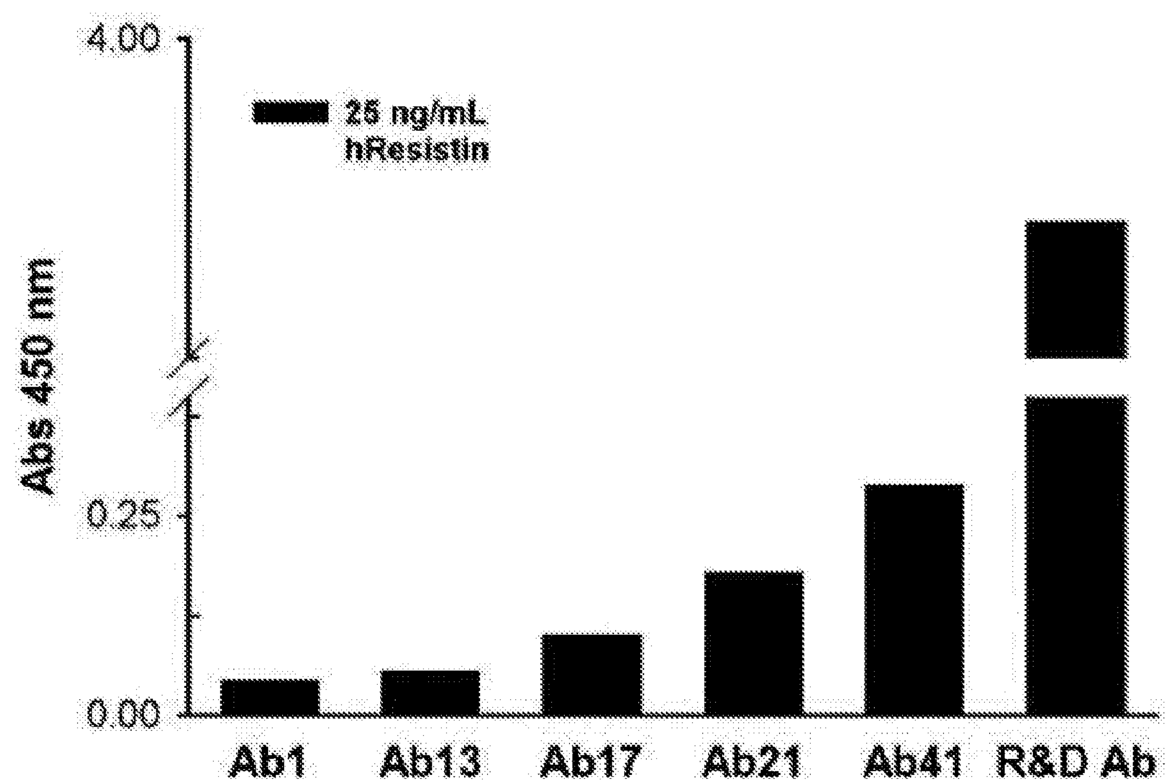
FIG. 7 is a graph comparing the antibody reactivity of all the antibodies with 25 ng/ml hResistin. R&D Ab at 1 μg/ml; all other Abs 5 μg/ml; values at 1 μg/ml R&D antibody used as value at 2 μg/ml is beyond absorbance range for the assay.
Figure 9:
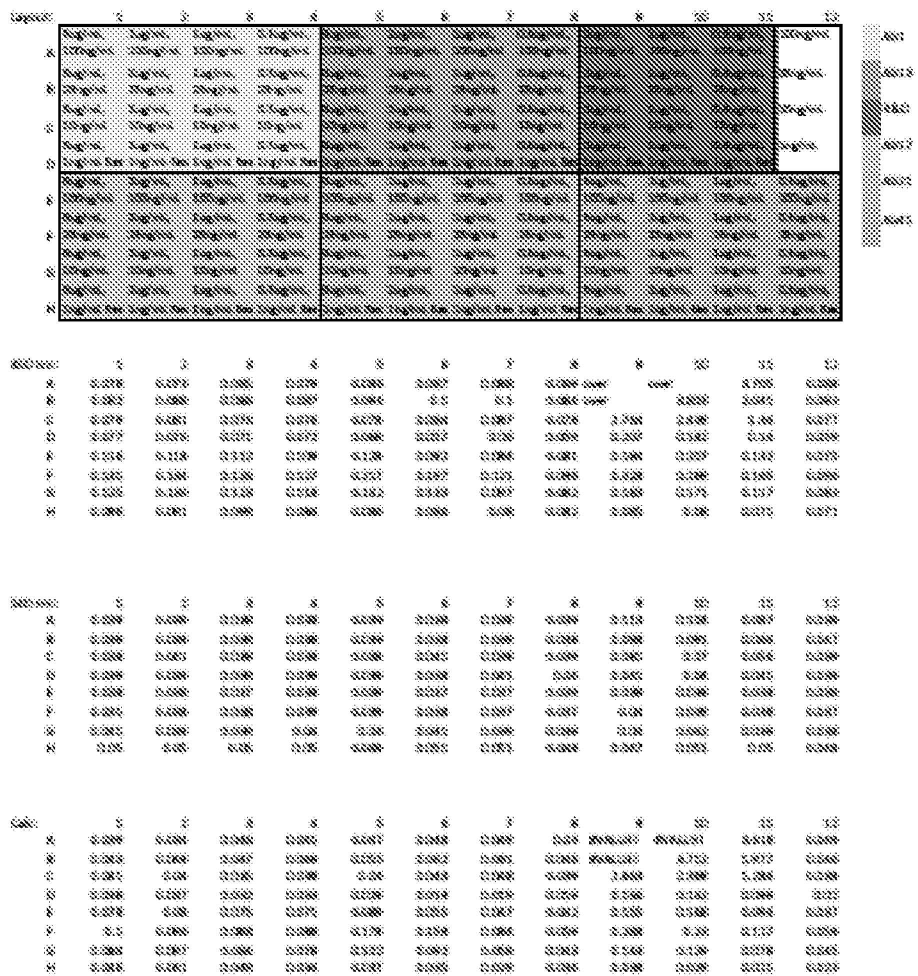
FIG. 9 shows the plate layout and resulting absorbance measurements for the hResistin antibody screen of Ab1, Ab13, Ab17, Ab21, Ab31 and R&D antibody.

FIGS. 1-6 show corrected absorbance at 450 nm of each of the five test and one comparison antibody, note that all test antibodies are shown with the same Z/Absorbance axis, but R&D antibody (FIG. 6) is much larger axis. FIG. 7 compares all six antibodies present on the plate, at maximum coating antibody concentration and at 25 ng/mL hResistin added (corresponds to maxima of most test antibodies; see individual figures).

Discussion

Antibodies 13, 17, 21, and 41 all show saturation in huRes binding at ~25 ng/mL, with antibodies concentration at 5 g/mL.

Example 2: Convert scfv into Fully Human IgG1

Figure 10:
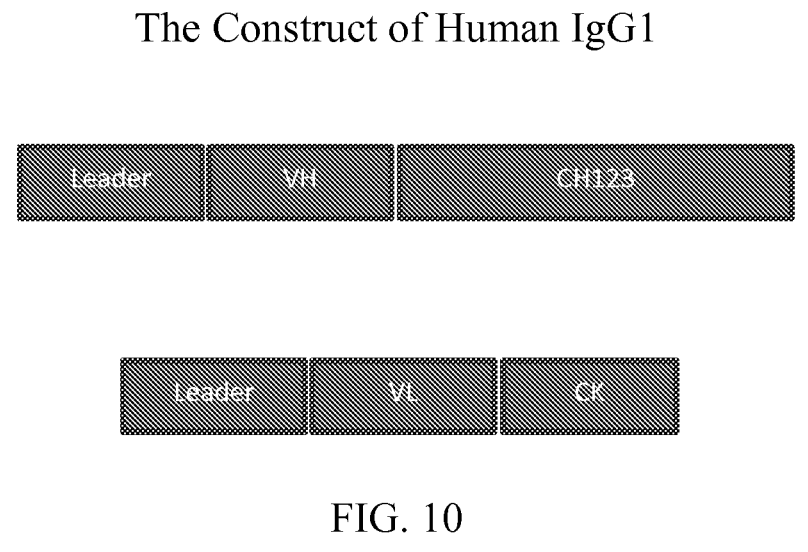

The seventeen scfv (nucleotide sequences found in SEQ ID NO:1, SEQ ID NO:11, SEQ ID NO:21, SEQ ID NO:31, SEQ ID NO:41, SEQ ID NO:51, SEQ ID NO:61, SEQ ID NO:71, SEQ ID NO:81, SEQ ID NO:91, SEQ ID NO:101, SEQ ID NO:111, SEQ ID NO:121, SEQ ID NO:131, SEQ ID NO:141, SEQ ID NO:151 and SEQ ID NO:161; amino acid sequences found in SEQ ID NO:2, SEQ ID NO:12, SEQ ID NO:22, SEQ ID NO:32, SEQ ID NO:42, SEQ ID NO:52, SEQ ID NO:62, SEQ ID NO:72, SEQ ID NO:82, SEQ ID NO:92, SEQ ID NO:102, SEQ ID NO:112, SEQ ID NO:122, SEQ ID NO:132, SEQ ID NO:142, SEQ ID NO:152, SEQ ID NO:162) converted into fully human IgG1. Briefly, the cDNA of the variable heavy (SEQ ID NO:3, SEQ ID NO:13, SEQ ID NO:23, SEQ ID NO:33, SEQ ID NO:43, SEQ ID NO:53, SEQ ID NO:63, SEQ ID NO:73, SEQ ID NO:83, SEQ ID NO:93, SEQ ID NO:103, SEQ ID NO:113, SEQ ID NO:123, SEQ ID NO:133, SEQ ID NO:143, SEQ ID NO:153, SEQ ID NO:163) and the variable light (SEQ ID NO:7, SEQ ID NO:17, SEQ ID NO:27, SEQ ID NO:37, SEQ ID NO:47, SEQ ID NO:57, SEQ ID NO:67, SEQ ID NO:77, SEQ ID NO:87, SEQ ID NO:97, SEQ ID NO:107, SEQ ID NO:117, SEQ ID NO:127, SEQ ID NO:137, SEQ ID NO:147, SEQ ID NO:157, SEQ ID NO:167) were subcloned into an IgG-expressing vector. Two separate vectors for the light chain and heavy chain were used. The vectors were transiently transfected in 293 cells, and the expressed IgGs were purified with Protein A or G. The sequences for the heavy constant region are shown in SEQ ID NO:171 (nucleotide) and SEQ ID NO:172 (amino acid). The sequences for the light constant region are shown in SEQ ID NO:173 (nucleotide) and SEQ ID NO:174 (amino acid). See also FIG. 10.

Example 3: rIgGs Show Cross-Reactivity to RELMβ

As shown in FIG. 11, the supernatant of cells expressing 17 rIgG was subjected to QC ELISA in which two targets were coated in parallel. As a result, 4 IgGs (Clones 1, 2, 13 and 18) bind to two targets positively. hRELMβ3: 0.5 μg/well; hResistin: 5 μg/well; secondary antibody: FITC-goat anti-human IgG pAb.

I claim:

1. An anti-Resistin antibody or antigen-binding fragment thereof comprising a heavy chain variable region and a light chain variable region, wherein:

(a) the heavy chain variable region comprises SEQ ID NO:3 or a conservative substitution at up to 5 amino acid positions of SEQ ID NO:3, and the light chain variable region comprises SEQ ID NO:7 or a conservative substitution at up to 5 amino acid positions of SEQ ID NO:7;

(b) the heavy chain variable region comprises SEQ ID NO:13 or a conservative substitution at up to 5 amino acid positions of SEQ ID NO:13, and the light chain variable region comprises SEQ ID NO:17 or a conservative substitution at up to 5 amino acid positions of SEQ ID NO:17;

(c) the heavy chain variable region comprises SEQ ID NO:23 or a conservative substitution at up to 5 amino acid positions of SEQ ID NO:23, and the light chain variable region comprises SEQ ID NO:27 or a conservative substitution at up to 5 amino acid positions of SEQ ID NO:27;

(d) the heavy chain variable region comprises SEQ ID NO:33 or a conservative substitution at up to 5 amino acid positions of SEQ ID NO:33 and the light chain variable region comprises SEQ ID NO:37 or a conservative substitution at up to 5 amino acid positions of SEQ ID NO:37;

(e) the heavy chain variable region comprises SEQ ID NO:43 or a conservative substitution at up to 5 amino acid positions of SEQ ID NO:43, and the light chain variable region comprises SEQ ID NO:47 or a conservative substitution at up to 5 amino acid positions of SEQ ID NO:47;

(f) the heavy chain variable region comprises SEQ ID NO:53 or a conservative substitution at up to 5 amino acid positions of SEQ ID NO:53, and the light chain variable region comprises SEQ ID NO:57 or a conservative substitution at up to 5 amino acid positions of SEQ ID NO:57;

(g) the heavy chain variable region comprises SEQ ID NO:63 or a conservative substitution at up to 5 amino acid positions of SEQ ID NO:63 and the light chain variable region comprises SEQ ID NO:67 or a conservative substitution at up to 5 amino acid positions of SEQ ID NO:67;

(h) the heavy chain variable region comprises SEQ ID NO:73 or a conservative substitution at up to 5 amino acid positions of SEQ ID NO:73, and the light chain variable region comprises SEQ ID NO:77 or a conservative substitution at up to 5 amino acid positions of SEQ ID NO:77;

(i) the heavy chain variable region comprises SEQ ID NO:83 or a conservative substitution at up to 5 amino acid positions of SEQ ID NO:83, and the light chain variable region comprises SEQ ID NO:87 or a conservative substitution at up to 5 amino acid positions of SEQ ID NO:87;

(j) the heavy chain variable region comprises SEQ ID NO:93 or a conservative substitution at up to 5 amino acid positions of SEQ ID NO:93 and the light chain variable region comprises SEQ ID NO:97 or a conservative substitution at up to 5 amino acid positions of SEQ ID NO:97;

(k) the heavy chain variable region comprises SEQ ID NO:103 or a conservative substitution at up to 5 amino acid positions of SEQ ID NO:103, and the light chain variable region comprises SEQ ID NO:107 or a conservative substitution at up to 5 amino acid positions of SEQ ID NO:107;

(l) the heavy chain variable region comprises SEQ ID NO:113 or a conservative substitution at up to 5 amino acid positions of SEQ ID NO:113 and the light chain variable region comprises SEQ ID NO:117 or a conservative substitution at up to 5 amino acid positions of SEQ ID NO:117;

(m) the heavy chain variable region comprises SEQ ID NO:123 or a conservative substitution at up to 5 amino acid positions of SEQ ID NO:123, and the light chain variable region comprises SEQ ID NO:127 or a conservative substitution at up to 5 amino acid positions of SEQ ID NO:127;

(n) the heavy chain variable region comprises SEQ ID NO:133 or a conservative substitution at up to 5 amino acid positions of SEQ ID NO:133, and the light chain variable region comprises SEQ ID NO:137 or a conservative substitution at up to 5 amino acid positions of SEQ ID NO:137;

(o) the heavy chain variable region comprises SEQ ID NO:143 or a conservative substitution at up to 5 amino acid positions of SEQ ID NO:143, and the light chain variable region comprises SEQ ID NO:147 or a conservative substitution at up to 5 amino acid positions of SEQ ID NO:147;

(p) the heavy chain variable region comprises SEQ ID NO:153 or a conservative substitution at up to 5 amino acid positions of SEQ ID NO:153, and the light chain variable region comprises SEQ ID NO:157 or a conservative substitution at up to 5 amino acid positions of SEQ ID NO:157; or (q) the heavy chain variable region comprises SEQ ID NO:163 or a conservative substitution at up to 5 amino acid positions of SEQ ID NO:163 and the light chain variable region comprises SEQ ID NO:167 or a conservative substitution at up to 5 amino acid positions of SEQ ID NO:167.

2. The anti-Resistin antibody or antigen-binding fragment thereof of claim 1, further comprising a heavy chain constant region comprising SEQ ID NO:172 and a light chain constant region comprising SEQ ID NO:174.

3. An anti-Resistin antibody or antigen-binding fragment thereof comprising:

(a) a heavy chain variable region comprising complementarity determining regions (CDRs) 1, 2 and 3 comprising SEQ ID NOS:4-6, respectively, or a conservative substitution at up to 2 amino acids of one or more of SEQ ID NOS:4-6, and a light chain variable region comprising CDRs 1, 2, and 3 comprising SEQ ID NOS:8-10, respectively, or a conservative substitution at up to 2 amino acids of one or more of SEQ ID NOS:8-10;

(b) a heavy chain variable region comprising CDRs 1, 2 and 3 comprising SEQ ID NOS:14-16, respectively, or a conservative substitution at up to 2 amino acids of one or more of SEQ ID NOS:14-16, and a light chain variable region comprising CDRs 1, 2, and 3 comprising SEQ ID NOS:18-20, respectively, or a conservative substitution at up to 2 amino acids of one or more of SEQ ID NOS:18-20;

(c) a heavy chain variable region comprising CDRs 1, 2 and 3 comprising SEQ ID NOS:24-26, respectively, or a conservative substitution at up to 2 amino acids of one or more of SEQ ID NOS:24-26, and a light chain variable region comprising CDRs 1, 2, and 3 comprising SEQ ID NOS:28-30, respectively, or a conservative substitution at up to 2 amino acids of one or more of SEQ ID NOS:28-30;

(d) a heavy chain variable region comprising CDRs 1, 2 and 3 comprising SEQ ID NOS:34-36, respectively, or a conservative substitution at up to 2 amino acids of one or more of SEQ ID NOS:34-36, and a light chain variable region comprising CDRs 1, 2, and 3 comprising SEQ ID NOS:38-40, respectively, or a conservative substitution at up to 2 amino acids of one or more of SEQ ID NOS:38-40;

(e) a heavy chain variable region comprising CDRs 1, 2 and 3 comprising SEQ ID NOS:44-46, respectively, or a conservative substitution at up to 2 amino acids of one or more of SEQ ID NOS:44-46, and a light chain variable region comprising CDRs 1, 2, and 3 comprising SEQ ID NOS:48-50, respectively, or a conservative substitution at up to 2 amino acids of one or more of SEQ ID NOS:48-50;

(f) a heavy chain variable region comprising CDRs 1, 2 and 3 comprising SEQ ID NOS:54-56, respectively, or a conservative substitution at up to 2 amino acids of one or more of SEQ ID NOS:54-56, and a light chain variable region comprising CDRs 1, 2, and 3 comprising SEQ ID NOS:58-60, respectively, or a conservative substitution at up to 2 amino acids of one or more of SEQ ID NOS:58-60;

(g) a heavy chain variable region comprising CDRs 1, 2 and 3 comprising SEQ ID NOS:64-66, respectively, or a conservative substitution at up to 2 amino acids of one or more of SEQ ID NOS:64-66, and a light chain variable region comprising CDRs 1, 2, and 3 comprising SEQ ID NOS:68-70, respectively, or a conservative substitution at up to 2 amino acids of one or more of SEQ ID NOS:68-70;

(h) a heavy chain variable region comprising CDRs 1, 2 and 3 comprising SEQ ID NOS:74-76, respectively, or a conservative substitution at up to 2 amino acids of one or more of SEQ ID NOS:74-76, and a light chain variable region comprising CDRs 1, 2, and 3 comprising SEQ ID NOS:78-80, respectively, or a conservative substitution at up to 2 amino acids of one or more of SEQ ID NOS:78-80;

(i) a heavy chain variable region comprising CDRs 1, 2 and 3 comprising SEQ ID NOS:84-86, respectively, or a conservative substitution at up to 2 amino acids of one or more of SEQ ID NOS:84-86, and a light chain variable region comprising CDRs 1, 2, and 3 comprising SEQ ID NOS:88-90, respectively, or a conservative substitution at up to 2 amino acids of one or more of SEQ ID NOS:88-90;

(j) a heavy chain variable region comprising CDRs 1, 2 and 3 comprising SEQ ID NOS:94-96, respectively, or a conservative substitution at up to 2 amino acids of one or more of SEQ ID NOS:94-96, and a light chain variable region comprising CDRs 1, 2, and 3 comprising SEQ ID NOS:98-100, respectively, or a conservative substitution at up to 2 amino acids of one or more of SEQ ID NOS:98-100;

(k) a heavy chain variable region comprising CDRs 1, 2 and 3 comprising SEQ ID NOS:104-106, respectively, or a conservative substitution at up to 2 amino acids of one or more of SEQ ID NOS:104-106, and a light chain variable region comprising CDRs 1, 2, and 3 comprising SEQ ID NOS:108-110, respectively, or a conservative substitution at up to 2 amino acids of one or more of SEQ ID NOS:108-110;

(l) a heavy chain variable region comprising CDRs 1, 2 and 3 comprising SEQ ID NOS:114-116, respectively, or a conservative substitution at up to 2 amino acids of one or more of SEQ ID NOS:114-116, and a light chain variable region comprising CDRs 1, 2, and 3 comprising SEQ ID NOS:118-120, respectively, or a conservative substitution at up to 2 amino acids of one or more of SEQ ID NOS:118-120;

(m) a heavy chain variable region comprising CDRs 1, 2 and 3 comprising SEQ ID NOS:124-126, respectively, or a conservative substitution at up to 2 amino acids of one or more of SEQ ID NOS:124-126, and a light chain variable region comprising CDRs 1, 2, and 3 comprising SEQ ID NOS:128-130, respectively, or a conservative substitution at up to 2 amino acids of one or more of SEQ ID NOS:128-130;

(n) a heavy chain variable region comprising CDRs 1, 2 and 3 comprising SEQ ID NOS:134-136, respectively, or a conservative substitution at up to 2 amino acids of one or more of SEQ ID NOS:134-136, and a light chain variable region comprising CDRs 1, 2, and 3 comprising SEQ ID NOS:138-140, respectively, or a conservative substitution at up to 2 amino acids of one or more of SEQ ID NOS:138-140;

(o) a heavy chain variable region comprising CDRs 1, 2 and 3 comprising SEQ ID NOS:144-146, respectively, or a conservative substitution at up to 2 amino acids of one or more of SEQ ID NOS:144-146, and a light chain variable region comprising CDRs 1, 2, and 3 comprising SEQ ID NOS:148-150, respectively, or a conservative substitution at up to 2 amino acids of one or more of SEQ ID NOS:148-150;

(p) a heavy chain variable region comprising CDRs 1, 2 and 3 comprising SEQ ID NOS:154-156, respectively, or a conservative substitution at up to 2 amino acids of one or more of SEQ ID NOS:154-156, and a light chain variable region comprising CDRs 1, 2, and 3 comprising SEQ ID NOS:158-160, respectively, or a conservative substitution at up to 2 amino acids of one or more of SEQ ID NOS:158-160; or (q) a heavy chain variable region comprising CDRs 1, 2 and 3 comprising SEQ ID NOS:164-166, respectively, or a conservative substitution at up to 2 amino acids of one or more of SEQ ID NOS:164-166, and a light chain variable region comprising CDRs 1, 2, and 3 comprising SEQ ID NOS:168-170, or a conservative substitution at up to 2 amino acids of one or more of SEQ ID NOS:168-170.

4. The anti-Resistin antibody or antigen-binding fragment thereof of claim 3, further comprising a heavy chain constant region comprising SEQ ID NO:172 and a light chain constant region comprising SEQ ID NO:174.

5. A single chain variable fragment (scFv) or antigen-binding fragment thereof that binds Resistin, wherein the scFv comprises SEQ ID NO:2 or a conservative substitution at up to 5 amino acids of SEQ ID NO:2; SEQ ID NO:12 or a conservative substitution at up to 5 amino acids of SEQ ID NO:12; SEQ ID NO:22 or a conservative substitution at up to 5 amino acids of SEQ ID NO:22; SEQ ID NO:32 or a conservative substitution at up to 5 amino acids of SEQ ID NO:32; SEQ ID NO:42 or a conservative substitution at up to 5 amino acids of SEQ ID NO:42; SEQ ID NO:52 or a conservative substitution at up to 5 amino acids of SEQ ID NO:52; SEQ ID NO:62 or a conservative substitution at up to 5 amino acids of SEQ ID NO:62; SEQ ID NO:72 or a conservative substitution at up to 5 amino acids of SEQ ID NO:72; SEQ ID NO:82 or a conservative substitution at up to 5 amino acids of SEQ ID NO:82; SEQ ID NO:92 or a conservative substitution at up to 5 amino acids of SEQ ID NO:92; SEQ ID NO:102 or a conservative substitution at up to 5 amino acids of SEQ ID NO:102; SEQ ID NO:112 or a conservative substitution at up to 5 amino acids of SEQ ID NO:112; SEQ ID NO:122 or a conservative substitution at up to 5 amino acids of SEQ ID NO:122; SEQ ID NO:132 or a conservative substitution at up to 5 amino acids of SEQ ID NO:132; SEQ ID NO:142 or a conservative substitution at up to 5 amino acids of SEQ ID NO:142; SEQ ID NO:152 or a conservative substitution at up to 5 amino acids of SEQ ID NO:152; or SEQ ID NO:162 or a conservative substitution at up to 5 amino acids of SEQ ID NO:162.

6. A method for treating arteriosclerosis or insulin resistance in a patient comprising the step of administering to the patient an antibody of claim 1-2, 3 or 4, or a single chain variable fragment of claim 5.

* * * * *